US007498333B2

(12) United States Patent
Aquila et al.

(10) Patent No.: US 7,498,333 B2
(45) Date of Patent: Mar. 3, 2009

(54) ENANTIOMERS OF SELECTED FUSED HETEROCYCLICS AND USES THEREOF

(75) Inventors: Brian Aquila, Waltham, MA (US); Michael Howard Block, Waltham, MA (US); Audrey Davies, Waltham, MA (US); Jayachandran Ezhuthachan, Brookline, MA (US); Sandra Ann Filla, Franklin, IN (US); Timothy Pontz, Waltham, MA (US); Daniel John Russell, Waltham, MA (US); Maria-Elena Theoclitou, Macclesfield (GB); XiaoLan Zheng, Waltham, MA (US)

(73) Assignee: AstraZeneca AB, Södertälje (SE)

( * ) Notice: Subject to any disclaimer, the term of this patent is extended or adjusted under 35 U.S.C. 154(b) by 106 days.

(21) Appl. No.: 11/207,128

(22) Filed: Aug. 18, 2005

(65) Prior Publication Data
US 2006/0041129 A1 Feb. 23, 2006

Related U.S. Application Data

(60) Provisional application No. 60/602,366, filed on Aug. 18, 2004.

(51) Int. Cl.
C07D 498/04 (2006.01)
A61K 31/505 (2006.01)

(52) U.S. Cl. .................. 514/260.1; 544/255
(58) Field of Classification Search ......... 544/255; 514/260.1
See application file for complete search history.

(56) References Cited

U.S. PATENT DOCUMENTS

| 6,630,479 | B1 | 10/2003 | Finer et al. |
| 6,809,102 | B2 | 10/2004 | Kimball et al. |
| 6,924,376 | B2 | 8/2005 | McDonald et al. |
| 2003/0008888 | A1 | 1/2003 | Kimball et al. |
| 2003/0166933 | A1 | 9/2003 | Bergnes et al. |
| 2004/0077662 | A1 | 4/2004 | Zhou et al. |
| 2004/0077668 | A1 | 4/2004 | Feng et al. |
| 2004/0116400 | A1 | 6/2004 | McDonald et al. |
| 2004/0116438 | A1 | 6/2004 | Lu et al. |
| 2004/0242596 | A1 | 12/2004 | Kim et al. |
| 2004/0259826 | A1 | 12/2004 | Fraley et al. |
| 2005/0032817 | A1 | 2/2005 | Fraley et al. |
| 2005/0065169 | A1 | 3/2005 | Wang et al. |
| 2005/0085490 | A1 | 4/2005 | Wang et al. |
| 2005/0107404 | A1 | 5/2005 | Fraley et al. |
| 2005/0148593 | A1 | 7/2005 | Bergnes |
| 2005/0158320 | A1 | 7/2005 | Nichols et al. |
| 2005/0165089 | A1 | 7/2005 | Bergnes et al. |
| 2005/0171122 | A1 | 8/2005 | Fraley et al. |
| 2005/0176717 | A1 | 8/2005 | Kim |
| 2005/0176737 | A1 | 8/2005 | Fraley et al. |
| 2005/0187232 | A1 | 8/2005 | Finer et al. |
| 2005/0228002 | A1 | 10/2005 | Wang et al. |
| 2006/0041128 | A1 | 2/2006 | Aquila et al. |
| 2006/0063751 | A1 | 3/2006 | Aquila et al. |
| 2006/0270689 | A1 | 11/2006 | Aquila et al. |

FOREIGN PATENT DOCUMENTS

| WO | WO 96/22991 A1 | 8/1996 |
| WO | WO 97/33890 A1 | 9/1997 |
| WO | WO 00/39131 A1 | 7/2000 |
| WO | WO 01/19800 A2 | 3/2001 |
| WO | WO 01/30768 A1 | 5/2001 |
| WO | WO 01/98278 A1 | 12/2001 |
| WO | WO 02/078639 A2 | 10/2002 |
| WO | WO 02/079149 A2 | 10/2002 |
| WO | WO 02/079169 A1 | 10/2002 |
| WO | WO 02/083143 A1 | 10/2002 |
| WO | WO 02/085909 A1 | 10/2002 |
| WO | WO 03/039460 A2 | 5/2003 |
| WO | WO 03/049527 A2 | 6/2003 |
| WO | WO 03/049527 A3 | 6/2003 |
| WO | WO 03/049678 A2 | 6/2003 |
| WO | WO 03/049679 A2 | 6/2003 |
| WO | WO 03/049679 A3 | 6/2003 |
| WO | WO 03/050064 A2 | 6/2003 |
| WO | WO 03/050122 A2 | 6/2003 |
| WO | WO 03/070701 A2 | 8/2003 |
| WO | WO 03/088903 A2 | 10/2003 |
| WO | WO 03/094839 A2 | 11/2003 |
| WO | WO 03/094839 A3 | 11/2003 |
| WO | WO 03/097053 A1 | 11/2003 |
| WO | WO 03/099211 A2 | 12/2003 |
| WO | WO 03/099286 A1 | 12/2003 |

(Continued)

OTHER PUBLICATIONS

AACR Poster 1335, 2002; SB-715992, a potent and selective inhibitor of KSP mitotic kinesin, demonstrates broad-spectrum activity in advanced murine tumors and human tumor xenografts.

(Continued)

Primary Examiner—Bruck Kifle

(57) ABSTRACT

This invention relates to novel compounds having the structural formula (I)

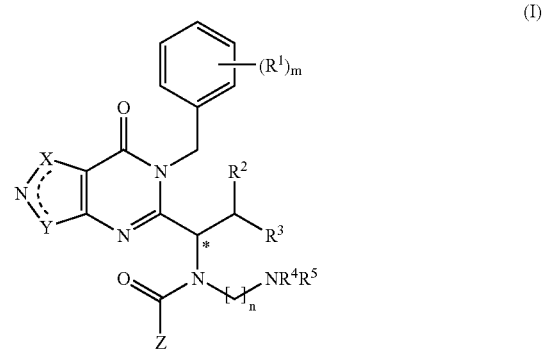

and to their pharmaceutical compositions and to their methods of use. These novel compounds provide a treatment or prophylaxis of cancer.

4 Claims, No Drawings

FOREIGN PATENT DOCUMENTS

| WO | WO 03/103575 A2 | 12/2003 |
| --- | --- | --- |
| WO | WO 03/106426 A1 | 12/2003 |
| WO | WO 2004/006865 A2 | 1/2004 |
| WO | WO 2004/009036 A2 | 1/2004 |
| WO | WO 2004/018058 A2 | 3/2004 |
| WO | WO 2004/024086 A2 | 3/2004 |
| WO | WO 2004/032840 A2 | 4/2004 |
| WO | WO 2004/032879 A2 | 4/2004 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 A1 | 9/2004 |
| WO | WO 2004/091547 A2 | 10/2004 |
| WO | WO 2004/100873 A2 | 11/2004 |
| WO | WO 2004/103282 A2 | 12/2004 |
| WO | WO 2004/106492 A2 | 12/2004 |
| WO | WO 2004/111058 A1 | 12/2004 |
| WO | WO 2004/113335 A2 | 12/2004 |
| WO | WO 2005/013888 A2 | 2/2005 |
| WO | WO 2005/042697 A2 | 5/2005 |
| WO | WO 2005/046588 A2 | 5/2005 |
| WO | WO 2005/051922 A1 | 6/2005 |
| WO | WO 2005/061460 A1 | 7/2005 |
| WO | WO2005/100357 | 10/2005 |
| WO | WO2005/113507 | 12/2005 |
| WO | WO2006/002236 | 1/2006 |
| WO | 2006/018627 A1 | 2/2006 |

OTHER PUBLICATIONS

AACR Poster 325, 2002; Inhibitors of the mitotic kinesin KSP: Biochemical mechanism of action.

AACR Poster 3648, 2002; Mitotic Kinesin-Targeted Antitumor Agents: Discovery, Lead Optimization and Anti-Tumor Activity of a Series of Novel Quinazolinones as Inhibitors of Kinesin Spindle Protein (KSP).

Debonis S, et al "Interaction of the Mitotic Inhibitor Monastrol with Human Kinesin Eg5" Biochemistry 42, 338-349, 2003.

Gartner M, et al "Development and Biological Evaluation of Potent and Specific Inhibitors of Mitotic Kinesin Eg5" ChemBioChem 6, 1-6, 2005.

Bergnes G, et al "Mitotic Kinesins: Prospects for Antimitotic Drug Discovery" Current Topics in Medicinal Chemistry 5, 127-145, 2005.

Coleman P; et al "Inhibitors of the mitotic kinsin spindle protein" Expert Opinion in Therapeutic Patents 14(12), 1659-1667, 2004.

Gordon Conf Med Chem Cytokinetics 2003: Bergnes, G: Mitotic Kinesin Inhibitors as Antitumor Agents.

Kappe C; et al "X-Ray Structure, Conformational Analysis, Enantioseparation, and Determination of Absolute Configuration of the Mitotic Kinesin Eg5 Inhibitor Monastrol" Tetrahedron 56, 1859-1862, 2000.

Duhl D; et al "Inhibitors of kinesin motor proteins—research and clinical progress" Current Opinion in Drug Discovery & Development 8(4) 431-436, 2005.

Maliga Z; et al "Evidence that Monastrol is an Allosteric Inhibitor of the Mitotic Kinesin Eg5" Chemistry & Biology, vol. 9, 989-996, Sep. 2002.

Mayer T; et al "Small Molecule Inhibitor of Mitotic Spindle Bipolarity Identified in a Phenotype-Based Screen" Science, vol. 286, 971-974, Oct. 29, 1999.

Tao W. et al "Induction of apoptosis by an inhibitor of the mitotic kinesin KSP requires both activation of the spindle assembly checkpoint and mitotic slippage" Cancer Cell vol. 8, 49-59, Jul. 2005.

Cox C, et al "Kinesin spindle protein (KSP) inhibitors. Part 1: The discovery of 3,5-diaryl-4,5 dihydropyrazoles as potent and selective inhibitors of the mitotic kinesin KSP" Science Direct, Elsevier Ltd., 2005 and Bioorganic and Medicianal Chemistry Letters, 2005.

Furneaux R; et al "Improved Syntheses of 3$H$-Pyrrolo[3,2-$d$]pyrimidines" J. Org. Chem. 64, 8411-8412, 1999.

Brier S; et al "Identification of the Protein Binding Region of $S$-Trityl-L-cysteine, a New Potent Inhibitor of the Mitotic Kinesin Eg5" Biochemistry 43, 13072-13082, 2004.

Marcus A; et al "Mitotic Kinesin Inhibitors Induce Mitotic Arrest and Cell Death in Taxol-resistant and -sensitive Cancer Cells" The Journal of Biological Chemistry vol. 280, No. 12, 11569-11577, 2005.

Nakazawa, J, et al "A Novel Action of Terpendole E on the Motor Activity of Mitotic Kinesin Eg5" Chemistry & Biology, vol. 10, 131-137, Feb. 2003.

Sasaki S; et al "Discovery of a Thieno[2,3-$d$]pyrimidine-2,4-dione Bearing a $p$-Methoxyureidophenyl Moiety at the 6-Position: A Highly Potent and Orally Bioavailable Non-Peptide Antagonist for the Human Luteinizing Hormone-Releasing Hormone Receptor" J. Med. Chem. 46, 113-124, 2003.

Sakowicz R; et al "Antiumor Activity of a Kinesin Inhibitor" Cancer Research 64, 3276-3280, May 1, 2004.

M. Ovcharova and E.S. Golovchinskaya, Syntheses in the Purine Series, VIII 1,0-Dimethylhypoxanthine-2- Alonic Ester and its reactions, Zhurnal Obshchei Khimii 1964, 34 (10), 3254-9.

M. Ovcharova, L. N. Babenko, and E.S. Golovchinskaya, [Title of Journal] Syntheses in a Series of Purine Derivatives, XVII New Derivatives of 1,7-Dimethylhypoxanthine, Khimiko-Farmatsevticheskii Zhurnal (1967), 1(3), 37-40.

United States Patent and Trademark Office, Office Action Summary for U.S. Appl. No. 11/207,089, mailed Aug. 17, 2007.

United States Patent and Trademark Office, Office Action Summary for U.S. Appl. No. 10/548,138, mailed Feb. 11, 2008.

Devlin, Theresa, Response to US Office Action filed May 12, 2008 for U.S. Appl. No. 10/548,138.

United States Patent and Trademark Office, Office Action Summary for U.S. Appl. No. 11/573,671, mailed Aug. 17, 2007.

Devlin, Theresa, Response to US Office Action filed Feb. 19, 2008 for U.S. Appl. No. 11/573,671.

United States Patent and Trademark Office, Office Action Summary for U.S. Appl. No. 11/206,888, mailed Aug. 20, 2007.

Devlin, Theresa, Response to US Office Action filed Feb. 19, 2008 for U.S. Appl. No. 11/206,888.

United States Patent and Trademark Office, Office Action Summary for U.S. Appl. No. 11/206,888, mailed May 12, 2008.

United States Patent and Trademark Office, Office Action Summary for U.S. Appl. No. 11/573,671, mailed May 12, 2008.

AstraZeneca Contract Research Agreement Dated Apr. 29, 2002.

ENANTIOMERS OF SELECTED FUSED HETEROCYCLICS AND USES THEREOF

This application claims the benefit of U.S. Application No. 60/602,366 filed on 18 Aug. 2004 the contents of which are incorporated herein by reference.

FIELD OF THE INVENTION

The present invention relates to novel fused heterocycles, their pharmaceutical compositions and methods of use. In addition, the present invention relates to therapeutic methods for the treatment and prevention of cancers and to the use of these chemical compounds in the manufacture of a medicament for use in the treatment and prevention of cancers.

BACKGROUND OF THE INVENTION

One sub-class of anti-cancer drugs (taxanes, vinca-alkaloids) now used extensively in the clinic is directed at microtubules and block the cell division cycle by interfering with normal assembly or disassembly of the mitotic spindle (see Chabner, B. A., Ryan, D. P., Paz-Ares, 1., Garcia-Carbonero, R., and Calabresi, P: Antineoplastic agents. In Hardman, J. G., Limbird, L. E., and Gilman, A. G., eds. Goodman and Gilman's The Pharmacological Basis of Therapeutics, 10$^{th}$ edition, 2001, The MacGraw-Hill Companies, Inc.). Taxol® (paclitaxel), one of the most effective drugs of this class, is a microtubule stabilizer. It interferes with the normal growth and shrinkage of microtubules thus blocking cells in the metaphase of mitosis. Mitotic block is often followed by slippage into the next cell cycle without having properly divided, and eventually by apoptosis of these abnormal cells (Blagosklonny, M. V. and Fojo, T.: Molecular effects of paclitaxel: myths and reality (a critical review). *Int J Cancer* 1999, 83:151-156.).

Some of the side effects of treatment with paclitaxel are neutropenia and peripheral neuropathy. Paclitaxel is known to cause abnormal bundling of microtubules in interphase cells. In addition, some tumor types are refractory to treatment with paclitaxel, and other tumors become insensitive during treatment. Paclitaxel is also a substrate for the multi-drug resistance pump, P-glycoprotein ((see Chabner et al., 2001).

Thus, there is a need for effective anti-mitotic agents that have fewer side effects than anti-microtubule drugs, and also for agents that are effective against taxane-resistant tumors.

Kinesins are a large family of molecular motor proteins, which use the energy of adenosine 5'-triphosphate (ATP) hydrolysis to move in a stepwise manner along microtubules. For a review, see Sablin, E. P.: Kinesins and microtubules: their structures and motor mechanisms. *Curr Opin Cell Biol* 2000, 12:35-41 and Schief, W. R. and Howard, J.: Conformational changes during kinesin motility. *Curr Opin Cell Biol* 2001, 13:19-28.

Some members of this family transport molecular cargo along microtubules to the sites in the cell where they are needed. For example, some kinesins bind to vesicles and transport them along microtubules in axons. Several family members are mitotic kinesins, as they play roles in the reorganization of microtubules that establishes a bipolar mitotic spindle. The minus ends of the microtubules originate at the centrosomes, or spindle poles, whilst the plus ends bind to the kinetochore at the centromeric region of each chromosome. The mitotic spindle lines up the chromosomes at metaphase of mitosis and coordinates their movement apart and into individual daughter cells at anaphase and telophase (cytokinesis). See Alberts, B., Bray, D., Lewis, J., Raff, M., Roberts, K., and Watson, J. D., Molecular Biology of the Cell, 3$^{rd}$ edition, Chapter 18, The Mechanics of Cell Division, 1994, Garland Publishing, Inc. New York.

HsEg5 (homo sapiens Eg5) (Accession X85137; see Blangy, A., Lane H. A., d'Heron, P., Harper, M., Kress, M. and Nigg, E. A.: Phosphorylation by p34cdc2 regulates spindle association of human Eg5, a kinesin-related motor essential for bipolar spindle formation in vivo. *Cell* 1995, 83(7): 1159-1169) or, KSP (kinesin spindle protein), is a mitotic kinesin whose homologs in many organisms have been shown to be required for centrosome separation in the prophase of mitosis, and for the assembly of a bipolar mitotic spindle. For a review see Kashina, A. S., Rogers, G. C., and Scholey, J. M.: The bimC family of kinesins: essential bipolar mitotic motors driving centrosome separation. *Biochem Biophys Acta* 1997, 1357: 257-271. Eg5 forms a tetrameric motor, and it is thought to cross-link microtubules and participate in their bundling (Walczak, C. E., Vemos, I., Mitchison, T. J., Karsenti, E., and Heald, R.: A model for the proposed roles of different microtubule-based motor proteins in establishing spindle bipolarity. *Curr Biol* 1998, 8:903-913). Several reports have indicated that inhibition of Eg5 function leads to metaphase block in which cells display monastral spindles. Recently an Eg5 inhibitor called monastrol was isolated in a cell-based screen for mitotic blockers (Mayer, T. U., Kapoor, T. M., Haggarty, S. J., King, R. W., Schreiber, S. L., and Mitchison, T. J.: Small molecule inhibitor of mitotic spindle bipolarity identified in a phenotype-based screen. *Science* 1999, 286: 971-974).

Monastrol treatment was shown to be specific for Eg5 over kinesin heavy chain, another closely related motor with different functions (Mayer et al., 1999). Monastrol blocks the release of ADP (adenosine 5'-diphosphate) from the Eg5 motor (Maliga, Z., Kapoor, T. M., and Mitchison, T. J.: Evidence that monastrol is an allosteric inhibitor of the mitotic kinesin Eg5. *Chem & Biol* 2002, 9: 989-996 and DeBonis, S., Simorre, J.-P., Crevel, I., Lebeau, L, Skoufias, D. A., Blangy, A., Ebel, C., Gans, P., Cross, R., Hackney, D. D., Wade, R. H., and Kozielski, F.: Interaction of the mitotic inhibitor monastrol with human kinesin Eg5. *Biochemistry* 2003, 42: 338-349) an important step in the catalytic cycle of kinesin motor proteins (for review, see Sablin, 2000; Schief and Howard, 2001). Treatment with monastrol was shown to be reversible and to activate the mitotic spindle checkpoint which stops the progress of the cell division cycle until all the DNA is in place for appropriate division to occur (Kapoor, T. M., Mayer, T. U., Coughlin, M. L., and Mitchison, T. J.: Probing spindle assembly mechanisms with monastrol, a small molecule inhibitor of the mitotic kinesin, Eg5. *J Cell Biol* 2000, 150(5): 975-988). Recent reports also indicate that inhibitors of Eg5 lead to apoptosis of treated cells and are effective against several tumor cell lines and tumor models (Mayer et al., 1999).

Although Eg5 is thought to be necessary for mitosis in all cells, one report indicates that it is over-expressed in tumor cells (International Patent Application WO 01/31335), suggesting that they may be particularly sensitive to its inhibition. Eg5 is not present on the microtubules of interphase cells, and is targeted to microtubules by phosphorylation at an early point in mitosis (Blangy et al., 1995). See also; Sawin, K. E. and Mitchison, T. J.: Mutations in the kinesin-like protein Eg5 disrupting localization to the mitotic spindle. *Proc Natl Acad Sci USA* 1995, 92(10): 4289-4293, thus monastrol has no detectable effect on microtubule arrays in interphase cells (Mayer et al., 1999). Another report suggests that Eg5 is involved in neuronal development in the mouse, but it disappears from neurons soon after birth, and thus Eg5 inhibition may not produce the peripheral neuropathy associated with treatment with paclitaxel and other anti-microtubule drugs (Ferhat, L., Expression of the mitotic motor protein Eg5 in postmitotic neurons: implications for neuronal development. *J Neurosci* 1998, 18(19): 7822-7835). Herein we describe the isolation of a class of specific and potent inhibitors of Eg5, expected to be useful in the treatment of neoplastic disease.

Certain pyrimidones have recently been described as being inhibitors of KSP (WO 03/094839, WO 03/099211, WO 03/050122, WO 03/050064, WO 03/049679, WO 03/049527, WO 04/078758, WO 04/106492 and WO 04/111058).

In accordance with the present invention, the present inventors have discovered novel chemical compounds which possess Eg5 inhibitory activity and are accordingly useful for their anti-cell-proliferation (such as anti-cancer) activity and are therefore useful in methods of treatment of the human or animal body.

SUMMARY OF THE INVENTION

An enantiomer of a compound of formula (I):

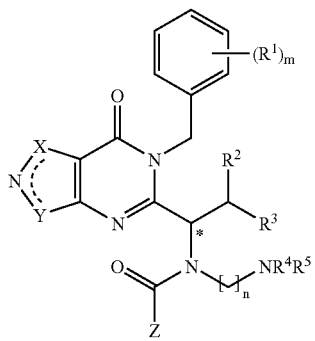

I including a pharmaceutically acceptable salt or an in vivo hydrolysable ester thereof, wherein:

X is selected from —C(CH$_3$)— or —S— provided that when X is —S— then Y is —C(CH$_3$)—;

Y is selected from —C(CH$_3$)— or —O— or —S— provided that when Y is —C(CH$_3$)— then X is not —C(CH$_3$)—;

m is 0 or 1;

R$^1$ is F when m is 1;

R$^2$ and R$^3$ are independently selected from H or C$_{1-3}$alkyl; wherein if both R$^2$ and R$^3$ are selected from C$_{1-3}$alkyl they are identical;

n is 2 or 3;

R$^4$ and R$^5$ are independently selected from H or C$_{1-3}$alkyl;

Z is optionally substituted phenyl, or optionally substituted benzothiophene wherein the number of optional substituents is 1 or 2 and each is independently selected from F, Cl, Br, CH$_3$ or CH$_2$CH$_3$; and "*" represents a chiral center;

wherein said enantiomer is substantially free of the other enantiomer; and wherein the optical rotation of the enantiomer, when said enantiomer is dissolved at a concentration of 1 mg/ml in methanol, at 20.0° C. measured at 589 nM is (+).

The invention encompasses stereoisomers, enantiomers, in vivo-hydrolysable precursors and pharmaceutically-acceptable salts of compounds of formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

DETAILED DESCRIPTION OF THE INVENTION

In a first embodiment, the present invention provides an enantiomer of a novel compound having structural formula (I):

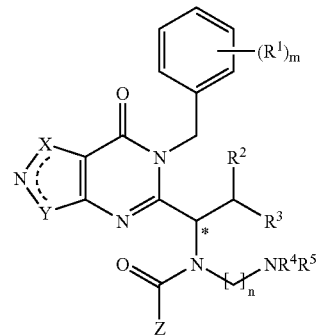

I including a pharmaceutically acceptable salt or an in vivo hydrolysable ester thereof, wherein:

X is selected from —C(CH$_3$)— or —S— provided that when X is —S— then Y is —C(CH$_3$)—;

Y is selected from —C(CH$_3$)— or —O— or —S— provided that when Y is —C(CH$_3$)— then X is not —C(CH$_3$)—;

m is 0 or 1;

R$^1$ is F when m is 1;

R$^2$ and R$^3$ are independently selected from H or C$_{1-3}$alkyl;

wherein if both R$^2$ and R$^3$ are selected from C$_{1-3}$alkyl they are identical;

n is 2 or 3;

R$^4$ and R$^5$ are independently selected from H or C$_{1-3}$alkyl;

Z is optionally substituted phenyl, or optionally substituted benzothiophene wherein the number of optional substituents is 1 or 2 and each is independently selected from F, Cl, Br, CH$_3$ or CH$_2$CH$_3$; and "*" represents a chiral center;

wherein said enantiomer is substantially free of the other enantiomer; and wherein the optical rotation of the enantiomer, when said enantiomer is dissolved at a concentration of 1 mg/ml in methanol, at 20.0° C. measured at 589 nM is (+).

In a further aspect of the invention there is provided a compound of formula (I) having an optical rotation of (+):

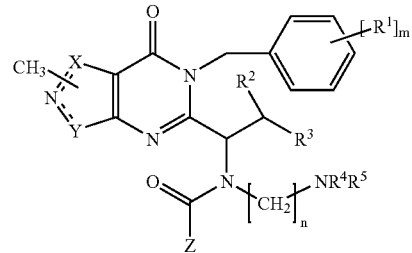

I including a pharmaceutically acceptable salt or an in vivo hydrolysable ester thereof, wherein:

X is selected from C or S provided that when X is S then Y is C;

Y is selected from C or O or S provided that when Y is C then X is not C;

m is 0 or 1;

R$^1$ is F when m is 1;

R$^2$ and R$^3$ are independently selected from H or C$_{1-3}$alkyl;

n is 2 or 3;

R$^4$ and R$^5$ are independently selected from H or C$_{1-3}$alkyl;

Z is optionally substituted phenyl, or optionally substituted benzothiophene wherein the number of substituents is 1 or 2 and each is independently selected from F, Cl, Br, CH$_3$ or CH$_2$CH$_3$.

In another embodiment, the present invention provides an (R) enantiomer of formula (Ia):

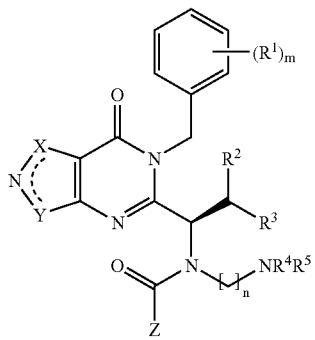

Ia including a pharmaceutically acceptable salt or an in vivo hydrolysable ester thereof, wherein:

X is selected from —C(CH$_3$)— or —S— provided that when X is —S— then Y is —C(CH$_3$)—;

Y is selected from —C(CH$_3$)— or —O— or —S— provided that when Y is —C(CH$_3$)— then X is not —C(CH$_3$)—;

m is 0 or 1;

R$^1$ is F when m is 1;

R$^2$ and R$^3$ are independently selected from H or C$_{1-3}$alkyl; wherein if both R$^2$ and R$^3$ are selected from C$_{1-3}$alkyl they are identical;

n is 2 or 3;

R$^4$ and R$^5$ are independently selected from H or C$_{1-3}$alkyl;

Z is optionally substituted phenyl, or optionally substituted benzothiophene wherein the number of optional substituents is 1 or 2 and each is independently selected from F, Cl, Br, CH$_3$ or CH$_2$CH$_3$;

wherein said enantiomer is substantially free of the (S) enantiomer.

In another embodiment, the present invention provides an (S) enantiomer of formula (Ib):

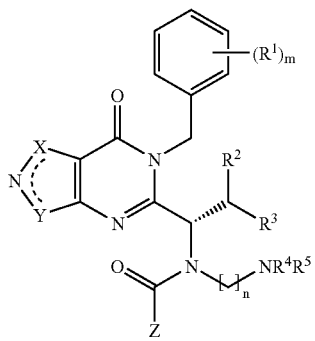

Ib including a pharmaceutically acceptable salt or an in vivo hydrolysable ester thereof, wherein:

X is selected from —C(CH$_3$)— or —S— provided that when X is —S— then Y is —C(CH$_3$)—;

Y is selected from —C(CH$_3$)— or —O— or —S— provided that when Y is —C(CH$_3$)— then X is not —C(CH$_3$)—;

m is 0 or 1;

R$^1$ is F when m is 1;

R$^2$ and R$^3$ are independently selected from H or C$_{1-3}$alkyl; wherein if both R$^2$ and R$^3$ are selected from C$_{1-3}$alkyl they are identical;

n is 2 or 3;

R$^4$ and R$^5$ are independently selected from H or C$_{1-3}$alkyl;

Z is optionally substituted phenyl, or optionally substituted benzothiophene wherein the number of optional substituents is 1 or 2 and each is independently selected from F, Cl, Br, CH$_3$ or CH$_2$CH$_3$.

wherein said enantiomer is substantially free of the (R) enantiomer.

In formula (I) the dotted line represents a single or a double bond—the bond between the nitrogen and whichever of X and Y is C is double, the other bond is a single bond.

In an additional embodiment, the present invention provides an enantiomer of a compound of formula (I) wherein X is —C(CH$_3$)— or a pharmaceutically acceptable salt or an in vivo hydrolysable ester thereof.

In an additional embodiment, the present invention provides an enantiomer of a compound of formula (I) wherein X is —S— or a pharmaceutically acceptable salt or an in vivo hydrolysable ester thereof.

In an additional embodiment, the present invention provides an enantiomer of a compound of formula (I) wherein Y is —C(CH$_3$)— or a pharmaceutically acceptable salt or an in vivo hydrolysable ester thereof.

In an additional embodiment, the present invention provides an enantiomer of a compound of formula (I) wherein Y is —S— or a pharmaceutically acceptable salt or an in vivo hydrolysable ester thereof.

In an additional embodiment, the present invention provides an enantiomer of a compound of formula (I) wherein Y is —O— or a pharmaceutically acceptable salt or an in vivo hydrolysable ester thereof.

In an additional embodiment, the present invention provides an enantiomer of a compound of formula (I) wherein Y is —S— and X is —C(CH$_3$)— or a pharmaceutically acceptable salt or an in vivo hydrolysable ester thereof.

In an additional embodiment, the present invention provides an enantiomer of a compound of formula (I) wherein Y is —O— and X is —C(CH$_3$)— or a pharmaceutically acceptable salt or an in vivo hydrolysable ester thereof.

In an additional embodiment, the present invention provides an enantiomer of a compound of formula (I) wherein Y is —C(CH$_3$)— and X is —S— or a pharmaceutically acceptable salt or an in vivo hydrolysable ester thereof.

In an additional embodiment, the present invention provides an enantiomer of a compound of formula (I) wherein m is 0 or a pharmaceutically acceptable salt or an in vivo hydrolysable ester thereof.

In an additional embodiment, the present invention provides an enantiomer of a compound of formula (I) wherein m is 1 or a pharmaceutically acceptable salt or an in vivo hydrolysable ester thereof.

In an additional embodiment, the present invention provides an enantiomer of a compound of formula (I) wherein R$^2$ is H or a pharmaceutically acceptable salt or an in vivo hydrolysable ester thereof.

In an additional embodiment, the present invention provides an enantiomer of a compound of formula (I) wherein $R^2$ is methyl or a pharmaceutically acceptable salt or an in vivo hydrolysable ester thereof.

In an additional embodiment, the present invention provides an enantiomer of a compound of formula (I) wherein $R^2$ is ethyl or a pharmaceutically acceptable salt or an in vivo hydrolysable ester thereof.

In an additional embodiment, the present invention provides an enantiomer of a compound of formula (I) wherein $R^2$ is propyl or a pharmaceutically acceptable salt or an in vivo hydrolysable ester thereof.

In an additional embodiment, the present invention provides an enantiomer of a compound of formula (I) wherein $R^2$ is isopropyl or a pharmaceutically acceptable salt or an in vivo hydrolysable ester thereof.

In an additional embodiment, the present invention provides an enantiomer of a compound of formula (I) wherein $R^3$ is methyl or a pharmaceutically acceptable salt or an in vivo hydrolysable ester thereof.

In an additional embodiment, the present invention provides an enantiomer of a compound of formula (I) wherein $R^3$ is ethyl or a pharmaceutically acceptable salt or an in vivo hydrolysable ester thereof.

In an additional embodiment, the present invention provides an enantiomer of a compound of formula (I) wherein $R^3$ is propyl or a pharmaceutically acceptable salt or an in vivo hydrolysable ester thereof.

In an additional embodiment, the present invention provides an enantiomer of a compound of formula (I) wherein $R^3$ is isopropyl or a pharmaceutically acceptable salt or an in vivo hydrolysable ester thereof.

In an additional embodiment, the present invention provides an enantiomer of a compound of formula (I) wherein $R^2$ is H and $R^3$ is methyl or a pharmaceutically acceptable salt or an in vivo hydrolysable ester thereof.

In an additional embodiment, the present invention provides an enantiomer of a compound of formula (I) wherein $R^2$ and $R^3$ are methyl or a pharmaceutically acceptable salt or an in vivo hydrolysable ester thereof.

In an additional embodiment, the present invention provides an enantiomer of a compound of formula (I) wherein n is 2 or a pharmaceutically acceptable salt or an in vivo hydrolysable ester thereof.

In an additional embodiment, the present invention provides an enantiomer of a compound of formula (I) wherein n is 3 or a pharmaceutically acceptable salt or an in vivo hydrolysable ester thereof.

In an additional embodiment, the present invention provides an enantiomer of a compound of formula (I) wherein $R^3$ is H or a pharmaceutically acceptable salt or an in vivo hydrolysable ester thereof.

In an additional embodiment, the present invention provides an enantiomer of a compound of formula (I) wherein $R^4$ is H or a pharmaceutically acceptable salt or an in vivo hydrolysable ester thereof.

In an additional embodiment, the present invention provides an enantiomer of a compound of formula (I) wherein $R^4$ is methyl or a pharmaceutically acceptable salt or an in vivo hydrolysable ester thereof.

In an additional embodiment, the present invention provides an enantiomer of a compound of formula (I) wherein $R^4$ is ethyl or a pharmaceutically acceptable salt or an in vivo hydrolysable ester thereof.

In an additional embodiment, the present invention provides an enantiomer of a compound of formula (I) wherein $R^4$ is propyl or a pharmaceutically acceptable salt or an in vivo hydrolysable ester thereof.

In an additional embodiment, the present invention provides an enantiomer of a compound of formula (I) wherein $R^4$ is isopropyl or a pharmaceutically acceptable salt or an in vivo hydrolysable ester thereof.

In an additional embodiment, the present invention provides an enantiomer of a compound of formula (I) wherein $R^5$ is H or a pharmaceutically acceptable salt or an in vivo hydrolysable ester thereof.

In an additional embodiment, the present invention provides an enantiomer of a compound of formula (I) wherein $R^5$ is methyl or a pharmaceutically acceptable salt or an in vivo hydrolysable ester thereof.

In an additional embodiment, the present invention provides an enantiomer of a compound of formula (I) wherein $R^5$ is ethyl or a pharmaceutically acceptable salt or an in vivo hydrolysable ester thereof.

In an additional embodiment, the present invention provides an enantiomer of a compound of formula (I) wherein $R^5$ is propyl or a pharmaceutically acceptable salt or an in vivo hydrolysable ester thereof.

In an additional embodiment, the present invention provides an enantiomer of a compound of formula (I) wherein $R^5$ is isopropyl or a pharmaceutically acceptable salt or an in vivo hydrolysable ester thereof.

In an additional embodiment, the present invention provides an enantiomer of a compound of formula (I) wherein $R^4$ and $R^5$ are both H or both methyl, or $R^4$ is H and $R^5$ is isopropyl or a pharmaceutically acceptable salt or an in vivo hydrolysable ester thereof.

In an additional embodiment, the present invention provides an enantiomer of a compound of formula (I) wherein Z is optionally substituted phenyl or a pharmaceutically acceptable salt or an in vivo hydrolysable ester thereof.

In an additional embodiment, the present invention provides an enantiomer of a compound of formula (I) wherein Z is optionally substituted benzothiophene or a pharmaceutically acceptable salt or an in vivo hydrolysable ester thereof.

In an additional embodiment, the present invention provides an enantiomer of a compound of formula (I) wherein Z is 4-methylphenyl or a pharmaceutically acceptable salt or an in vivo hydrolysable ester thereof.

In an additional embodiment, the present invention provides an enantiomer of a compound of formula (I) wherein Z is benzothiophen-2-yl or a pharmaceutically acceptable salt or an in vivo hydrolysable ester thereof.

In an additional embodiment, the present invention provides an enantiomer of a compound of formula (I) wherein Z is 4-chlorophenyl or a pharmaceutically acceptable salt or an in vivo hydrolysable ester thereof.

In an additional embodiment, the present invention provides an enantiomer of a compound of formula (I) wherein Z is 4-bromophenyl or a pharmaceutically acceptable salt or an in vivo hydrolysable ester thereof.

In an additional embodiment, the present invention provides an enantiomer of a compound of formula (I) wherein Z is 4-methyl-3-fluorophenyl or a pharmaceutically acceptable salt or an in vivo hydrolysable ester thereof.

In an additional embodiment, the present invention provides an enantiomer of a compound of formula (I) wherein Z is 2,3-dichlorophenyl or a pharmaceutically acceptable salt or an in vivo hydrolysable ester thereof.

In an additional embodiment, the present invention provides an enantiomer of a compound of formula (I) wherein Z is 4-methylphenyl, benzothiophen-2-yl, 4-chlorophenyl, 4-bromophenyl, 4-methyl-3-fluorophenyl or 2,3-dichlorophenyl or a pharmaceutically acceptable salt or an in vivo hydrolysable ester thereof.

Particular values of variable groups are as follows. Such values may be used where appropriate with any of the definitions, claims or embodiments defined hereinbefore or hereinafter.

X is —C(CH$_3$)—.
X is S.
Y is C.
Y is S.
Y is O.
Y is —S— and X is —C(CH$_3$)—.
Y is —O— and X is —C(CH$_3$)—.
Y is —C(CH$_3$)— and X is —S—.
m is 0.
m is 1.
R$^2$ is H.
R$^2$ is methyl.
R$^2$ is ethyl.
R$^2$ is propyl.
R$^2$ is isopropyl.
R$^3$ is methyl.
R$^3$ is ethyl.
R$^3$ is propyl.
R$^3$ is isopropyl.
R$^2$ is H and R$^3$ is methyl.
R$^2$ and R$^3$ are methyl.
n is 2.
n is 3.
R$^3$ is H.
R$^4$ is H.
R$^4$ methyl.
R$^4$ is ethyl.
R$^4$ is propyl.
R$^4$ is isopropyl.
R$^5$ is H.
R$^5$ is methyl.
R$^5$ is ethyl.
R$^5$ is propyl.
R$^5$ is isopropyl.
R$^4$ and R$^5$ are both H or both methyl, or R$^4$ is H and R$^5$ is isopropyl.
Z is optionally substituted phenyl.
Z is optionally substituted benzothiophene.
Z is 4-methylphenyl.
Z is benzothiophen-2-yl.
Z is 4-chlorophenyl.
Z is 4-bromophenyl.
Z is 4-methyl-3-fluorophenyl.
Z is 2,3-dichlorophenyl.
Z is 4-methylphenyl, benzothiophen-2-yl, 4-chlorophenyl, 4-bromophenyl, 4-methyl-3-fluorophenyl or 2,3-dichlorophenyl.

In a further aspect of the invention there is provided an enantiomer of a compound of formula (I) (as depicted above) including a pharmaceutically acceptable salt or an in vivo hydrolysable ester thereof, wherein:

X is selected from —C(CH$_3$)— or —S— provided that when X is —S— then Y is —C(CH$_3$)—;
Y is selected from —C(CH$_3$)— or —O— or —S— provided that when Y is —C(CH$_3$)— then X is not —C(CH$_3$)—;
m is 0 or 1;
R$^1$ is F when m is 1;
one of R$^2$ and R$^3$ is H and the other is methyl or both R$^2$ and R$^3$ are methyl;
n is 2 or 3;
R$^4$ and R$^5$ are independently selected from H or C$_{1-3}$alkyl;
Z is 4-methylphenyl, benzothiophen-2-yl, 4-chlorophenyl, 4-bromophenyl, 4-methyl-3-fluorophenyl or 2,3-dichlorophenyl; and
"*" represents a chiral center;

wherein said enantiomer is substantially free of the other enantiomer; and wherein the optical rotation of the enantiomer, when said enantiomer is dissolved at a concentration of 1 mg/ml in methanol, at 20.0° C. measured at 589 nM is (+).

In a further aspect of the invention there is provided an (R) enantiomer of a compound of formula (Ia) (as depicted above) including a pharmaceutically acceptable salt or an in vivo hydrolysable ester thereof, wherein:

X is selected from —C(CH$_3$)— or —S— provided that when X is —S— then Y is —C(CH$_3$)—;
Y is selected from —C(CH$_3$)— or —O— or —S— provided that when Y is —C(CH$_3$)— then X is not —C(CH$_3$)—;
m is 0 or 1;
R$^1$ is F when m is 1;
one of R$^2$ and R$^3$ is H and the other is methyl or both R$^2$ and R$^3$ are methyl;
n is 2 or 3;
R$^4$ and R$^5$ are independently selected from H or C$_{1-3}$alkyl; and
Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (S) enantiomer.

In a further aspect of the invention there is provided an (S) enantiomer of a compound of formula (Ib) (as depicted above) including a pharmaceutically acceptable salt or an in vivo hydrolysable ester thereof, wherein:

X is selected from —C(CH$_3$)— or —S— provided that when X is —S— then Y is —C(CH$_3$)—;
Y is selected from —C(CH$_3$)— or —O— or —S— provided that when Y is —C(CH$_3$)— then X is not —C(CH$_3$)—;
m is 0 or 1;
R$^1$ is F when m is 1;
one of R$^2$ and R$^3$ is H and the other is methyl or both R$^2$ and R$^3$ are methyl;
n is 2 or 3;
R$^4$ and R$^5$ are independently selected from H or C$_{1-3}$alkyl; and
Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (R) enantiomer.

In a further aspect of the invention there is provided an enantiomer of a compound of formula (I) (as depicted above) including a pharmaceutically acceptable salt or an in vivo hydrolysable ester thereof, wherein:

Y is —S— and X is —C(CH$_3$)—;
m is 0 or 1;
R$^1$ is F when m is 1;
one of R$^2$ and R$^3$ is H and the other is methyl or both R$^2$ and R$^3$ are methyl;

n is 2 or 3;

$R^4$ and $R^5$ are independently selected from H or $C_{1-3}$alkyl;

Z is 4-methylphenyl, benzothiophen-2-yl, 4-chlorophenyl, 4-bromophenyl, 4-methyl-3-fluorophenyl or 2,3-dichlorophenyl; and "*" represents a chiral center;

wherein said enantiomer is substantially free of the other enantiomer; and wherein the optical rotation of the enantiomer, when said enantiomer is dissolved at a concentration of 1 mg/ml in methanol, at 20.0° C. measured at 589 nM is (+).

In a further aspect of the invention there is provided an (R) enantiomer of a compound of formula (Ia) (as depicted above) including a pharmaceutically acceptable salt or an in vivo hydrolysable ester thereof, wherein:

Y is —S— and X is —C(CH$_3$)—;

m is 0 or 1;

$R^1$ is F when m is 1;

one of $R^2$ and $R^3$ is H and the other is methyl or both $R^2$ and $R^3$ are methyl;

n is 2 or 3;

$R^4$ and $R^5$ are independently selected from H or $C_{1-3}$alkyl; and

Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (S) enantiomer.

In a further aspect of the invention there is provided an (S) enantiomer of a compound of formula (Ib) (as depicted above) including a pharmaceutically acceptable salt or an in vivo hydrolysable ester thereof, wherein:

Y is —S— and X is —C(CH$_3$)—;

m is 0 or 1;

$R^1$ is F when m is 1;

one of $R^2$ and $R^3$ is H and the other is methyl or both $R^2$ and $R^3$ are methyl;

n is 2 or 3;

$R^4$ and $R^5$ are independently selected from H or $C_{1-3}$alkyl; and

Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (R) enantiomer.

In a further aspect of the invention there is provided an enantiomer of a compound of formula (I) (as depicted above) including a pharmaceutically acceptable salt or an in vivo hydrolysable ester thereof, wherein:

Y is —O— and X is —C(CH$_3$)—;

m is 0 or 1;

$R^1$ is F when m is 1;

one of $R^2$ and $R^3$ is H and the other is methyl or both $R^2$ and $R^3$ are methyl;

n is 2 or 3;

$R^4$ and $R^5$ are independently selected from H or $C_{1-3}$alkyl;

Z is 4-methylphenyl, benzothiophen-2-yl, 4-chlorophenyl, 4-bromophenyl, 4-methyl-3-fluorophenyl or 2,3-dichlorophenyl; and "*" represents a chiral center;

wherein said enantiomer is substantially free of the other enantiomer; and wherein the optical rotation of the enantiomer, when said enantiomer is dissolved at a concentration of 1 mg/ml in methanol, at 20.0° C. measured at 589 nM is (+).

In a further aspect of the invention there is provided an (R) enantiomer of a compound of formula (Ia) (as depicted above) including a pharmaceutically acceptable salt or an in vivo hydrolysable ester thereof, wherein:

Y is —O— and X is —C(CH$_3$)—;

m is 0 or 1;

$R^1$ is F when m is 1;

one of $R^2$ and $R^3$ is H and the other is methyl or both $R^2$ and $R^3$ are methyl;

n is 2 or 3;

$R^4$ and $R^5$ are independently selected from H or $C_{1-3}$alkyl; and

Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (S) enantiomer.

In a further aspect of the invention there is provided an (S) enantiomer of a compound of formula (Ib) (as depicted above) including a pharmaceutically acceptable salt or an in vivo hydrolysable ester thereof, wherein:

Y is —O— and X is —C(CH$_3$)—;

m is 0 or 1;

$R^1$ is F when m is 1;

one of $R^2$ and $R^3$ is H and the other is methyl or both $R^2$ and $R^3$ are methyl;

n is 2 or 3;

$R^4$ and $R^5$ are independently selected from H or $C_{1-3}$alkyl; and

Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (R) enantiomer.

In a further aspect of the invention there is provided an enantiomer of a compound of formula (I) (as depicted above) including a pharmaceutically acceptable salt or an in vivo hydrolysable ester thereof, wherein:

Y is —C(CH$_3$)— and X is —S—;

m is 0 or 1;

$R^1$ is F when m is 1;

one of $R^2$ and $R^3$ is H and the other is methyl or both $R^2$ and $R^3$ are methyl;

n is 2 or 3;

$R^4$ and $R^5$ are independently selected from H or $C_{1-3}$alkyl;

Z is 4-methylphenyl, benzothiophen-2-yl, 4-chlorophenyl, 4-bromophenyl, 4-methyl-3-fluorophenyl or 2,3-dichlorophenyl; and "*" represents a chiral center;

wherein said enantiomer is substantially free of the other enantiomer; and wherein the optical rotation of the enantiomer, when said enantiomer is dissolved at a concentration of 1 mg/ml in methanol, at 20.0° C. measured at 589 nM is (+).

In a further aspect of the invention there is provided an (R) enantiomer of a compound of formula (Ia) (as depicted above) including a pharmaceutically acceptable salt or an in vivo hydrolysable ester thereof, wherein:
Y is —C(CH$_3$)— and X is —S—;
m is 0 or 1;
R$^1$ is F when m is 1;
one of R$^2$ and R$^3$ is H and the other is methyl or both R$^2$ and R$^3$ are methyl;
n is 2 or 3;
R$^4$ and R$^5$ are independently selected from H or C$_{1-3}$alkyl; and
Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (S) enantiomer.

In a further aspect of the invention there is provided an (S) enantiomer of a compound of formula (Ib) (as depicted above) including a pharmaceutically acceptable salt or an in vivo hydrolysable ester thereof, wherein:
Y is —C(CH$_3$)— and X is —S—;
m is 0 or 1;
R$^1$ is F when m is 1;
one of R$^2$ and R$^3$ is H and the other is methyl or both R$^2$ and R$^3$ are methyl;
n is 2 or 3;
R$^4$ and R$^5$ are independently selected from H or C$_{1-3}$alkyl; and
Z is 4-methylphenyl, benzothiophen-2-yl, 4-chlorophenyl, 4-bromophenyl, 4-methyl-3-fluorophenyl or 2,3-dichlorophenyl;

wherein said enantiomer is substantially free of the (R) enantiomer.

In a further aspect of the invention there is provided a compound of formula (I) or a pharmaceutically acceptable salt thereof.

In an additional embodiment, the present invention provides a compound of formula (I) or a pharmaceutically acceptable salt or an in vivo hydrolysable ester thereof selected from:

(+) N-(3-Amino-propyl)-N-[1-(5-benzyl-3-methyl-4-oxo-4,5-dihydro-isothiazolo[5,4-d]pyrimidin-6-yl)-propyl]-4-methyl-benzamide hydrogen chloride;

(+) N-(3-Amino-propyl)-N-{1-[5-(4-fluoro-benzyl)-3-methyl-4-oxo-4,5-dihydro-isothiazolo[5,4-d]pyrimidin-6-yl]-propyl}-4-methyl-benzamide hydrogen chloride;

(+) N-(3-Amino-propyl)-N-{1-[5-(3-fluoro-benzyl)-3-methyl-4-oxo-4,5-dihydro-isothiazolo[5,4-d]pyrimidin-6-yl]-propyl}-4-methyl-benzamide hydrogen chloride;

(+) N-(3-Amino-propyl)-N-[1-(5-benzyl-3-methyl-4-oxo-4,5-dihydro-isothiazolo[5,4-d]pyrimidin-6-yl)-propyl]-4-bromo-benzamide hydrogen chloride;

(+) N-(3-Amino-propyl)-N-[1-(5-benzyl-3-methyl-4-oxo-4,5-dihydro-isothiazolo[5,4-d]pyrimidin-6-yl)-propyl]-4-chloro-benzamide hydrogen chloride;

(+) N-(3-Amino-propyl)-N-[1-(5-benzyl-3-methyl-4-oxo-4,5-dihydro-isothiazolo[5,4-d]pyrimidin-6-yl)-propyl]-3-fluoro-4-methyl-benzamide hydrogen chloride;

(+) N-(3-Amino-propyl)-N-[1-(5-benzyl-3-methyl-4-oxo-4,5-dihydro-isothiazolo[5,4-d]pyrimidin-6-yl)-propyl]-2,3-dichloro-benzamide hydrogen chloride;

(+) Benzo[b]thiophene-2-carboxylic acid (3-amino-propyl)-[1-(5-benzyl-3-methyl-4-oxo-4,5-dihydro-isothiazolo[5,4-d]pyrimidin-6-yl)-propyl]amide hydrogen chloride;

(+) N-(2-Amino-ethyl)-N-[1-(5-benzyl-3-methyl-4-oxo-4,5-dihydro-isothiazolo[5,4-d]pyrimidin-6-yl)-propyl]-4-methyl-benzamide;

(+) N-[1-(5-Benzyl-3-methyl-4-oxo-4,5-dihydro-isothiazolo[5,4-d]pyrimidin-6-yl)-propyl]-N-(3-dimethylamino-propyl)-4-methyl-benzamide;

(+) N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide;

(+) N-(3-Amino-propyl)-N-[1-(5-benzyl-3-methyl-4-oxo-4,5-dihydro-isoxazolo[5,4-d]pyrimidin-6-yl)-propyl]-4-methyl-benzamide hydrogen chloride;

(+) N-(3-Amino-propyl)-N-{1-[5-(4-fluoro-benzyl)-3-methyl-4-oxo-4,5-dihydro-isothiazolo[5,4-d]pyrimidin-6-yl]-2-methyl-propyl}-4-methyl-benzamide hydrogen chloride;

(+) N-(3-Amino-propyl)-N-[1-(5-benzyl-3-methyl-4-oxo-4,5-dihydro-isothiazolo[5,4-d]pyrimidin-6-yl)-2-methyl-propyl]-4-methyl-benzamide hydrogen chloride;

(+) N-(3-Amino-propyl)-N-{1-[5-(3-fluoro-benzyl)-3-methyl-4-oxo-4,5-dihydro-isothiazolo[5,4-d]pyrimidin-6-yl]-2-methyl-propyl}-4-methyl-benzamide hydrogen chloride;

(+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-bromo-benzamide hydrogen chloride;

(+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-methyl-benzamide hydrogen chloride;

(+) N-(2-Amino-ethyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide hydrogen chloride;

(+) N-(3-Amino-propyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide hydrogen chloride;

(+) N-(3-Amino-propyl)-N-[1-(5-benzyl-3-methyl-4-oxo-4,5-dihydro-isothiazolo[5,4-d]pyrimidin-6-yl)-2-methyl-propyl]-4-bromo-benzamide hydrogen chloride;

(+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-methyl-benzamide;

(+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-bromo-benzamide;

(+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-3-fluoro-4-methyl-benzamide;

(+) N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide hydrogen chloride;

(+) N-(3-Amino-propyl)-N-{1-[5-(4-fluoro-benzyl)-3-methyl-4-oxo-4,5-dihydro-isoxazolo[5,4-d]pyrimidin-6-yl]-2-methyl-propyl}-4-methyl-benzamide hydrogen chloride;

(+) N-(3-Amino-propyl)-N-{1-[5-(3-fluoro-benzyl)-3-methyl-4-oxo-4,5-dihydro-isoxazolo[5,4-d]pyrimidin-6-yl]-2-methyl-propyl}-4-methyl-benzamide hydrogen chloride;

(+) N-(3-Amino-propyl)-N-[1-(6-benzyl-3-methyl-7-oxo-6,7-dihydro-isothiazolo[4,5-d]pyrimidin-5-yl)-propyl]-4-methyl-benzamide.

In an additional embodiment, the present invention provides a compound of formula (I) or a pharmaceutically acceptable salt or an in vivo hydrolysable ester thereof selected from:

(+) N-(3-Amino-propyl)-N-[1-(5-benzyl-3-methyl-4-oxo-4,5-dihydro-isothiazolo[5,4-d]pyrimidin-6-yl)-propyl]-4-methyl-benzamide;

(+) N-(3-Amino-propyl)-N-{1-[5-(4-fluoro-benzyl)-3-methyl-4-oxo-4,5-dihydro-isothiazolo[5,4-d]pyrimidin-6-yl]-propyl}-4-methyl-benzamide;

(+) N-(3-Amino-propyl)-N-{1-[5-(3-fluoro-benzyl)-3-methyl-4-oxo-4,5-dihydro-isothiazolo[5,4-d]pyrimidin-6-yl]-propyl}-4-methyl-benzamide;

(+) N-(3-Amino-propyl)-N-[1-(5-benzyl-3-methyl-4-oxo-4,5-dihydro-isothiazolo[5,4-d]pyrimidin-6-yl)-propyl]-4-bromo-benzamide;

(+) N-(3-Amino-propyl)-N-[1-(5-benzyl-3-methyl-4-oxo-4,5-dihydro-isothiazolo[5,4-d]pyrimidin-6-yl)-propyl]-4-chloro-benzamide;

(+) N-(3-Amino-propyl)-N-[1-(5-benzyl-3-methyl-4-oxo-4,5-dihydro-isothiazolo[5,4-d]pyrimidin-6-yl)-propyl]-3-fluoro-4-methyl-benzamide;

(+) N-(3-Amino-propyl)-N-[1-(5-benzyl-3-methyl-4-oxo-4,5-dihydro-isothiazolo[5,4-d]pyrimidin-6-yl)-propyl]-2,3-dichloro-benzamide;

(+) Benzo[b]thiophene-2-carboxylic acid (3-amino-propyl)-[1-(5-benzyl-3-methyl-4-oxo-4,5-dihydro-isothiazolo[5,4-d]pyrimidin-6-yl)-propyl]amide;

(+) N-(2-Amino-ethyl)-N-[1-(5-benzyl-3-methyl-4-oxo-4,5-dihydro-isothiazolo[5,4-d]pyrimidin-6-yl)-propyl]-4-methyl-benzamide;

(+) N-[1-(5-Benzyl-3-methyl-4-oxo-4,5-dihydro-isothiazolo[5,4-d]pyrimidin-6-yl)-propyl]-N-(3-dimethylamino-propyl)-4-methyl-benzamide;

(+) N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide;

(+) N-(3-Amino-propyl)-N-[1-(5-benzyl-3-methyl-4-oxo-4,5-dihydro-isoxazolo[5,4-d]pyrimidin-6-yl)-propyl]-4-methyl-benzamide;

(+) N-(3-Amino-propyl)-N-{1-[5-(4-fluoro-benzyl)-3-methyl-4-oxo-4,5-dihydro-isothiazolo[5,4-d]pyrimidin-6-yl]-2-methyl-propyl}-4-methyl-benzamide;

(+) N-(3-Amino-propyl)-N-[1-(5-benzyl-3-methyl-4-oxo-4,5-dihydro-isothiazolo[5,4-d]pyrimidin-6-yl)-2-methyl-propyl]-4-methyl-benzamide;

(+) N-(3-Amino-propyl)-N-{1-[5-(3-fluoro-benzyl)-3-methyl-4-oxo-4,5-dihydro-isothiazolo[5,4-d]pyrimidin-6-yl]-2-methyl-propyl}-4-methyl-benzamide;

(+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-bromo-benzamide;

(+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-methyl-benzamide;

(+) N-(2-Amino-ethyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide;

(+) N-(3-Amino-propyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide;

(+) N-(3-Amino-propyl)-N-[1-(5-benzyl-3-methyl-4-oxo-4,5-dihydro-isothiazolo[5,4-d]pyrimidin-6-yl)-2-methyl-propyl]-4-bromo-benzamide;

(+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-methyl-benzamide;

(+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-bromo-benzamide;

(+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-3-fluoro-4-methyl-benzamide;

(+) N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide;

(+) N-(3-Amino-propyl)-N-{1-[5-(4-fluoro-benzyl)-3-methyl-4-oxo-4,5-dihydro-isoxazolo[5,4-d]pyrimidin-6-yl]-2-methyl-propyl}-4-methyl-benzamide;

(+) N-(3-Amino-propyl)-N-{1-[5-(3-fluoro-benzyl)-3-methyl-4-oxo-4,5-dihydro-isoxazolo[5,4-d]pyrimidin-6-yl]-2-methyl-propyl}-4-methyl-benzamide; or (+) N-(3-Amino-propyl)-N-[1-(6-benzyl-3-methyl-7-oxo-6,7-dihydro-isothiazolo[4,5-d]pyrimidin-5-yl)-propyl]-4-methyl-benzamide.

In an additional embodiment, the present invention provides an enantiomer of formula (Ia) or a pharmaceutically acceptable salt or an in vivo hydrolysable ester thereof selected from:

(R) N-(3-Amino-propyl)-N-[1-(5-benzyl-3-methyl-4-oxo-4,5-dihydro-isothiazolo[5,4-d]pyrimidin-6-yl)-propyl]-4-methyl-benzamide;

(R) N-(3-Amino-propyl)-N-{1-[5-(4-fluoro-benzyl)-3-methyl-4-oxo-4,5-dihydro-isothiazolo[5,4-d]pyrimidin-6-yl]-propyl}-4-methyl-benzamide;

(R) N-(3-Amino-propyl)-N-{1-[5-(3-fluoro-benzyl)-3-methyl-4-oxo-4,5-dihydro-isothiazolo[5,4-d]pyrimidin-6-yl]-propyl}-4-methyl-benzamide;

(R) N-(3-Amino-propyl)-N-[1-(5-benzyl-3-methyl-4-oxo-4,5-dihydro-isothiazolo[5,4-d]pyrimidin-6-yl)-propyl]-4-bromo-benzamide;

(R) N-(3-Amino-propyl)-N-[1-(5-benzyl-3-methyl-4-oxo-4,5-dihydro-isothiazolo[5,4-d]pyrimidin-6-yl)-propyl]-4-chloro-benzamide;

(R) N-(3-Amino-propyl)-N-[1-(5-benzyl-3-methyl-4-oxo-4,5-dihydro-isothiazolo[5,4-d]pyrimidin-6-yl)-propyl]-3-fluoro-4-methyl-benzamide;

(R) N-(3-Amino-propyl)-N-[1-(5-benzyl-3-methyl-4-oxo-4,5-dihydro-isothiazolo[5,4-d]pyrimidin-6-yl)-propyl]-2,3-dichloro-benzamide;

(R) Benzo[b]thiophene-2-carboxylic acid (3-amino-propyl)-[1-(5-benzyl-3-methyl-4-oxo-4,5-dihydro-isothiazolo[5,4-d]pyrimidin-6-yl)-propyl]amide;

(R) N-(2-Amino-ethyl)-N-[1-(5-benzyl-3-methyl-4-oxo-4,5-dihydro-isothiazolo[5,4-d]pyrimidin-6-yl)-propyl]-4-methyl-benzamide;

(R) N-[1-(5-Benzyl-3-methyl-4-oxo-4,5-dihydro-isothiazolo[5,4-d]pyrimidin-6-yl)-propyl]-N-(3-dimethylamino-propyl)-4-methyl-benzamide;

(R) N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide;

(R) N-(3-Amino-propyl)-N-[1-(5-benzyl-3-methyl-4-oxo-4,5-dihydro-isoxazolo[5,4-d]pyrimidin-6-yl)-propyl]-4-methyl-benzamide;

(R) N-(3-Amino-propyl)-N-{1-[5-(4-fluoro-benzyl)-3-methyl-4-oxo-4,5-dihydro-isothiazolo[5,4-d]pyrimidin-6-yl]-2-methyl-propyl}-4-methyl-benzamide;

(R) N-(3-Amino-propyl)-N-[1-(5-benzyl-3-methyl-4-oxo-4,5-dihydro-isothiazolo[5,4-d]pyrimidin-6-yl)-2-methyl-propyl]-4-methyl-benzamide;

(R) N-(3-Amino-propyl)-N-{1-[5-(3-fluoro-benzyl)-3-methyl-4-oxo-4,5-dihydro-isothiazolo[5,4-d]pyrimidin-6-yl]-2-methyl-propyl}-4-methyl-benzamide;

(R) N-(2-Amino-ethyl)-N-[1-(5-benzyl-3-methyl-4-oxo-4,5-dihydro-isothiazolo[5,4-d]pyrimidin-6-yl)-2-methyl-propyl]-4-bromo-benzamide;

(R) N-(2-Amino-ethyl)-N-[1-(5-benzyl-3-methyl-4-oxo-4,5-dihydro-isothiazolo[5,4-d]pyrimidin-6-yl)-2-methyl-propyl]-4-methyl-benzamide;
(R) N-(2-Amino-ethyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide;
(R) N-(3-Amino-propyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide;
(R) N-(3-Amino-propyl)-N-[1-(5-benzyl-3-methyl-4-oxo-4,5-dihydro-isothiazolo[5,4-d]pyrimidin-6-yl)-2-methyl-propyl]-4-bromo-benzamide;
(R) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-methyl-benzamide;
(R) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-bromo-benzamide;
(R) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-3-fluoro-4-methyl-benzamide;
(R) N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide;
(R) N-(3-Amino-propyl)-N-{1-[5-(4-fluoro-benzyl)-3-methyl-4-oxo-4,5-dihydro-isoxazolo[5,4-d]pyrimidin-6-yl]-2-methyl-propyl}-4-methyl-benzamide;
(R) N-(3-Amino-propyl)-N-{1-[5-(3-fluoro-benzyl)-3-methyl-4-oxo-4,5-dihydro-isoxazolo[5,4-d]pyrimidin-6-yl]-2-methyl-propyl}-4-methyl-benzamide; or
(R) N-(3-Amino-propyl)-N-[1-(6-benzyl-3-methyl-7-oxo-6,7-dihydro-isothiazolo[4,5-d]pyrimidin-5-yl)-propyl]-4-methyl-benzamide.

In an additional embodiment, the present invention provides an enantiomer of formula (Ib) or a pharmaceutically acceptable salt or an in vivo hydrolysable ester thereof selected from:

(S) N-(3-Amino-propyl)-N-[1-(5-benzyl-3-methyl-4-oxo-4,5-dihydro-isothiazolo[5,4-d]pyrimidin-6-yl)-propyl]-4-methyl-benzamide;
(S) N-(3-Amino-propyl)-N-{1-[5-(4-fluoro-benzyl)-3-methyl-4-oxo-4,5-dihydro-isothiazolo[5,4-d]pyrimidin-6-yl]-propyl}-4-methyl-benzamide;
(S) N-(3-Amino-propyl)-N-{1-[5-(3-fluoro-benzyl)-3-methyl-4-oxo-4,5-dihydro-isothiazolo[5,4-d]pyrimidin-6-yl]-propyl}-4-methyl-benzamide;
(S) N-(3-Amino-propyl)-N-[1-(5-benzyl-3-methyl-4-oxo-4,5-dihydro-isothiazolo[5,4-d]pyrimidin-6-yl)-propyl]-4-bromo-benzamide;
(S) N-(3-Amino-propyl)-N-[1-(5-benzyl-3-methyl-4-oxo-4,5-dihydro-isothiazolo[5,4-d]pyrimidin-6-yl)-propyl]-4-chloro-benzamide;
(S) N-(3-Amino-propyl)-N-[1-(5-benzyl-3-methyl-4-oxo-4,5-dihydro-isothiazolo[5,4-d]pyrimidin-6-yl)-propyl]-3-fluoro-4-methyl-benzamide;
(S) N-(3-Amino-propyl)-N-[1-(5-benzyl-3-methyl-4-oxo-4,5-dihydro-isothiazolo[5,4-d]pyrimidin-6-yl)-propyl]-2,3-dichloro-benzamide;
(S) Benzo[b]thiophene-2-carboxylic acid (3-amino-propyl)-[1-(5-benzyl-3-methyl-4-oxo-4,5-dihydro-isothiazolo[5,4-d]pyrimidin-6-yl)-propyl]amide;
(S) N-(2-Amino-ethyl)-N-[1-(5-benzyl-3-methyl-4-oxo-4,5-dihydro-isothiazolo[5,4-d]pyrimidin-6-yl)-propyl]-4-methyl-benzamide;
(S) N-[1-(5-Benzyl-3-methyl-4-oxo-4,5-dihydro-isothiazolo[5,4-d]pyrimidin-6-yl)-propyl]-N-(3-dimethylamino-propyl)-4-methyl-benzamide;
(S) N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide;
(S) N-(3-Amino-propyl)-N-[1-(5-benzyl-3-methyl-4-oxo-4,5-dihydro-isoxazolo[5,4-d]pyrimidin-6-yl)-propyl]-4-methyl-benzamide;
(S) N-(3-Amino-propyl)-N-{1-[5-(4-fluoro-benzyl)-3-methyl-4-oxo-4,5-dihydro-isothiazolo[5,4-d]pyrimidin-6-yl]-2-methyl-propyl}-4-methyl-benzamide;
(S) N-(3-Amino-propyl)-N-[1-(5-benzyl-3-methyl-4-oxo-4,5-dihydro-isothiazolo[5,4-d]pyrimidin-6-yl)-2-methyl-propyl]-4-methyl-benzamide;
(S) N-(3-Amino-propyl)-N-{1-[5-(3-fluoro-benzyl)-3-methyl-4-oxo-4,5-dihydro-isothiazolo[5,4-d]pyrimidin-6-yl]-2-methyl-propyl}-4-methyl-benzamide;
(S) N-(2-Amino-ethyl)-N-[1-(5-benzyl-3-methyl-4-oxo-4,5-dihydro-isothiazolo[5,4-d]pyrimidin-6-yl)-2-methyl-propyl]-4-bromo-benzamide;
(S) N-(2-Amino-ethyl)-N-[1-(5-benzyl-3-methyl-4-oxo-4,5-dihydro-isothiazolo[5,4-d]pyrimidin-6-yl)-2-methyl-propyl]-4-methyl-benzamide;
(S) N-(2-Amino-ethyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide;
(S) N-(3-Amino-propyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide;
(S) N-(3-Amino-propyl)-N-[1-(5-benzyl-3-methyl-4-oxo-4,5-dihydro-isothiazolo[5,4-d]pyrimidin-6-yl)-2-methyl-propyl]-4-bromo-benzamide;
(S) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-methyl-benzamide;
(S) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-bromo-benzamide;
(S) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-3-fluoro-4-methyl-benzamide;
(S) N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide;
(S) N-(3-Amino-propyl)-N-{1-[5-(4-fluoro-benzyl)-3-methyl-4-oxo-4,5-dihydro-isoxazolo[5,4-d]pyrimidin-6-yl]-2-methyl-propyl}-4-methyl-benzamide;
(S) N-(3-Amino-propyl)-N-{1-[5-(3-fluoro-benzyl)-3-methyl-4-oxo-4,5-dihydro-isoxazolo[5,4-d]pyrimidin-6-yl]-2-methyl-propyl}-4-methyl-benzamide; or
(S) N-(3-Amino-propyl)-N-[1-(6-benzyl-3-methyl-7-oxo-6,7-dihydro-isothiazolo[4,5-d]pyrimidin-5-yl)-propyl]-4-methyl-benzamide.

A particular embodiment of the invention refers to a compound of formula (I), (Ia) or (Ib) or a pharmaceutically acceptable salt thereof.

A compound of formula (I) or a pharmaceutically acceptable salt or an in vivo hydrolysable ester thereof, which is substantially free of its corresponding (−) enantiomer.

The term "substantially free" refers to less than 10% of the other isomer, more particularly less than 5%, in particular less than 2%, more particularly less than 1%, particularly less then 0.5%, in particular less than 0.2%.

A compound of formula (I) or a pharmaceutically acceptable salt or an in vivo hydrolysable ester thereof having no more than about 1% w/w of the corresponding (−) enantiomer.

A compound of formula (I) or a pharmaceutically acceptable salt or an in vivo hydrolysable ester thereof having no more than 1% w/w of the corresponding (−) enantiomer.

A compound of formula (I) or a pharmaceutically acceptable salt or an in vivo hydrolysable ester thereof having no more than about 2% w/w of the corresponding (−) enantiomer.

A compound of formula (I) or a pharmaceutically acceptable salt or an in vivo hydrolysable ester thereof having no more than 2% w/w of the corresponding (−) enantiomer.

In an additional embodiment, the present invention provides a compound of formula (I) or a pharmaceutically acceptable salt or an in vivo hydrolysable ester thereof for use as a medicament.

Herein where the use of a compound of formula (I), or a method of treatment comprising administering a compound of formula (I), or the use of a pharmaceutical composition comprising a compound of formula (I), is referred to it is to be understood that "a compound of formula (I)" refers to (i) an enantiomer of a compound of formula (I); or (ii) an (R) enantiomer of formula (Ia); or (iii) an (S) enantiomer of formula (Ib).

According to a further aspect of the invention there is provided the use of a compound of the formula (I), or a pharmaceutically acceptable salt or an in vivo hydrolysable thereof, as defined hereinbefore in the manufacture of a medicament for use in the production of an Eg5 inhibitory effect in a warm-blooded animal such as man.

According to a further aspect of the invention there is provided the use of a compound of the formula (I), or a pharmaceutically acceptable salt or an in vivo hydrolysable thereof, as defined hereinbefore in the manufacture of a medicament for use in the production of an anti-proliferative effect in a warm-blooded animal such as man.

According to this aspect of the invention there is provided the use of a compound of the formula (I), or a pharmaceutically acceptable salt or an in vivo hydrolysable thereof, as defined hereinbefore in the manufacture of a medicament for use in the production of an anti-cancer effect in a warm-blooded animal such as man.

According to a further feature of the invention, there is provided the use of a compound of the formula (I), or a pharmaceutically acceptable salt or an in vivo hydrolysable thereof, as defined herein before in the manufacture of a medicament for use in the treatment of carcinomas of the brain, breast, ovary, lung, colon and prostate, multiple myeloma leukemias, lymphomas, tumors of the central and peripheral nervous system, melanoma, fibrosarcoma, Ewing's sarcoma and osteosarcoma.

In an additional embodiment, the present invention provides the use of a compound of formula (I) or a pharmaceutically acceptable salt or an in vivo hydrolysable ester thereof, in the manufacture of a medicament for the treatment or prophylaxis of disorders associated with cancer.

According to a further feature of this aspect of the invention there is provided a method for producing an Eg5 inhibitory effect in a warm-blooded animal, such as man, in need of such treatment which comprises administering to said animal an effective amount of a compound of formula (I), or a pharmaceutically acceptable salt or an in vivo hydrolysable thereof, as defined above.

According to a further feature of this aspect of the invention there is provided a method of producing an anti-proliferative effect in a warm-blooded animal, such as man, in need of such treatment which comprises administering to said animal an effective amount of a compound of formula (I), or a pharmaceutically acceptable salt or an in vivo hydrolysable thereof, as defined above.

According to a further feature of this aspect of the invention there is provided a method for producing an anti-cancer effect in a warm-blooded animal, such as man, in need of such treatment which comprises administering to said animal an effective amount of a compound of formula (I), or a pharmaceutically acceptable salt or an in vivo hydrolysable thereof, as defined above.

In an additional embodiment, the present invention provides a method for the prophylaxis treatment of cancers associated with comprising administering to a human in need of such treatment a therapeutically effective amount of a compound of formula (I).

In a further embodiment the present invention provides a method for the prophylaxis treatment of cancers associated with comprising administering to a human in need of such treatment a therapeutically effective amount of a compound of formula (I) or a pharmaceutically acceptable salt or an in vivo hydrolysable thereof.

In an additional embodiment, the present invention provides a method of producing a cell cycle inhibitory (anti-cell-proliferation) effect in a warm-blooded animal, such as man, in need of such treatment with comprises administering to said animal an effective amount of a compound of formula (I).

In a further embodiment the present invention provides a method of producing a cell cycle inhibitory (anti-cell-proliferation) effect in a warm-blooded animal, such as man, in need of such treatment with comprises administering to said animal an effective amount of a compound of formula (I) or a pharmaceutically acceptable salt or an in vivo hydrolysable thereof.

In an additional embodiment, the present invention provides a method for the treatment of cancer comprising administering to a human a therapeutically effective amount of a compound of formula (I) or a pharmaceutically acceptable salt or an in vivo hydrolysable ester thereof.

In a further embodiment the present invention provides a method for the treatment of cancer comprising administering to a human a therapeutically effective amount of a compound of formula (I) or a pharmaceutically acceptable salt or an in vivo hydrolysable thereof.

In an additional embodiment, the present invention provides a method for the treatment of breast cancer, colorectal cancer, ovarian cancer, lung (non small cell) cancer, malignant brain tumors, sarcomas, melanoma and lymphoma by administring a compound of formula (I) or a pharmaceutically acceptable salt or an in vivo hydrolysable ester thereof.

In a further embodiment the present invention provides a method for the treatment of breast cancer, colorectal cancer, ovarian cancer, lung (non small cell) cancer, malignant brain tumors, sarcomas, melanoma and lymphoma by administering a compound of formula (I) or a pharmaceutically acceptable salt or an in vivo hydrolysable thereof.

According to an additional feature of this aspect of the invention there is provided a method of treating carcinomas of the brain, breast, ovary, lung, colon and prostate, multiple myeloma leukemias, lymphomas, tumors of the central and peripheral nervous system, melanoma, fibrosarcoma, Ewing's sarcoma and osteosarcoma, in a warm-blooded animal, such as man, in need of such treatment which comprises administering to said animal an effective amount of a compound of formula (I) or a pharmaceutically acceptable salt or an in vivo hydrolysable thereof as defined herein before.

In an additional embodiment, the present invention provides a method for the treatment of cancer by administering to a human a compound of formula (I) or a pharmaceutically acceptable salt or an in vivo hydrolysable ester thereof and an anti-tumor agent.

In an additional embodiment, the present invention provides a pharmaceutical composition comprising a compound of formula (I) or a pharmaceutically acceptable salt or an in vivo hydrolysable ester thereof together with at least one pharmaceutically acceptable carrier, diluent or excipient.

In a further aspect of the invention there is provided a pharmaceutical composition which comprises a compound of the formula (I), or a pharmaceutically acceptable salt or an in vivo hydrolysable thereof, as defined herein before in association with a pharmaceutically-acceptable diluent or carrier for use in the production of an Eg5 inhibitory effect in a warm-blooded animal such as man.

In a further aspect of the invention there is provided a pharmaceutical composition which comprises a compound of the formula (I), or a pharmaceutically acceptable salt or an in vivo hydrolysable thereof, as defined herein before in association with a pharmaceutically-acceptable diluent or carrier for use in the production of an anti-proliferative effect in a warm-blooded animal such as man.

In a further aspect of the invention there is provided a pharmaceutical composition which comprises a compound of the formula (I), or a pharmaceutically acceptable salt or an in vivo hydrolysable thereof, as defined herein before in association with a pharmaceutically-acceptable diluent or carrier for use in the production of an anti-cancer effect in a warm-blooded animal such as man.

In a further aspect of the invention there is provided a pharmaceutical composition which comprises a compound of the formula (I), or a pharmaceutically acceptable salt or an in vivo hydrolysable thereof, as defined herein before in association with a pharmaceutically-acceptable diluent or carrier for use in the treatment of carcinomas of the brain, breast, ovary, lung, colon and prostate, multiple myeloma leukemias, lymphomas, tumors of the central and peripheral nervous system, melanoma, fibrosarcoma, Ewing's sarcoma and osteosarcoma in a warm-blooded animal such as man.

According to a further aspect of the invention there is provided the use of a compound of the formula (I), or a pharmaceutically acceptable salt or an in vivo hydrolysable thereof, as defined hereinbefore in the production of an Eg5 inhibitory effect in a warm-blooded animal such as man.

According to a further aspect of the invention there is provided the use of a compound of the formula (I), or a pharmaceutically acceptable salt or an in vivo hydrolysable thereof, as defined hereinbefore for use in the production of an anti-proliferative effect in a warm-blooded animal such as man.

According to this aspect of the invention there is provided the use of a compound of the formula (I), or a pharmaceutically acceptable salt or an in vivo hydrolysable thereof, as defined hereinbefore for use in the production of an anti-cancer effect in a warm-blooded animal such as man.

According to a further feature of the invention, there is provided the use of a compound of the formula (I), or a pharmaceutically acceptable salt or an in vivo hydrolysable thereof, as defined herein before for use in the treatment of carcinomas of the brain, breast, ovary, lung, colon and prostate, multiple myeloma leukemias, lymphomas, tumors of the central and peripheral nervous system, melanoma, fibrosarcoma, Ewing's sarcoma and osteosarcoma.

In a further embodiment the present invention provides the use of a compound of formula (I) or a pharmaceutically acceptable salt or an in vivo hydrolysable thereof, for the treatment or prophylaxis of disorders associated with cancer.

The definitions set forth in this section are intended to clarify terms used throughout this application. The term "herein" means the entire application.

The term "$C_{m\text{-}n}$" or "$C_{m\text{-}n}$ group" used alone or as a prefix, refers to any group having m to n carbon atoms.

The term "hydrocarbon" used alone or as a suffix or prefix, refers to any structure comprising only carbon and hydrogen atoms up to 14 carbon atoms.

The term "hydrocarbon radical" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising, unless otherwise indicated, 1 to about 12 carbon atoms. Unless otherwise specified, "alkyl" includes both saturated alkyl and unsaturated alkyl. Particularly "alkyl" refers to saturated alkyl. Particularly "$C_{1\text{-}3}$alkyl" refers to methyl, ethyl, propyl or isopropyl.

The term "five-membered" used as prefix refers to a group having a ring that contains five ring atoms.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

"RT" or "rt" means room temperature.

When any variable (e.g., $R^1$, $R^4$ etc.) occurs more than one time in any constituent or formula for a compound, its definition at each occurrence is independent of its definition at every other occurrence. Thus, for example, if a group is shown to be substituted with 0-3 $R^1$, then said group may optionally be substituted with 0, 1, 2 or 3 $R^1$ groups and $R^1$ at each occurrence is selected independently from the definition of $R^1$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like. The pharmaceutically acceptable salts of the invention also include salts prepared with one of the following acids benzene sulfonic acid, fumaric acid, methanesulfonic acid, naphthalene-1,5-disulfonic acid, naphthalene-2-sulfonic acid or L-tartaric acid.

Thus in one aspect of the invention there is provided a compound of the invention, particularly one of the Examples described herein, as a pharmaceutically acceptable salt, particularly a benzene sulfonic acid, fumaric acid, methanesulfonic acid, naphthalene-1,5-disulfonic acid, naphthalene-2-sulfonic acid or L-tartaric acid salt.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

As used herein, "in vivo hydrolysable ester" means an in vivo hydrolysable (or cleavable) ester of a compound of the formula (I) that contains a carboxy or a hydroxy group. For example amino acid esters, $C_{1-6}$alkoxymethyl esters like methoxymethyl; $C_{1-6}$alkanoyloxymethyl esters like pivaloyloxymethyl; $C_{3-8}$cycloalkoxycarbonyloxy $C_{1-6}$alkyl esters like 1-cyclohexylcarbonyloxyethyl, acetoxymethoxy, or phosphoramidic cyclic esters.

All chemical names were generated using a software system known as AutoNom Name accessed through ISIS draw.

Combinations

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, oxaliplatin, cyclophosphamide, nitrogen mustard, melphalan, chlorambucil, busulphan, temozolomide and nitrosoureas); antimetabolites (for example gemcitabine and antifolates such as fluoropyrimidines like 5-fluorouracil and tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere) polokinase inhibitors; and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function or inhibitors of SRC kinase (like 4-(6-chloro-2,3-methylene-dioxyanilino)-7-[2-(4-methylpiperazin-1-yl)ethoxy]-5-tetrahydropyran-4-yloxyqyuinazoline (AZD0530; International Patent Application WO 01/94341) and N-(2-chloro-6-methylphenyl)-2-{6-[4-(2-hydroxyethyl) piperazin-1-yl]-2-methylpyrimidin-4-ylamino}thiazole-5-carboxamide (dasatinib, BMS-354825; *J. Med. Chem.*, 2004, 47, 6658-6661))or antibodies to Heparanase);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [Erbitux, C225]), Ras/Raf signalling inhibitors such as farnesyl transferase inhibitors(for example sorafenib (BAY 43-9006) and tipifarnib), tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), for example inhibitors of the platelet-derived growth factor family such as imatinib, and for example inhibitors of the hepatocyte growth factor family, c-kit inhibitors, abl kinase inhibitors, IGF receptor (insulin-like growth factor) kinase inhibitors and inhibitors of cell signalling through MEK, AKT and/or P13K kinases;

(v) antiangiogenic agents such as those which inhibit the effects of vascular endothelial growth factor, (for example the anti-vascular endothelial cell growth factor antibody bevacizumab [Avastin™], and VEGF receptor tyrosine kinase inhibitors such as those disclosed in International patent applications WO 97/22596, WO 97/30035, WO 97/32856, WO 98/13354, 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SUI 1248 (sunitinib; WO 01/60814)) and compounds that work by other mechanisms (for example linomide, inhibitors of integrin αvβ3 function and angiostatin), ang1 and 2 inhibitors;

(vi) vascular damaging agents such as Combretastatin A4 and compounds disclosed in International patent applications WO 99/02166, WO 00/40529, WO 00/41669, WO 01/92224, WO 02/04434 and WO 02/08213, anti bcl2;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

x) cell cycle agents such as aurora kinase inhibitors (for example PH739358, VX-680, MLN8054, R763, MP235, MP529, VX-528, AX39459 and the specific examples mentioned in WO02/00649, WO03/055491, WO2004/058752, WO2004/058781, WO2004/058782, WO2004/094410, WO2004/105764, WO2004/113324 which are incorporated herein by reference), and cyclin dependent kinase inhibitors such as CDK2 and/or CDK4 inhibitors (for example the specific examples of WO01/14375, WO01/72717, WO02/04429, WO02/20512, WO02/66481, WO02/096887, WO03/076435, WO03/076436, WO03/076434, WO03/076433, WO04/101549 and WO04/101564 which are incorporated herein by reference); and xi) cytotoxic agents such as gemcitibine, topoisomerase I inhibitors (adriamycin, etoposide) and topoisomerase II inhibitors.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

In a further aspect of the present invention there is provided a compound of formula (I) or a pharmaceutically acceptable salt or an in vivo hydrolysable ester thereof in combination with simultaneous, sequential or separate dosing of an anti-tumor agent or class selected from the list herein above.

Therefore in a further embodiment the present invention provides a method for the treatment of cancer by administering to a human a compound of formula (I) or a pharmaceutically acceptable salt or an in vivo hydrolysable ester thereof in combination with simultaneous, sequential or separate dosing of an anti-tumor agent or class selected from the list herein above.

In a further aspect of the present invention there is provided the use of a compound of formula (I) or a pharmaceutically acceptable salt or an in vivo hydrolysable ester thereof in combination with simultaneous, sequential or separate dosing of an anti-tumor agent or class selected from the list herein above for use in the manufacture of a medicament for use in the treatment of cancer.

In a further aspect of the present invention there is provided the use of a compound of formula (I) or a pharmaceutically acceptable salt or an in vivo hydrolysable ester thereof in combination with simultaneous, sequential or separate dosing of an anti-tumor agent or class selected from the list herein above for use in the treatment of cancer.

The anti-cancer treatment defined herein may also include one or more of the following categories of pharmaceutical agents:

i) an agent useful in the treatment of anemia, for example, a continuous eythropoiesis receptor activator (such as epoetin alfa);

ii) an agent useful in the treatment of neutropenia, for example, a hematopoietic growth factor which regulates the production and function of neutrophils such as a human granulocyte colony stimulating factor, (G-CSF), for example filgrastim; and iii) an anti-emetic agent to treat nausea or emesis, including acute, delayed, late-phase, and anticipatory emesis, which may result from the use of a compound of the present invention, alone or with radiation therapy, suitable examples of such anti emetic agents include neurokinin-1 receptor antagonists, 5H13 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid or Benecorten, an antidopaminergic, such as the phenothiazines (for example prochlorperazine, fluphenazine, thioridazine and mesoridazine), metoclopramide or dronabinol.

Such conjoint treatment may be achieved by way of the simultaneous, sequential or separate dosing of the individual components of the treatment. Such conjoint treatment employs the compounds of this invention within the dosage range described hereinbefore and the other pharmaceutically-active agent within its approved dosage range.

In a further aspect of the present invention there is provided a compound of formula (I) or a pharmaceutically acceptable salt or an in vivo hydrolysable ester thereof in combination with simultaneous, sequential or separate dosing of another pharmaceutical agent or class selected from the list herein above.

Therefore in a further embodiment the present invention provides a method for the treatment of cancer by administering to a human a compound of formula (I) or a pharmaceutically acceptable salt or an in vivo hydrolysable ester thereof in combination with simultaneous, sequential or separate dosing of another pharmaceutical agent or class selected from the list herein above.

In a further aspect of the present invention there is provided the use of a compound of formula (I) or a pharmaceutically acceptable salt or an in vivo hydrolysable ester thereof in combination with simultaneous, sequential or separate dosing of another pharmaceutical agent or class selected from the list herein above for use in the manufacture of a medicament for use in the treatment of cancer.

In a further aspect of the present invention there is provided the use of a compound of formula (I) or a pharmaceutically acceptable salt or an in vivo hydrolysable ester thereof in combination with simultaneous, sequential or separate dosing of another pharmaceutical agent or class selected from the list herein above for use in the treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of Eg5 in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

Formulations

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of infection is an amount sufficient to symptomatically relieve in a warm-blooded animal, particularly a human the symptoms of infection, to slow the progression of infection, or to reduce in patients with symptoms of infection the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

The starting materials for the Examples contained herein are either commercially available or are readily prepared by standard methods from known materials. For example the following reactions are illustrations but not limitations of the preparation of some of the starting materials and examples used herein.

All chiral purifications to separate the respective enantiomers were carried out using a Chiralpak AD column (dimensions 250×20 mm, 10μ column) with a flow rate of 20 ml/min unless otherwise stated. Approximate elution times may vary depending on the concentration of compound loaded. Chiral purification generally resulted in 99% purity of the (+) enantiomer.

The signal refers to the direction of rotation of polarized light at 670 nm as measured by an Advanced Laser Polarimeter (PDR-Chiral, Inc., Lake Park, Fla.) at ambient temperature in the solvent composition indicated (reference Liu Y. S., Yu T., Armstrong D. W., LC-GC 17 (1999), 946-957).

EXAMPLES

The invention will now be illustrated by the following non limiting examples in which, unless stated otherwise:
(i) temperatures are given in degrees Celsius (° C.); operations were carried out at room or ambient temperature, that is, at a temperature in the range of 18-30° C.;
(ii) organic solutions were dried over anhydrous sodium sulphate; evaporation of solvent was carried out using a rotary evaporator under reduced pressure (600-4000 Pascals; 4.5-30 mmHg) with a bath temperature of up to 60° C.;
(iii) in general, the course of reactions was followed by TLC or MS and reaction times are given for illustration only;
(iv) final products had satisfactory proton nuclear magnetic resonance (NMR) spectra and/or mass spectral data;
(v) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 400 MHz using deuterated chloroform (CDCl$_3$) as solvent unless otherwise indicated;
(vii) chemical symbols have their usual meanings; SI units and symbols are used;
(viii) solvent ratios are given in volume:volume (v/v) terms; and
(ix) mass spectra were run with an electron energy of 70 electron volts in the chemical ionization (CI) mode using a direct exposure probe; where indicated ionization was effected by electron impact (EI), fast atom bombardment (FAB), electrospray (ESP); or atmospheric pressure chemical ionization (APCI); values for m/z are given; generally, only ions which indicate the parent mass are reported;
(x) where a synthesis is described as being analogous to that described in a previous example the amounts used are the millimolar ratio equivalents to those used in the previous example;
(xi) the following abbreviations have been used:

| | |
|---|---|
| THF | tetrahydrofuran; |
| DMF | N,N-dimethylformamide; |
| EtOAc | ethyl acetate; |
| DCM | dichloromethane; and |
| DMSO | dimethylsulphoxide; and |

(xii) a Vigreux column is a glass tube with a series of indentations such that alternate sets of indentations point downward at an angle of 45 degree in order to promote the redistribution of liquid from the walls to the center of the column; The Vigreux column used herein is 150 mm long (between indents) with a 20 mm diameter and it was manufactured by Lab Glass.

Method 1

2-(1-Ethoxy-ethylidene)-malononitrile

Triethyl orthoacetate (97 g, 0.6 mol), malononitrile (33 g, 0.5 mol) and glacial acetic acid (1.5 g) were placed in a 1 L flask equipped with a stirrer, thermometer and a Vigreux column (20×1 in.) on top of which a distillation condenser was placed. The reaction mixture was heated and ethyl alcohol began to distill when the temperature of the reaction mixture was about 85-90° C. After about 40 min., the temperature of the reaction mixture reached 140° C. Then the reaction was concentrated in a rotary evaporator to remove the low-boiling materials and the residue was crystallized from absolute alcohol to yield the pure product (62.2 g, 91%) as a light yellow solid mp 91.6° C.

Method 2

(2E)-2-Cyano-3-ethoxybut-2-enethioamide 2-(1-Ethoxy-ethylidene)-malononitrile (method 1) (62 g, 0.45 mol) was dissolved in anhydrous benzene (800 mL) and 1 mL of triethylamine was added as catalyst. The mixture was stirred and hydrogen sulfide was bubbled into this solution for 40 min and a solid formed. The precipitated solid was filtered off and dried. The solid was recrystallized from absolute alcohol (100 mL) filtered and dried to isolate the pure (2E)-2-cyano-3-ethoxybut-2-enethioamide (19.3 g, 25%) as light brown crystals.

Method 3

(2E)-3-Amino-2-cyanobut-2-enethioamide (2E)-2-Cyano-3-ethoxybut-2-enethioamide (method 2) (19.2 g, 0.136 mol) was dissolved in a saturated solution of ammonia in methanol (500 mL) and stirred at r.t. overnight. The reaction mixture was concentrated and the residue was dissolved in hot water (600 mL) and the undissoved solid was filtered and dried to recover 6 g of the starting thiocrotonamide. The aqueous solution on standing overnight provided the pure (2E)-3-amino-2-cyanobut-2-enethioamide (6.85 g, 63%) as off-white crystals. $^1$H NMR (300 MHz, DMSO-d$_6$) δ 2.22 (s, 3H), 7.73 (bs, 1H), 8.53 (bs, 1H), 9.01 (bs, 1H), 11.60 (bs, 1H).

Method 4

5-Amino-3-methylisothiazole-4-carbonitrile

To a stirred solution of (2E)-3-amino-2-cyanobut-2-enethioamide (method 3) (6.83 g, 48.4 mmol) in methanol (300 mL) was added dropwise 13.6 mL (124 mmoL) of 30% hydrogen peroxide. The mixture was stirred at 60° C. for 4 h and evaporated to 60 mL in a rotary evaporator and cooled in an ice-bath. The crystallized product was filtered off and recrystallized from EtOAc to provide the pure product 5-amino-3-methylisothiazole-4-carbonitrile (5.41 g, 80%) as a white crystalline solid. $^1$H NMR (300 MHz, DMSO-$d_6$) δ 2.24 (s, 3H), 8.00 (bs, 2H).

Method 5

N-(4-Cyano-3-methyl-isothiazol-5-yl)-butyramide

To a solution of 5-amino-3-methylisothiazole-4-carbonitrile (method 4) (5.31 g, 38.2 mmol) in DCM (200 mL) at 0° C., NEt$_3$ (5 g, 50 mmol) was added followed by the dropwise addition of a solution of the butyryl chloride (4.88 g, 45.8 mmol) in DCM (50 mL). After the completion of the addition the reaction mixture was allowed to warm to r.t. and stirred overnight. The reaction mixture was washed with water (100 mL), 1N HCl (100 mL), brine (200 mL) and dried over Na$_2$SO$_4$. Concentration of the DCM layer provided the crude product which was triturated from DCM/hexanes (1/10) and filtered off to isolate the pure N-(4-cyano-3-methyl-isothiazol-5-yl)-butyramide (7.57 g, 95%) as an orange solid.

Method 6

5-Butyrylamino-3-methyl-isothiazole-4-carboxylic acid amide

To a solution of N-(4-cyano-3-methyl-isothiazol-5-yl)-butyramide (method 5) (4.18 g, 20 mmol) in 30% aqueous NH$_4$OH (250 mL), was added dropwise 100 mL of hydrogen peroxide at r.t. After the completion of the addition the reaction mixture was stirred at 60° C. overnight after which the TLC showed the complete disappearance of SM. The reaction mixture was cooled and extracted with chloroform (3×100 mL). The organic layer was dried (Na$_2$SO$_4$) and concentrated to get the pure 5-butyrylamino-3-methyl-isothiazole-4-carboxylic acid amide (2.9 g, 72%) as a white solid. $^1$H NMR (300 MHz) δ 1.03 (t, 3H), 1.79 (m, 2H), 2.54 (t, 3H), 2.69 (s, 3H), 5.97 (bs, 2H), 11.78 (bs, 1H).

Method 7

3-Methyl-6-propyl-5H-isothiazolo[5,4-d]pyrimidin-4-one

5-Butyrylamino-3-methyl-isothiazole-4-carboxylic acid amide (method 6) (1.9 g, 8.3 mmol) was suspended in 75 mL of 30% NH$_3$ and then was heated to 140° C. for 4 h in a pressure reactor. The mixture was cooled and neutralized to pH 8. The precipitated 3-methyl-6-propyl-5H-isothiazolo[5,4-d]pyrimidin-4-one was filtered off, washed with water (100 mL) and dried in vacuum oven at 40° C. overnight to get 800 mg (34%) of pure product. $^1$H NMR (300 MHz) δ 1.03 (t, 3H), 1.74 (m, 2H), 2.67 (t, 3H), 2.78 (s, 3H).

Method 8

5-Benzyl-3-methyl-6-propyl-5H-isothiazolo[5,4-d]pyrimidin-4-one

To a solution of 3-methyl-6-propyl-5H-isothiazolo[5,4-d]pyrimidin-4-one (method 7) (800 mg, 3.8 mmol) in 20 mL of anhydrous DMF was added 1.38 g (10 mmol) of anhydrous 10 K$_2$CO$_3$ followed by benzyl bromide (655 mg, 3.8 mmol) and the mixture was stirred at room temperature overnight. The TLC of the reaction mixture showed the complete disappearance of the SM. The reaction mixture was poured into ice cold water and extracted with EtOAc (3×100 mL). The combined extracts were washed with water (100 mL), brine (100 mL), dried (Na$_2$SO$_4$) and concentrated. The TLC and the $^1$H NMR showed the presence of two products N alkylated as well as O-alkylated products in a ratio of 1:1. The products were separated by column (silica gel, 116 g) chromatography using 10-20% EtOAc in hexanes. The desired N-alkylated product 5-benzyl-3-methyl-6-propyl-5H-isothiazolo[5,4-d]pyrimidin-4-one was isolated as white crystalline solid (369 mg, 32%). $^1$H NMR (300 MHz) δ 0.96 (t, 3H), 1.71-1.84 (m, 2H), 2.73 (t, 3H), 2.81 (s, 3H), 5.38 (s, 2H), 7.14-7.38 (m, 5H).

Methods 8a-8b

The following compounds were synthesized according to Method 8:

| Method # | Compound Name | m/z | Alkylating agent |
|---|---|---|---|
| 8a | 5-(4-Fluoro-benzyl)-3-methyl-6-propyl-5H-isothiazolo[5,4-d]pyrimidin-4-one | 318 (MH$^+$) | 4-fluorobenzyl bromide |
| 8b | 5-(3-Fluoro-benzyl)-3-methyl-6-propyl-5H-isothiazolo[5,4-d]pyrimidin-4-one | 318 (MH$^+$) | 3-fluorobenzyl bromide |

Method 9

5-Benzyl-6-(1-bromo-propyl)-3-methyl-5H-isothiazolo[5,4-d]pyrimidin-4-one

To a solution of 5-benzyl-3-methyl-6-propyl-5H-isothiazolo[5,4-d]pyrimidin-4-one (method 8) (369 mg, 1.23 mmol) and sodium acetate (1 g) in acetic acid (5 mL) at 100° C., a solution of the bromine (318 mg, 2 mmol) in acetic acid (10 mL) was added dropwise over a period of 20 minutes. The reaction mixture was cooled after the addition and the TLC (eluent 10% EtOAc in hexanes) and MS showed the complete disappearance of the SM and only the product. The reaction mixture was poured into ice water and extracted with EtOAc (3×60 mL) and the organic layers were combined and washed with 2% sodium thiosulfate solution (60 mL), water (100 mL), brine (100 mL) and dried over Na$_2$SO$_4$. Concentration of the organic layer provided the pure 5-benzyl-6-(1-bromo-propyl)-3-methyl-5H-isothiazolo[5,4-d]pyrimidin-4-one, (460 mg, 100%) as white crystalline solid. $^1$H NMR (300

MHz) δ 0.76 (t, 3H), 2.1-2.47 (m, 2H), 2.84 (s, 3H), 4.62 (t, 1H), 4.88 (d, 1H), 6.20 (d, 1H), 7.10-7.40 (m, 5H).

Methods 9a-9b

The following compounds were synthesized according to Method 9:

| Method # | Compound Name | m/z | SM |
|---|---|---|---|
| 9a | 6-(1-bromopropyl)-5-[(4-fluorophenyl)methyl]-3-methyl-isothiazolo[5,4-d]pyrimidin-4(5H)-one | 396, 398 (MH⁺) | Method 8a |
| 9b | 6-(1-bromopropyl)-5-[(3-fluorophenyl)methyl]-3-methyl-isothiazolo[5,4-d]pyrimidin-4(5H)-one | 396, 398 (MH⁺) | Method 8b |

Method 10

{3-[1-(5-Benzyl-3-methyl-4-oxo-4,5-dihydro-isothiazolo[5,4-d]pyrimidin-6-yl)-propylamino]-propyl}-carbamic acid tert-butyl ester To a solution of 5-benzyl-6-(1-bromo-propyl)-3-methyl-5H-isothiazolo[5,4-d]pyrimidin-4-one (method 9) (0.46 g, 1.22 mmol) in anhydrous ethanol (20 mL), was added tert-butyl 3-aminopropyl-carbamate (0.211 g, 1.22 mmol) followed by the addition of anhydrous diisopropylethylamine (0.258 g, 2 mmol) and the mixture was stirred at reflux for 16 hours. The TLC of the RM showed the complete disappearance of the starting bromide. The reaction mixture was poured into ice water (200 mL) and extracted with EtOAc (3×100 mL). The organic layer was washed with water (100 mL), brine (100 mL) and dried (Na₂SO₄). Concentration of the organic layer provided the crude product which was purified by column (silica gel) chromatography using 30-50% EtOAc in hexanes to isolate the pure amine {3-[1-(5-benzyl-3-methyl-4-oxo-4,5-dihydro-isothiazolo[5,4-d]pyrimidin-6-yl)-propylamino]-propyl}-carbamic acid tert-butyl ester (0.1 g, 17%) as a white foam. ¹H NMR (300 MHz) δ 0.95 (t, 3H), 1.33 (t, 2H), 1.42 (s, 9H), 1.49-1.51 (m, 2H), 1.87-1.99 (m, 1H), 2.35-2.45 (m, 1H), 2.83 (s, 3H), 2.92-3.20 (m, 2H), 3.64-3.70 (m, 1H), 4.98 (d, 1H), 5.17 (bs, 1H), 5.85 (d, 1H), 7.10-7.40 (m, 5H).

Methods 10a-10d

The following compounds were synthesized according to Method 10:

| Method # | Compound Name | m/z | SM | Amine |
|---|---|---|---|---|
| 10a | {3-({1-[5-(4-fluoro-benzyl)-3-methyl-4-oxo-4,5-dihydro-isothiazolo[5,4-d]pyrimidin-6-yl]-propyl}amino)-propyl}-carbamic acid tert-butyl ester | 490 (MH⁺) | Method 9a | tert-butyl 3-aminopropyl-carbamate |
| 10b | {3-({1-[5-(3-fluoro-benzyl)-3-methyl-4-oxo-4,5-dihydro-isothiazolo[5,4-d]pyrimidin-6-yl]-propyl}amino)-propyl}-carbamic acid tert-butyl ester | 490 (MH⁺) | Method 9b | tert-butyl 3-aminopropyl-carbamate |
| 10c | 5-Benzyl-6-[1-(3-dimethylamino-propyl-amino)-propyl]-3-methyl-5H-isothiazolo[5,4-d]pyrimidin-4-one | 400 (MH⁺) | Method 9 | N,N-Dimethylpropane-1,3-diamine |
| 10d | {2-[1-(5-Benzyl-3-methyl-4-oxo-4,5-dihydro-isothiazolo[5,4-d]pyrimidin-6-yl)-propyl-amino]-ethyl}-carbamic acid tert-butyl ester | 458 (MH⁺) | Method 9 | (2-Amino-ethyl)-carbamic acid tert-butyl ester |

Method 11

{3-[[1-(5-Benzyl-3-methyl-4-oxo-4,5-dihydro-isothiazolo[5,4-d]pyrimidin-6-yl)-propyl]-(4-methyl-benzoyl)-amino]-propyl}-carbamic acid tert-butyl ester To a solution of {3-[1-(5-benzyl-3-methyl-4-oxo-4,5-dihydro-isothiazolo[5,4-d]pyrimidin-6-yl)-propylamino]-propyl}-carbamic acid tert-butyl ester (method 10) (0.1 g, 0.21 mmol) and triethylamine (0.303 g, 3 mmol) in DCM (20 mL) at r.t. was added dropwise a solution of p-toluoyl chloride (0.1 g, 0.6 mmol) in DCM (10 mL). The resulting solution was stirred at r.t. for 30 min. after which the TLC showed the disappearance of the SM. The reaction mixture was diluted with DCM (60 mL) washed with satd. NaHCO₃ (100 mL), water (100 mL), brine (100 mL) and dried (Na₂SO₄). Concentration of the organic layer provided the crude product which was purified by column (silica gel) chromatography using 20-30% EtOAc in hexanes as eluent. Yield was 0.117 g (94%). m/z 590 (MH⁺).

Methods 11a-11i

The following compounds were synthesized according to Method 11:

| Method # | Compound Name | m/z | SM | Acylating agent |
|---|---|---|---|---|
| 11a | {3-[{1-[5-(4-Fluoro-benzyl)-3-methyl-4-oxo-4,5-dihydro-isothiazolo[5,4-d]pyrimidin-6-yl]-propyl}-(4-methyl-benzoyl)-amino]-propyl}-carbamic acid tert-butyl ester | 608 (MH⁺) | Method 10a | 4-methyl-benzoyl chloride |
| 11b | {3-[{1-[5-(3-Fluoro-benzyl)-3-methyl-4-oxo-4,5-dihydro-isothiazolo[5,4-d]pyrimidin-6-yl]-propyl}-(4-methyl-benzoyl)-amino]-propyl}-carbamic acid tert-butyl ester | 608 (MH⁺) | Method 10b | 4-methyl-benzoyl chloride |
| 11c | {3-[[1-(5-Benzyl-3-methyl-4-oxo-4,5-dihydro-isothiazolo[5,4-d]pyrimidin-6-yl)-propyl]-(4-chloro-benzoyl)-amino]-propyl}-carbamic acid tert-butyl ester | 610 (MH⁺) | Method 10 | 4-chloro-benzoyl chloride |

-continued

| Method # | Compound Name | m/z | SM | Acylating agent |
|---|---|---|---|---|
| 11d | {3-[[1-(5-Benzyl-3-methyl-4-oxo-4,5-dihydro-isothiazolo[5,4-d]pyrimidin-6-yl)-propyl]-(3-fluoro-4-methyl-benzoyl)-amino]-propyl}-carbamic acid tert-butyl ester | 608 (MH+) | Method 10 | 3-fluoro-4-methyl-benzoyl chloride |
| 11e | {3-[[1-(5-Benzyl-3-methyl-4-oxo-4,5-dihydro-isothiazolo[5,4-d]pyrimidin-6-yl)-propyl]-(2,3-dichloro-benzoyl)-amino]-propyl}-carbamic acid tert-butyl ester | 644, 645, 646 (MH+) | Method 10 | 2,3-dichloro-benzoyl chloride |
| 11f | (3-{(Benzo[b]thiophene-2-carbonyl)-[1-(5-benzyl-3-methyl-4-oxo-4,5-dihydro-isothiazolo[5,4-d]pyrimidin-6-yl)-propyl]-amino}-propyl)-carbamic acid tert-butyl ester | 632 (MH+) | Method 10 | 1-benzothiophene-2-carbonyl chloride |
| 11g | {3-[[1-(5-Benzyl-3-methyl-4-oxo-4,5-dihydro-isothiazolo[5,4-d]pyrimidin-6-yl)-propyl]-(4-bromo-benzoyl)-amino]-propyl}-carbamic acid tert-butyl ester | 654, 656 (MH+) | Method 10 | 4-bromo-benzoyl chloride |
| 11h | {2-[[1-(5-Benzyl-3-methyl-4-oxo-4,5-dihydro-isothiazolo[5,4-d]pyrimidin-6-yl)-propyl]-(4-methyl-benzoyl)-amino]-ethyl}-carbamic acid tert-butyl ester | 576 (MH+) | Method 10d | 4-methyl-benzoyl chloride |
| 11i | N-[1-(5-Benzyl-3-methyl-4-oxo-4,5-dihydro-isothiazolo[5,4-d]pyrimidin-6-yl)-propyl]-N-(3-dimethyl-amino-propyl)-4-methyl-benzamide | 518 (MH+) | Method 10c | 4-methyl-benzoyl chloride |

Method 12

Chiral purification of (+) (3-[[1-(5-Benzyl-3-methyl-4-oxo-4,5-dihydro-isothiazolo[5,4-d]pyrimidin-6-yl)-propyl]-(4-methyl-benzoyl)-amino]-propyl)-carbamic acid tert-butyl ester 100 mg of (+/−) {3-[[1-(5-benzyl-3-methyl-4-oxo-4,5-dihydro-isothiazolo[5,4-d]pyrimidin-6-yl)-propyl]-(4-methyl-benzoyl)-amino]-propyl}-carbamic acid tert-butyl ester (method 11) were dissolved in 2:1 IPA:hexanes and the compound was purified using a Chiralpak AD, 250×20 mm, 10μ column with a flow rate of 20 ml/min with 80% hexane, 20% isopropanol (0.1% diethylamine) as eluent. Elution time:— 10.42 min. Chiral purification generally resulted in 99% purity of the (+) enantiomer.

Methods 12a-12i

The following compounds were chirally purified in same manner as (+) (3-[[1-(5-benzyl-3-methyl-4-oxo-4,5-dihydro-isothiazolo[5,4-d]pyrimidin-6-yl)-propyl-(4-methyl-benzoyl)-amino]-propyl)-carbamic acid tert-butyl ester (method 12):

| Method # | Compound Name | Column Type | Solvent composition | (+) Enantiomer retention time | SM |
|---|---|---|---|---|---|
| 12a | (+) {3-[{1-[5-(4-Fluoro-benzyl)-3-methyl-4-oxo-4,5-dihydro-isothiazolo[5,4-d]pyrimidin-6-yl]-propyl}-(4-methyl-benzoyl)-amino]-propyl}-carbamic acid tert-butyl ester | Chiralpak AD | 85% hexanes 15% isopropanol 0.1% diethylamine | 10.7 min | Method 11a |
| 12b | (+) {3-[{1-[5-(3-Fluoro-benzyl)-3-methyl-4-oxo-4,5-dihydro-isothiazolo[5,4-d]pyrimidin-6-yl]-propyl}-(4-methyl-benzoyl)-amino]-propyl}-carbamic acid tert-butyl ester | Chiralpak AD | 75% hexanes 25% isopropanol 0.1% diethylamine | 7.6 min | Method 11b |
| 12c | (+) {3-[[1-(5-Benzyl-3-methyl-4-oxo-4,5-dihydro-isothiazolo[5,4-d]pyrimidin-6-yl)-propyl]-(4-chloro-benzoyl)-amino]-propyl}-carbamic acid tert-butyl ester | Chiralpak AD | 80% hexanes 20% isopropanol 0.1% diethylamine | 10.8 min | Method 11c |
| 12d | (+) {3-[[1-(5-Benzyl-3-methyl-4-oxo-4,5- | Chiralpak AD | 80% hexanes 20% isopropanol | 8.6 min | Method 11d |

-continued

| Method # | Compound Name | Column Type | Solvent composition | (+) Enantiomer retention time | SM |
|---|---|---|---|---|---|
| | dihydro-isothiazolo[5,4-d]pyrimidin-6-yl)-propyl]-(3-fluoro-4-methyl-benzoyl)-amino]-propyl}-carbamic acid tert-butyl ester | | 0.1% diethylamine | | |
| 12e | (+) {3-[[1-(5-Benzyl-3-methyl-4-oxo-4,5-dihydro-isothiazolo[5,4-d]pyrimidin-6-yl)-propyl]-(2,3-dichloro-benzoyl)-amino]-propyl}-carbamic acid tert-butyl ester | Chiralpak OD | 90% hexanes 5% methanol 5% ethanol 0.1% diethylamine | 7.5 min | Method 11e |
| 12f | (+) (3-{(Benzo[b]thiophene-2-carbonyl)-[1-(5-benzyl-3-methyl-4-oxo-4,5-dihydro-isothiazolo[5,4-d]pyrimidin-6-yl)-propyl]-amino}-propyl)-carbamic acid tert-butyl ester | Chiralpak AD | 50% hexanes 50% isopropanol 0.1% diethylamine | 7.2 min | Method 11f |
| 12g | (+) {3-[[1-(5-Benzyl-3-methyl-4-oxo-4,5-dihydro-isothiazolo[5,4-d]pyrimidin-6-yl)-propyl]-(4-bromo-benzoyl)-amino]-propyl}-carbamic acid tert-butyl ester | Chiralpak AD | 75% hexanes 25% isopropanol 0.1% diethylamine | 10.5 min | Method 11g |
| 12h | (+) {2-[[1-(5-Benzyl-3-methyl-4-oxo-4,5-dihydro-isothiazolo[5,4-d]pyrimidin-6-yl)-propyl]-(4-methyl-benzoyl)-amino]-ethyl}-carbamic acid tert-butyl ester | Chiralpak AD | 80% hexanes 20% isopropanol 0.1% diethylamine | 11.8 min | Method 11h |
| 12i | (+) N-[1-(5-Benzyl-3-methyl-4-oxo-4,5-dihydro-isothiazolo[5,4-d]pyrimidin-6-yl)-propyl]-N-(3-dimethylamino-propyl)-4-methyl-benzamide Example A-10 | Chiralpak AD | 90% hexanes 10% isopropanol 0.1% diethylamine | 9.5 min | Method 11i |

Chiral purification generally resulted in 99% purity of the (+) enantiomer.

Method 13 and Example A-1

(+) N-(3-Amino-propyl)-N-[1-(5-benzyl-3-methyl-4-oxo-4,5-dihydro-isothiazolo[5,4-d]pyrimidin-6-yl)-propyl]-4-methyl-benzamide hydrogen chloride (+) {3-[[1-(5-Benzyl-3-methyl-4-oxo-4,5-dihydro-isothiazolo[5,4-d]pyrimidin-6-propyl]-(4-methyl-benzoyl)-amino]-propyl}-carbamic acid tert-butyl ester (method 12) (0.117 g, 0.19 mmol) was dissolved in 2M HCl in ether and the mixture was stirred at r.t. for 20 h. The precipitated product was filtered off and washed with ether and dried in vacuo to yield the pure (+) N-(3-amino-propyl)-N-[1-(5-benzyl-3-methyl-4-oxo-4,5-dihydro-isothiazolo[5,4-d]pyrimidin-6-yl)-propyl]-4-methyl-benzamide chloride salt (91 mg, 87%). White powder, mp. 127.8-129.2° C. m/z 490 (MH$^+$), $^1$H NMR (DMSO-d$_6$, 500 MHz, 96° C.) δ: 0.63 (t, 3H), 1.40-1.74 (m, 2H), 1.75-1.96 (m, 1H), 2.05-2.20 (m, 1H), 2.39 (s, 3H), 2.46 (t, 2H), 2.72 (s, 3H), 3.36 (t, 2H), 4.83 (d, 1H), 5.50 (bs, 1H), 5.77 (d, 1H), 6.95-7.37 (m, 9H), 7.79 (bs, 3H).

Methods 13a-13h

The following compounds were synthesized according to Method 13:

| Method # | Compound Name | m/z | SM |
|---|---|---|---|
| 13a | (+) N-(3-Amino-propyl)-N-[1-(5-{4-fluorobenzyl}-3-methyl-4-oxo-4,5-dihydro-isothiazolo[5,4-d]pyrimidin-6-yl)-propyl]-4-methyl-benzamide hydrogen chloride Example A-2 | 508 (MH+) | Method 12a |
| 13b | (+) N-(3-Amino-propyl)-N-[1-(5-{3-fluorobenzyl}-3-methyl-4-oxo-4,5-dihydro-isothiazolo[5,4-d]pyrimidin-6-yl)-propyl]-4-methyl-benzamide hydrogen chloride Example A-3 | 508 (MH+) | Method 12b |
| 13c | (+) N-(3-Amino-propyl)-N-[1-(5-benzyl-3-methyl-4-oxo-4,5-dihydro-isothiazolo[5,4-d]pyrimidin-6-yl)-propyl]-4-chloro-benzamide hydrogen chloride Example A-5 | 510 (MH+) | Method 12c |
| 13d | (+) N-(3-Amino-propyl)-N-[1-(5-benzyl-3-methyl-4-oxo-4,5-dihydro-isothiazolo[5,4-d]pyrimidin-6-yl)-propyl]-3-fluoro-4-methyl-benzamide hydrogen chloride Example A-6 | 508 (MH+) | Method 12d |
| 13e | (+) N-(3-Amino-propyl)-N-[1-(5-benzyl-3-methyl-4-oxo-4,5-dihydro-isothiazolo[5,4-d]pyrimidin-6-yl)-propyl]-2,3-dichloro-benzamide hydrogen chloride Example A-7 | 544, 545, 546 (MH+) | Method 12e |
| 13f | (+) Benzo[b]thiophene-2-carboxylic acid (3-amino-propyl)-[1-(5-benzyl-3-methyl-4-oxo-4,5-dihydro-isothiazolo[5,4-d]pyrimidin-6-yl)-propyl]amide hydrogen chloride Example A-8 | 532 (MH+) | Method 12f |
| 13g | (+) N-(3-Amino-propyl)-N-[1-(5-benzyl-3-methyl-4-oxo-4,5-dihydro-isothiazolo[5,4-d]pyrimidin-6-yl)-propyl]-4-bromo-benzamide hydrogen chloride Example A-4 | 554, 556 (MH+) | Method 12g |
| 13h | (+) N-(2-Amino-ethyl)-N-[1-(5-benzyl-3-methyl-4-oxo-4,5-dihydro-isothiazolo[5,4-d]pyrimidin-6-yl)-propyl]-4-methyl-benzamide hydrogen chloride Example A-9 | 476 (MH+) | Method 12h |
| 13g | N-(3-Amino-propyl)-N-[1-(5-benzyl-3-methyl-4-oxo-4,5-dihydro-isothiazolo[5,4-d]pyrimidin-6-yl)-propyl]-4-methyl-benzamide hydrogen chloride | 490 (MH+) | Method 11 |

Method 14

N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide To a solution of N-(3-amino-propyl)-N-[1-(5-benzyl-3-methyl-4-oxo-4,5-dihydro-isothiazolo[5,4-d]pyrimidin-6-yl)-propyl]-4-methyl-benzamide hydrogen chloride (method 13g) (1.24 g, 2.54 mmol), in the presence of molecular sieves (2 g,) was added acetone (1 mL) and the mixture was stirred at room temperature for 2 h. Analysis of the reaction mixture by MS showed the completion of the schiff's base formation. To this mixture was added two drops of acetic acid followed by sodium triacetoxyborohydride (220 mg) and the mixture was stirred overnight. The reaction mixture was filtered and the filtrate was washed with water, dried ($Na_2SO_4$) and concentrated to get the crude product which was purified by column chromatography (silica gel) using 0-30 % EtOAc in hexanes. N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide was isolated as a white foam. Yield 0.206 g (15%). m/z 532 (MH+); $^1$H NMR (DMSO-$d_6$, 96° C.) δ: 0.65 (t, 3H), 1.05 (d, 6H), 1.26-1.48 (m, 1H), 1.65-1.70 (m, 1H), 1.80-1.98 (m, 1H), 2.00-2.17 (m, 1H), 2.35 (s, 3H), 2.63 (b, 2H), 2.80 (s, 3H), 3.05 (b, 1H), 3.40 (t, 2H), 4.90 (d, 1H), 5.50 (bs, 1H), 5.80 (d, 1H), 7.35-7.00 (m, 9H).

Method 15 and Example B-1

Chiral purification of (+) N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide The following compound was chirally purified in same manner as (+) (3-[[1-(5-benzyl-3-methyl-4-oxo-4,5-dihydro-isothiazolo[5,4-d]pyrimidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 15 | (+) N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide Example B-1 | Chiralpak AD | 85% hexanes 15% isopropanol 0.1% diethylamine | 8.0 min | Method 14 |

Method 16

5-Butyrylamino-3-methyl-isoxazole-4-carboxylic acid amide

A mixture of 5-amino-3-methyl-isoxazole-4-carboxylic acid amide (2 g, 14.18 mmol) in 10 ml of butyric anhydride was stirred at 150° C. for 0.5-1 h. The brown solution was diluted with hexane (100 ml) and cooled to room temperature. The solid crushed out from the mixture was filtered and washed with hexane, dried in vacuo. The title amide (2.6 g) was obtained as white solid.

Method 17

3-Methyl-6-propyl-5H-isoxazolo[5,4-d]pyrimidin-4-one

A suspension of 5-butyrylamino-3-methyl-isoxazole-4-carboxylic acid amide (method 16) (2.6 g, split into 20 vials) in 3.5 ml of 2N NaOH aq was subjected to microwave irradiation under the temperature of 140° C. for 20 min. The resulting solution was cooled with an ice bath, and the pH was adjusted to 1-3 with concentrated HCl. The crushed out solid was filtered, washed with water, dried over vacuum at 40° C. overnight. The title pyrimidinone (1.749 g) was obtained as white solid. $^1$H NMR (DMSO-$d_6$): 0.91 (t, 3H), 1.71 (m, 2H), 2.44 (s, 3H), 2.64 (t, 2H), 12.78 (s, 1H).

Method 18

5-Benzyl-3-methyl-6-propyl-5H-isoxazolo[5,4-d]pyrimidin-4-one

A suspension of 3-methyl-6-propyl-5H-isoxazolo[5,4-d]pyrimidin-4-one (method 17) (1.698 g, 8.8 mmol), benzylbromide (1.5 g, 8.8 mmol), potassium carbonate (2.43 g, 17.6 mmol) in 10 ml DMF was stirred at room temperature overnight. The mixture was diluted with water, extracted with EtOAc (50 ml×3), the combined organic phases were dried, concentrated, purified by flash column chromatography (elute: hexane-EtOAc=5:1). 1.69 g (68%) of the title compound was obtained as white solid. $^1$H NMR (DMSO-$d_6$): 0.80 (t, 3H), 1.61 (m, 2H), 2.43 (s, 3H), 2.73 (t, 2H), 5.35 (s, 2H), 7.12-7.35 (m, 5H).

Method 19

5-Benzyl-6-(1-bromo-propyl)-3-methyl-5H-isoxazolo[5,4-d]pyrimidin-4-one

A solution of 5-benzyl-3-methyl-6-propyl-5H-isoxazolo[5,4-d]pyrimidin-4-one (method 18) (3.167 g, 11.2 mmol) and sodium acetate (4.59 g, 56 mmol, 5 eq) in glacial acetic acid (26 ml) was treated with a preformed bromine solution (0.7 ml bromine in 10 ml of glacial acetic acid) (8.64 ml, 22.4 mmol, 2 eq). The mixture was stirred at 100° C. for 24 hrs. Excess bromine (8.64 ml, 22.4 mmol, 2 eq) was added to the mixture. The mixture was then stirred at 100° C. for another 24 hrs. Water was added to the reaction mixture, followed by aq. potassium carbonate. The mixture was extracted with DCM (50 ml×3), the combined organic phases were washed with water and dried, then concentrated to give the crude product which was purified by flash chromatography (elute: hexane-EtOAc). 2.5 g product was furnished as a white solid. $^1$H NMR (DMSO-$d_6$): 0.79 (t, 3H), 2.18 (m, 1H), 2.35 (m, 1H), 2.58 (s, 3H), 5.12 (t, 1H), 5.25 (d, 1H), 5.80 (d, 1H), 7.27-7.42 (m, 5H).

Method 20

{3-[1-(5-Benzyl-3-methyl-4-oxo-4,5-dihydro-isoxazolo[5,4-d]pyramidin-6-yl)-propylamino]-propyl}-carbamic acid tert-butyl ester To a suspension of 5-benzyl-6-(1-bromo-propyl)-3-methyl-5H-isoxazolo[5,4-d]pyrimidin-4-one (method 19) (2.8 g, 7.73 mmol) and potassium carbonate (2.67 g, 19.38 mmol) in acetonitrile (100 ml) was added tert-butyl-N-(3-aminopropyl)-carbamate (1.345 g, 7.73 mmol). The mixture was stirred at 100° C. overnight. Water (30 ml) was added to the mixture, which was extracted with EtOAc (3×50 ml). The combined organic phases were washed with brine (10 ml), dried, concentrated to obtain the crude title amine which was purified by flash chromatography column (elute: EtOAc-hexane=1-4~1-1) to give 2.6 g (74%) of product as white solid. $^1$H NMR (DMSO-$d_6$): 0.85 (t, 3H), 1.32 (m, 2H), 1.41 (s, 9H), 1.58 (m, 1H), 1.65 (m, 1H), 2.09 (m, 1H), 2.40 (m, 1H), 2.60 (s, 3H), 2.81 (m, 2H), 3.29 (m, 1H), 3.75 (m, 1H), 5.42 (d, 1H), 5.63 (d, 1H), 6.72 (br, 1H), 7.25-7.45 (m, 5H).

Method 21

(3-[[1-(5-Benzyl-3-methyl-4-oxo-4,5-dihydro-isoxazolo[5,4-d]pyramidin-6-yl)-propyl]-(4-methyl-benzoyl)-amino]-propyl)-carbamic acid tert-butyl ester A solution of {3-[1-(5-benzyl-3-methyl-4-oxo-4,5-dihydro-isoxazolo[5,4-d]pyramidin-6-yl)-propylamino]-propyl}-carbamic acid tert-butyl ester (method 20) (135 mg, 0.297 mmol) in DCM (4 ml) was added to 4-methyl-benzoyl chloride (46 mg, 0.297 mmol) followed by triethylamine (60 mg, 0.594 mmol). The mixture was stirred at room temperature for 1 hr. Then diluted with DCM, washed with saturated aq. sodium bicarbonate. The organic phase was dried, filtered, and concentrated. The crude oil was purified by flash column chromatography (solvent: EtOAc-hexane) to furnish (3-[[-(5-benzyl-3-methyl-4-oxo-4,5-dihydro-isoxazolo[5,4-d]pyramidin-6-yl)-propyl]-(4-methyl-benzoyl)-amino]-propyl)-carbamic acid tert-butyl ester (130 mg) (76% yield) as a white solid. $^1$H NMR (500 MHz, 100° C., DMSO-$d_6$): 0.71 (t, 3H), 1.12 (m, 1H), 1.35 (s, 9H), 1.47 (m, 1H), 1.92 (m, 1H), 2.14 (m, 1H), 2.37 (s, 3H), 2.56 (s, 3H), 2.57 (m, 2H), 3.29 (m, 2H), 5.01 (d, 1H), 5.68 (m, br, 1H), 5.79 (d, 1H), 6.06 (br, 1H), 7.14-7.36 (m, 9H).

Method 22

Chiral purification of (+) (3-[[1-(5-Benzyl-3-methyl-4-oxo-4,5-dihydro-isoxazolo[5,4-d]pyramidin-6-yl)-propyl]-(4-methyl-benzoyl)-amino]-propyl)-carbamic acid tert-butyl ester The following compound was chirally purified in same manner as (+) (3-[[1-(5-benzyl-3-methyl-4-oxo-4,5-dihydro-isothiazolo[5,4-d]pyramidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 22 | (+) (3-[[1-(5-Benzyl-3-methyl-4-oxo-4,5-dihydro-isoxazolo[5,4-d]pyrimidin-6-yl)-propyl]-(4-methyl-benzoyl)-amino]-propyl)-carbamic acid tert-butyl ester | Chiralpak AD | 70% hexanes 30% isopropanol 0.1% diethylamine | 12.1 min | Method 21 |

Method 23 and Example C-1

(+) N-(3-Amino-propyl)-N-[1-(5-benzyl-3-methyl-4-oxo-4,5-dihydro-isoxazolo[5,4-d]-pyramidin-6-yl)-propyl]-4-methyl-benzamide hydrogen chloride A solution of (+) (3-[[1-(5-benzyl-3-methyl-4-oxo-4,5-dihydro-isoxazolo[5,4-d]pyramidin-6-yl)-propyl]-(4-methyl-benzoyl)-amino]-propyl)-carbamic acid tert-butyl ester (method 22) (23 mg, 0.04 mmol) in 3 ml of 4 M HCl in dioxane was stirred at room temperature for 2 hr. The solvent was distilled off by vacuo, the residue was dried at 40~50° C. for overnight under vacuum. The corresponding amine chloride salt was obtained. Yield was 19 mg (93%). m/z 474 (MH$^+$) $^1$H NMR (500 MHz, 100° C., DMSO-d$_6$): 0.68 (t, 3H), 1.52 (m, 1H), 1.72 (m, 1H), 1.92 (m, 1H), 2.10 (m, 1H), 2.39 (s, 3H), 2.51 (m, 2H), 2.57 (s, 3H), 3.41 (m, 2H), 4.85 (br, 1H), 5.50 (br, 1H), 5.77 (d, 1H), 7.07 (br, 2H), 7.24-7.35 (m, 7H), 7.73 (br, 3H).

Method 24

N-(4-Cyano-3-methyl-isothiazol-5-yl)-3-methyl-butyramide

To a solution of 5-amino-3-methylisothiazole-4-carbonitrile (method 4) (6.38 g, 45.9 mmol) in pyridine (20 mL) at 0° C., isovaleryl chloride (6.65 g, 55 mmol) was added dropwise. After the completion of the addition the reaction mixture was allowed to warm to r.t. and stirred overnight. The TLC and the MS showed the complete disappearance of the starting material and the reaction mixture was diluted with CHCl$_3$ (200 mL), washed with water (200 mL), 2N HCl (225 mL), satd. NaHCO$_3$ (200 mL), brine (200 mL) and dried over Na$_2$SO$_4$. Concentration of the CHCl$_3$ layer provided the crude product which was triturated from DCM/hexanes (1/10) and filtered off to isolate N-(4-cyano-3-methyl-isothiazol-5-yl)-3-methyl-butyramide (8.1 g, 79%) as an off-white crystalline solid. $^1$H NMR (300 MHz) δ 1.04 (d, 6H), 2.18-2.32 (m, 1H), 2.46 (d, 2H), 2.53 (s, 3H), 9.87 (bs, 1H).

Method 25

3-Methyl-5-(3-methyl-butyrylamino)-isothiazole-4-carboxylic acid amide

To a solution of N-(4-cyano-3-methyl-isothiazol-5-yl)-3-methyl-butyramide (method 24) (8 g, 35.8 mmol) in 30% aqueous NH$_4$OH (200 mL), was added dropwise 100 mL of hydrogen peroxide at r.t. After the completion of the addition the reaction mixture was stirred at 60° C. overnight after which the TLC showed the complete disappearance of SM. The reaction mixture was concentrated to 40 mL and extracted with chloroform (3×100 mL). The organic layer was dried (Na$_2$SO$_4$) and concentrated to obtain 3-methyl-5-(3-methyl-butyrylamino)-isothiazole-4-carboxylic acid amide (6.1 g, 71%) as a light yellow solid. $^1$H NMR (300 MHz) δ 1.03 (d, 6H), 2.24 (m, 1H), 2.43 (d, 2H), 2.69 (s, 3H), 5.98 (bs, 2H), 11.77 (bs, 1H).

Method 26

6-Isobutyl-3-methyl-5H-isothiazolo[5,4-d]pyrimidin-4-one

3-Methyl-5-(3-methyl-butyrylamino)-isothiazole-4-carboxylic acid amide (method 25) (6 g, 25 mmol) was suspended in 150 mL of 30% NH$_3$ and then was heated to 140° C. for 5 h in a pressure reactor. The mixture was cooled and neutralized to pH 7. The reaction mixture was extracted with EtOAc (3×100 mL) and the combined organic layers were washed with water (100 mL), brine (100 mL) and concentrated to get the crude product which was further purified by column (silica gel) chromatography using 30% EtOAc in hexanes as eluent. Concentration of the pure product fractions provided 6-isobutyl-3-methyl-5H-isothiazolo[5,4-d]pyrimidin-4-one (2.2 g, 38%) as an off-white powder. $^1$H NMR (300 MHz) δ 1.05 (d, 6H), 2.32 (m, 1H), 2.69 (d, 2H), 2.82 (s, 3H).

Method 27

5-Benzyl-6-isobutyl-3-methyl-5H-isothiazolo[5,4-d]pyrimidin-4-one

To a solution of 6-isobutyl-3-methyl-5H-isothiazolo[5,4-d]pyrimidin-4-one (method 26) (1.31 g, 5.8 mmol) in 20 mL of anhydrous DMF was added 1.38 g (10 mmol) of anhydrous K$_2$CO$_3$ followed by benzyl bromide (1.18 g, 6.9 mmol) and the mixture was stirred at room temperature overnight. The TLC of the reaction mixture showed the complete disappearance of the SM. The reaction mixture was poured into ice-cold water and extracted with EtOAc (3×100 mL). The combined extracts were washed with water (100 mL), brine (100 mL), dried (Na$_2$SO$_4$) and concentrated. The TLC and the $^1$H NMR showed the presence of two products N alkylated as well as O-alkylated products in a ratio of 7:3. The products were separated by column (silica gel, 116 g) chromatography using 10% EtOAc in hexanes. 5-Benzyl-6-isobutyl-3-methyl-5H-isothiazolo[5,4-d]pyrimidin-4-one was isolated as white crystalline solid (1.3 g, 70%). m/z 314 (MH$^+$), $^1$H NMR (300 MHz) δ 0.94 (d, 6H), 2.23-2.37 (m, 1H), 2.64 (d, 2H), 2.82 (s, 3H), 5.38 (s, 2H), 7.10-7.38 (m, 5H).

Methods 27a-b

The following compounds were synthesized according to Method 27:

| Method # | Compound Name | m/z | Alkylating agent |
|---|---|---|---|
| 27a | 5-(4-Fluoro-benzyl)-6-isobutyl-3-methyl-5H-isothiazolo[5,4-d]pyrimidin-4-one | 332 (MH$^+$) | 4-fluorobenzyl bromide |
| 27b | 5-(3-Fluoro-benzyl)-6-isobutyl-3-methyl-5H-isothiazolo[5,4-d]pyrimidin-4-one | 332 (MH$^+$) | 3-fluorobenzyl bromide |

Method 28

5-Benzyl-6-(1-bromo-2-methyl-propyl)-3-methyl-5H-isothiazolo[5,4-d]pyrimidin-4-one To a solution of 5-benzyl-6-isobutyl-3-methyl-5H-isothiazolo[5,4-d]pyrimidin-4-one (method 27) (1.3 g, 4.2 mmol) and sodium acetate (2 g) in acetic acid (10 mL) at 100° C., a solution of the bromine (1.32 g, 8.4 mmol) in acetic acid (10 mL) was added dropwise over a period of 20 minutes. The reaction mixture was stirred at that temperature for 30 min and cooled and the TLC (eluent 10% EtOAc in hexanes) and MS showed the complete disappearance of the SM and only the product. The reaction mixture was poured into ice water and extracted with EtOAc (3×60 mL) and the organic layers were combined and washed with 2% sodium thiosulfate solution (60 mL), water (100 mL), brine (100 mL) and dried over Na$_2$SO$_4$. Concentration of the organic layer provided 5-benzyl-6-(1-bromo-2-methyl-propyl)-3-methyl-5H-isothiazolo[5,4-d]pyrimidin-4-one (1.61 g, 99%) as white crystalline solid. m/z 392, 394 (MH$^+$), $^1$H NMR (300 MHz) δ 0.54 (d, 3H), 1.11 (d, 3H), 2.62-2.76 (m, 1H), 2.83 (s, 3H), 4.42 (d, 1H), 4.80 (d, 1H), 6.22 (d, 1H), 7.12-7.42 (m, 5H).

Methods 28a-b

The following compounds were synthesized according to Method 28:

| Method # | Compound Name | m/z | SM |
|---|---|---|---|
| 28a | 6-(1-Bromo-2-methyl-propyl)-5-(4-fluoro-benzyl)-3-methyl-5H-isothiazolo[5,4-d]pyrimidin-4-one | 410, 412 (MH$^+$) | Method 27a |
| 28b | 6-(1-Bromo-2-methyl-propyl)-5-(3-fluoro-benzyl)-3-methyl-5H-isothiazolo[5,4-d]pyrimidin-4-one | 410, 412 (MH$^+$) | Method 27b |

Method 29

6-(1-Azido-2-methyl-propyl)-5-benzyl-3-methyl-5H-isothiazolo[5,4-d]pyrimidin-4-one To a solution of 5-benzyl-6-(1-bromo-2-methyl-propyl)-3-methyl-5H-isothiazolo[5,4-d]pyrimidin-4-one (method 28) (0.6 g, 1.52 mmol) in anhydrous DMF (20 mL), sodium azide (0.65 g, 10 mmol) was added and the mixture was stirred at room temperature for 1 hour. The TLC of the RM showed the complete disappearance of the starting bromide. The reaction mixture was poured into ice water (300 mL) and extracted with EtOAc (3×100 mL). The organic layer was washed with water (100 mL), brine (100 mL) and dried (Na$_2$SO$_4$). Concentration of the organic layer provided the crude product which was purified by column (silica gel) chromatography using 30% EtOAc in hexanes as eluent to isolate 6-(1-azido-2-methyl-propyl)-5-benzyl-3-methyl-5H-isothiazolo[5,4-d]pyrimidin-4-one (0.506 g, 94%) as a low melting solid. m/z 355 (MH$^+$), $^1$H NMR (300 MHz) δ 0.57 (d, 3H), 1.07 (d, 3H), 2.50-2.74 (m, 1H), 2.98 (s, 3H), 3.71 (d, 1H), 5.05 (d, 1H), 5.78 (d, 1H), 7.12-7.40 (m, 5H).

Methods 29a-b

The following compounds were synthesized according to Method 29:

| Method # | Compound Name | m/z | SM |
|---|---|---|---|
| 29a | 6-(1-Azido-2-methyl-propyl)-5-(4-fluoro-benzyl)-3-methyl-5H-isothiazolo[5,4-d]pyrimidin-4-one | 373 (MH$^+$) | Method 28a |
| 29b | 6-(1-Azido-2-methyl-propyl)-5-(3-fluoro-benzyl)-3-methyl-5H-isothiazolo[5,4-d]pyrimidin-4-one | 373 (MH$^+$) | Method 28b |

Method 30

6-(1-Amino-2-methyl-propyl)-5-benzyl-3-methyl-5H-isothiazolo[5,4-d]pyrimidin-4-one To a solution of 6-(1-azido-2-methyl-propyl)-5-benzyl-3-methyl-5H-isothiazolo[5,4-d]pyramidin-4-one (method 29) (0.5 g, 1.41 mmol) in methanol (20 mL) was added 5% Pd/C (20% by wt.) and the resulting mixture was stirred at r.t. in an atmosphere of H$_2$ and the progress of the reaction was monitored by MS. After the disappearance of the starting material the reaction mixture was filtered through celite and washed with EtOAc. Concentration of the filtrate provided 6-(1-amino-2-methyl-propyl)-5-benzyl-3-methyl-5H-isothiazolo[5,4-d]pyrimidin-4-one as a thick oil. The product was used as such in the next reaction with out further purification. m/z 349 (MH$^+$).

Methods 30a-b

The following compounds were synthesized according to Method 30:

| Method # | Compound Name | m/z | SM |
|---|---|---|---|
| 30a | 6-(1-Amino-2-methyl-propyl)-5-(4-fluoro-benzyl)-3-methyl-5H-isothiazolo[5,4-d]pyrimidin-4-one | 367 (MH$^+$) | Method 29a |
| 30b | 6-(1-Amino-2-methyl-propyl)-5-(3-fluoro-benzyl)-3-methyl-5H-isothiazolo[5,4-d]pyrimidin-4-one | 367 (MH$^+$) | Method 29b |

Method 31

{3-[1-(5-Benzyl-3-methyl-4-oxo-4,5-dihydro-isothiazolo[5,4-d]pyramidin-6-yl)-2-methyl-propylamino]-propyl}-carbamic acid tert-butyl ester To a solution of 6-(1-amino-2-methyl-propyl)-5-benzyl-3-methyl-5H-isothiazolo[5,4-d]pyrimidin-4-one (method 30) in DCM (30 mL), 4 Å molecular sieves (5 g) was added followed by (3-oxo-propyl)-carbamic acid tert-butyl ester (1.2 eq) and the reaction mixture was stirred at r.t. for 3 h and the progress of the reaction was monitored by MS. After the complete disappearance of the starting amine, a catalytic amount of acetic acid was added to the reaction followed by sodium triacetoxyborohydride (1.2 eq) and the reaction mixture was stirred at r.t. overnight. After the completion of the reaction (MS), the reaction mixture was filtered and the residue was washed with DCM and the filtrate was washed with water (100 mL), brine (100 mL) and concentrated to get the crude product which was used as such for the next reaction. m/z 486 (MH$^+$).

Methods 31a-c

The following compounds were synthesized according to Method 31:

| Method # | Compound Name | m/z | SM |
|---|---|---|---|
| 31a | (3-{1-[5-(4-Fluoro-benzyl)-3-methyl-4-oxo-4,5-dihydro-isothiazolo[5,4-d]pyrimidin-6-yl]-2-methyl-propylamino}-propyl)-carbamic acid tert-butyl ester | 504 (MH$^+$) | Method 30a |
| 31b | (3-{1-[5-(3-Fluoro-benzyl)-3-methyl-4-oxo-4,5-dihydro-isothiazolo[5,4-d]pyrimidin-6-yl]-2-methyl-propylamino}-propyl)-carbamic acid tert-butyl ester | 504 (MH$^+$) | Method 30b |
| 31c | {2-[1-(5-Benzyl-3-methyl-4-oxo-4,5-dihydro-isothiazolo[5,4-d]pyrimidin-6-yl)-2-methyl-propylamino]-ethyl}-carbamic acid tert-butyl ester | 472 (MH$^+$) | Method 30 |

Method 32

5-Benzyl-6-[1-(2-[1,3]dioxolan-2-yl-ethylamino)-2-methyl-propyl]-3-methyl-5H-isothiazolo[5,4-d]pyrimidin-4-one To a solution of 6-(1-amino-2-methyl-propyl)-5-benzyl-3-methyl-5H-isothiazolo[5,4-d]pyrimidin-4-one (method 30) (1.6 g, 4.88 mmol) in anhydrous DMF (20 mL), 2-(2-bromoethyl)-[1,3]dioxolane (0.88 g, 4.88 mmol) was added and the resulting solution was heated at 70° C. for 2 h. The reaction mixture was cooled, diluted with water and extracted with EtOAc (3×60 mL). The combined organic extracts were dried (Na$_2$SO$_4$) and concentrated to provide the crude product (2 g), which was used as such in the next reaction. m/z 429 (MH$^+$); $^1$H-NMR (300 MHz) δ 0.88 (d, 3H), 0.96 (d, 3H), 1.54-1.62 (m, 2H), 1.86-2.05 (m, 2H), 2.18 (bs, 1H), 2.38-2.46 (m, 1H), 2.84 (s, 3H), 3.57 (d, 1H), 3.74-3.94 (m, 4H), 4.78 (t, 1H), 4.99 (d, 1H), 5.85 (d, 1H), 7.15-7.38 (m, 5H).

Method 33

{3-[[1-(5-Benzyl-3-methyl-4-oxo-4,5-dihydro-isothiazolo[5,4-d]pyrimidin-6-yl)-2-methyl-propyl]-(4-methyl-benzoyl)-amino]-propyl}-carbamic acid tert-butyl ester To a solution of the crude {3-[1-(5-benzyl-3-methyl-4-oxo-4,5-dihydro-isothiazolo[5,4-d]pyrimidin-6-yl)-2-methyl-propylamino]-propyl}-carbamic acid tert-butyl ester (method 31) in pyridine (10 mL) at r.t., a solution of the p-toluoyl chloride (0.616 g, 4 mmol) in DCM (10 mL) was added dropwise and the resulting solution was stirred at r.t. for 2 days. The reaction mixture was diluted with DCM (100 mL) washed with water (2×100 mL), brine (100 mL) and dried (Na$_2$SO$_4$). Concentration of the organic layer provided the crude product which was purified by column (silica gel) chromatography using 20-30% EtOAc in hexanes as eluent. Product isolated was 0.276 g. m/z 604 (MH$^+$).

Methods 33a-g

The following compounds were synthesized according to Method 33:

| Method # | Compound Name | m/z | SM | Acylating agent |
|---|---|---|---|---|
| 33a | {3-[[1-[5-(4-Fluoro-benzyl)-3-methyl-4-oxo-4,5-dihydro-isothiazolo[5,4-d]pyrimidin-6-yl]-2-methyl-propyl}-(4-methyl-benzoyl)-amino]-propyl}-carbamic acid tert-butyl ester | 622 (MH$^+$) | Method 31a | 4-methyl-benzoyl chloride |
| 33b | {3-[{1-[5-(3-Fluoro-benzyl)-3-methyl-4-oxo-4,5-dihydro-isothiazolo[5,4-d]pyrimidin-6-yl]-2-methyl-propyl}-(4-methyl-benzoyl)-amino]-propyl}-carbamic acid tert-butyl ester | 622 (MH$^+$) | Method 31b | 4-methyl-benzoyl chloride |
| 33c | {2-[[1-(5-Benzyl-3-methyl-4-oxo-4,5-dihydro-isothiazolo[5,4-d]pyrimidin-6-yl)-2-methyl-propyl]-(4-methyl-benzoyl)-amino]-ethyl}-carbamic acid tert-butyl ester | 590 (MH$^+$) | Method 31c | 4-methyl-benzoyl chloride |
| 33d | {2-[[1-(5-Benzyl-3-methyl-4-oxo-4,5-dihydro-isothiazolo[5,4-d]pyrimidin-6-yl)-2-methyl-propyl]-(4-bromo-benzoyl)-amino]-ethyl}-carbamic acid tert-butyl ester | 654, 656 (MH$^+$) | Method 31c | 4-bromo-benzoyl chloride |
| 33e | {2-[[1-(5-Benzyl-3-methyl-4-oxo-4,5-dihydro-isothiazolo[5,4-d]pyrimidin-6-yl)-2-methyl-propyl]-(3-fluoro-4-methyl-benzoyl)-amino]-ethyl}-carbamic acid tert-butyl ester | 608 (MH$^+$) | Method 31c | 3-fluoro-4-methyl-benzoyl chloride |
| 33f | {3-[[1-(5-Benzyl-3-methyl-4-oxo-4,5-dihydro-isothiazolo[5,4-d]pyrimidin-6-yl)-2-methyl-propyl]-(3-fluoro-4-methyl-benzoyl)-amino]-propyl}-carbamic acid tert-butyl ester | 622 (MH$^+$) | Method 31 | 3-fluoro-4-methyl-benzoyl chloride |
| 33g | {3-[[1-(5-Benzyl-3-methyl-4-oxo-4,5-dihydro-isothiazolo[5,4-d]pyrimidin-6-yl)-2-methyl-propyl]-(4-bromo-benzoyl)-amino]-propyl}-carbamic acid tert-butyl ester | 668, 670 (MH$^+$) | Method 31 | 4-bromo-benzoyl chloride |

Methods 34a-g

The following compounds were chirally purified in same manner as (+) (3-[[1-(5-benzyl-3-methyl-4-oxo-4,5-dihydro-isothiazolo[5,4-d]pyrimidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 34a | (+) {3-[{1-[5-(4-Fluoro-benzyl)-3-methyl-4-oxo-4,5-dihydro-isothiazolo[5,4-d]pyrimidin-6-yl]-2-methyl-propyl}-(4-methyl-benzoyl)-amino]-propyl}-carbamic acid tert-butyl ester | Chiralpak AD | 85% hexanes 15% isopropanol 0.1% diethylamine | 7.1 min | Method 33a |
| 34b | (+) {3-[{1-[5-(3-Fluoro-benzyl)-3-methyl-4-oxo-4,5-dihydro-isothiazolo[5,4-d]pyrimidin-6-yl]-2-methyl-propyl}-(4-methyl-benzoyl)-amino]-propyl}-carbamic acid tert-butyl ester | Chiralpak AD | 85% hexanes 15% isopropanol 0.1% diethylamine | 8.0 min | Method 33b |
| 34c | (+) {2-[[1-(5-Benzyl-3-methyl-4-oxo-4,5-dihydro-isothiazolo[5,4-d]pyrimidin-6-yl)-2-methyl-propyl]-(4-methyl-benzoyl)-amino]-ethyl}-carbamic acid tert-butyl ester | Chiralpak AD | 80% hexanes 20% isopropanol 0.1% diethylamine | 7.7 min | Method 33c |
| 34d | (+) {2-[[1-(5-Benzyl-3-methyl-4-oxo-4,5-dihydro-isothiazolo[5,4-d]pyrimidin-6-yl)-2-methyl-propyl]-(4-bromo-benzoyl)-amino]-ethyl}-carbamic acid tert-butyl ester | Chiralpak AD | 75% hexanes 25% isopropanol 0.1% diethylamine | 7.9 min | Method 33d |
| 34e | (+) {2-[[1-(5-Benzyl-3-methyl-4-oxo-4,5-dihydro-isothiazolo[5,4-d]pyrimidin-6-yl)-2-methyl-propyl]-(3-fluoro-4-methyl-benzoyl)-amino]-ethyl}-carbamic acid tert-butyl ester | Chiralpak AD | 75% hexanes 25% isopropanol 0.1% diethylamine | 6.3 min | Method 33e |
| 34f | (+) {3-[[1-(5-Benzyl-3-methyl-4-oxo-4,5-dihydro-isothiazolo[5,4-d]pyrimidin-6-yl)-2-methyl-propyl]-(3-fluoro-4-methyl-benzoyl)-amino]-propyl}-carbamic acid tert-butyl ester | Chiralpak AD | 80% hexanes 20% isopropanol 0.1% diethylamine | 8.6 min | Method 33f |
| 34g | (+) {3-[[1-(5-Benzyl-3-methyl-4-oxo-4,5-dihydro-isothiazolo[5,4-d]pyrimidin-6-yl)-2-methyl-propyl]-(4-bromo-benzoyl)-amino]-propyl}-carbamic acid tert-butyl ester | Chiralpak AD | 80% hexanes 20% isopropanol 0.1% diethylamine | 7.0 min | Method 33g |

Chiral purification generally resulted in 99% purity of the (+) enantiomer.

Method 35

N-(3-Amino-propyl)-N-[1-(5-benzyl-3-methyl-4-oxo-4,5-dihydro-isothiazolo[5,4-d]pyrimidin-6-yl)-2-methyl-propyl]-4-methyl-benzamide hydrogen chloride {3-[[1-(5-Benzyl-3-methyl-4-oxo-4,5-dihydro-isothiazolo[5,4-d]pyramidin-6-yl)-2-methyl-propyl]-(4-methyl-benzoyl)-amino]-propyl}-carbamic acid tert-butyl ester (method 33) (0.245 g, 0.40 mmol) was dissolved in 4M HCl in 1,4-dioxane and the mixture was stirred at r.t. for 20 min and the TLC showed the complete disappearance of the starting material. The reaction 10 mixture was concentrated in a rotary evaporator and the residue was triturated with ether. The precipitated product was filtered off and washed with ether and dried under vacuo to yield N-(3-amino-propyl)-N-[-(5-benzyl-3-methyl-4-oxo-4,5-dihydro-isothiazolo[5,4-d]pyramidin-6-yl)-2-methyl-propyl]-4-methyl-benzamide as the hydrochloride salt (0.219 g, 100%). White powder, mp. 139-140° C. m/z 504 (MH$^+$), $^1$H NMR (DMSO-d$_6$, 300 MHz, 96° C.) δ: 0.45 (d, 3H), 0.90 (d, 3H), 1.12-1.30 (m, 1H), 1.46-1.63 (m, 1H), 2.25 (t, 2H), 2.36 (s, 3H), 2.64-2.7 (m, 1H), 2.68 (s, 3H), 3.34 (t, 2H), 5.06 (d, 1H), 5.59 (d, 1H), 5.90 (d, 1H), 7.20-7.40 (m, 9H), 7.71 (bs, 3H).

Methods 35a-g

The following compounds were synthesized according to Method 35:

| Method # | Compound Name | m/z | SM |
|---|---|---|---|
| 35a | (+) N-(3-Amino-propyl)-N-{1-[5-(4-fluoro-benzyl)-3-methyl-4-oxo-4,5-dihydro-isothiazolo[5,4-d]pyrimidin-6-yl]-2-methyl-propyl}-4-methyl-benzamide hydrogen chloride Example D-1 | 522 (MH$^+$) | Method 34a |
| 35b | (+) N-(3-Amino-propyl)-N-{1-[5-(3-fluoro-benzyl)-3-methyl-4-oxo-4,5-dihydro-isothiazolo[5,4-d]pyrimidin-6-yl]-2-methyl-propyl}-4-methyl-benzamide hydrogen chloride Example D-3 | 522 (MH$^+$) | Method 34b |
| 35c | (+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-methyl-benzamide hydrogen chloride Example D-5 | 490 (MH$^+$) | Method 34c |
| 35d | (+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-bromo-benzamide hydrogen chloride Example D-4 | 554, 556 (MH$^+$) | Method 34d |
| 35e | (+) N-(2-Amino-ethyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide hydrogen chloride Example D-6 | 508 (MH$^+$) | Method 34e |
| 35f | (+) N-(3-Amino-propyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide hydrogen chloride Example D-7 | 522 (MH$^+$) | Method 34f |
| 35g | (+) N-(3-Amino-propyl)-N-[1-(5-benzyl-3-methyl-4-oxo-4,5-dihydro-isothiazolo[5,4-d]pyrimidin-6-yl)-2-methyl-propyl]-4-bromo-benzamide hydrogen chloride Example D-8 | 568, 570 (MH$^+$) | Method 34g |

Method 36 and Example D-2

Chiral purification of (+) N-(3-Amino-propyl)-N-[1-(5-benzyl-3-methyl-4-oxo-4,5-dihydro-isothiazolo[5,4-d]pyramidin-6-yl)-2-methyl-propyl]-4-methyl-benzamide The following compound was chirally purified in same manner as (+) (3-[[1-(5-benzyl-3-methyl-4-oxo-4,5-dihydro-isothiazolo[5,4-d]pyramidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 36 | (+) N-(3-Amino-propyl)-N-[1-(5-benzyl-3-methyl-4-oxo-4,5-dihydro-isothiazolo[5,4-d]pyrimidin-6-yl)-2-methyl-propyl]-4-methyl-benzamide Example D-2 | Chiralpak AD | 70% hexanes 30% isopropanol 0.1% diethylamine | 8.0 min | Method 35 |

Method 37

N-[1-(5-Benzyl-3-methyl-4-oxo-4,5-dihydro-isothiazolo[5,4-d]pyramidin-6-yl)-2-methyl-propyl]-4-bromo-N-(2-[1,3]dioxolan-2-yl-ethyl)-benzamide 5-Benzyl-6-[1-(2-[1,3]dioxolan-2-yl-ethylamino)-2-methyl-propyl]-3-methyl-5H-isothiazolo[5,4-d]pyramidin-4-one (method 32) (1 g, 2.33 mmol) was dissolved in chloroform (70 mL) and to the chloroform solution diisopropylethyl amine (0.9 g, 6.99 mmol) was added followed by the addition of 4-bromobenzoyl chloride (0.76 g, 3.49 mmol) and the mixture was refluxed overnight. The MS showed the disappearance of the starting material and only the product peak at 611 ($MH^+$). The reaction mixture was concentrated and column purified (silica gel, 160 g) using 10-20% EtOAc in hexanes as eluent. The concentration of the product fractions provided the pure product as white foam (1.1 g, 77%). m/z 611, 613 ($MH^+$); $^1$H-NMR (300 MHz) δ 0.35 (d, 3H), 0.94 (d, 3H), 0.94-1.06 (m, 1H), 1.36-1.46 (m, 1H), 2.68-2.78 (m, 1H), 2.88 (s, 3H), 3.38-3.52 (m, 1H), 3.54-3.70 (m, 5H), 4.34 (t, 1H), 5.18 (d, 1H), 5.73 (d, 1H), 6.13 (d, 1H), 7.20 (d, 2H), 7.26-7.46 (m, 5H), 7.56 (d, 2H).

Methods 37a-b

The following compounds were synthesized according to Method 37:

| Method # | Compound Name | m/z | SM | Acylating agent |
|---|---|---|---|---|
| 37a | N-[1-(5-Benzyl-3-methyl-4-oxo-4,5-dihydro-isothiazolo[5,4-d]pyrimidin-6-yl)-2-methyl-propyl]-N-(2-[1,3]dioxolan-2-yl-ethyl)-4-methyl-benzamide | 547 ($MH^+$) | Method 32 | 4-methyl-benzoyl chloride |
| 37b | N-[1-(5-Benzyl-3-methyl-4-oxo-4,5-dihydro-isothiazolo[5,4-d]pyrimidin-6-yl)-2-methyl-propyl]-N-(2-[1,3]dioxolan-2-yl-ethyl)-3-fluoro-4-methyl-benzamide | 565 ($MH^+$) | Method 32 | 3-fluoro-4-methyl-benzoyl chloride |

Method 38

N-[1-(5-Benzyl-3-methyl-4-oxo-4,5-dihydro-isothiazolo[5,4-d]pyramidin-6-yl)-2-methyl-propyl]-4-bromo-N-(3-oxo-propyl)-benzamide N-[1-(5-Benzyl-3-methyl-4-oxo-4,5-dihydro-isothiazolo[5,4-d]pyrimidin-6-yl)-2-methyl-propyl]-4-bromo-N-(2-[1,3]dioxolan-2-yl-ethyl)-benzamide (method 37) (1.1 g, 1.8 mmol) was dissolved in 20 mL of 80% acetic acid and the solution was heated at 80° C. for 2 h. The reaction mixture was cooled in an ice bath and neutralized slowly by the addition of solid $NaHCO_3$ until pH 8. The thus obtained mixture was extracted with DCM (3×100 mL). The combined organic layers was washed with brine (100 mL) and dried ($Na_2SO_4$). Concentration of the DCM layer provided a yellow foam (1 g crude yield) and it was used as such in the next reaction. m/z 567, 569 ($MH^+$).

Methods 38a-b

The following compounds were synthesized according to Method 38:

| Method # | Compound Name | m/z | SM |
|---|---|---|---|
| 38a | N-[1-(5-Benzyl-3-methyl-4-oxo-4,5-dihydro-isothiazolo[5,4-d]pyrimidin-6-yl)-2-methyl-propyl]-4-methyl-N-(3-oxo-propyl)-benzamide | 503 ($MH^+$) | Method 37a |
| 38b | N-[1-(5-Benzyl-3-methyl-4-oxo-4,5-dihydro-isothiazolo[5,4-d]pyrimidin-6-yl)-2-methyl-propyl]-3-fluoro-4-methyl-N-(3-oxo-propyl)-benzamide | 521 ($MH^+$) | Method 37b |

Method 39

N-[1-(5-Benzyl-3-methyl-4-oxo-4,5-dihydro-isothiazolo[5,4-d]pyramidin-6-yl)-2-methyl-propyl]-4-bromo-N-(3-dimethylamino-propyl)-benzamide To a solution of N-[1-(5-benzyl-3-methyl-4-oxo-4,5-dihydro-isothiazolo[5,4-d]pyrimidin-6-yl)-2-methyl-propyl]-4-bromo-N-(3-oxo-propyl)-benzamide (method 38) (1 g, 1.76 mmol) in methanol (20 mL) two drops of acetic acid were added followed by the addition of dimethylamine (1 mL, 2M solution in THF) and sodium cyanoborohydride (0.314 g, 5 mmol) and the mixture was stirred at room temperature for 3 h. The reaction mixture was concentrated and the residue was dissolved in DCM (100 mL) and the organic layer was washed with satd. $NaHCO_3$ (3×100 mL). The organic layer was concentrated and the crude product was purified by column chromatography using 0-10% MeOH in EtOAc. The pure product fractions were concentrated and the thus obtained foam was crystallized from ether/hexanes to get the product as white crystalline solid. Yield was 0.366 g (35%). m/z 596, 598 ($MH^+$); $^1$H-NMR (300 MHz) δ 0.35 (d, 3H), 0.66-0.77 (m, 1H), 0.93 (d, 3H), 0.18-1.27 (m, 1H), 1.65-1.85 (m, 2H), 1.80 (s, 6H), 2.66-2.76 (m, 1H), 2.89 (s, 3H), 3.30-3.41 (m, 2H), 5.20 (d, 1H), 5.73 (d, 1H), 6.15 (d, 1H), 7.20 (d, 2H), 7.28-7.41 (m, 5H), 7.56b (d, 2H).

Methods 39a-b

The following compounds were synthesized according to Method 39:

| Method # | Compound Name | m/z | SM |
|---|---|---|---|
| 39a | N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-methyl-benzamide | 532 ($MH^+$) | Method 38a |
| 39b | N-[1-(5-Benzyl-3-methyl-4-oxo-4,5-dihydro-isothiazolo[5,4-d]pyrimidin-6-yl)-2-methyl-propyl]-N-(3- | 540 ($MH^+$) | Method 38b |

Methods 40-40b

The following compounds were chirally purified in same manner as (+) (3-[[1-(5-benzyl-3-methyl-4-oxo-4,5-dihydro-isothiazolo[5,4-d]pyramidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 40 | (+) N-[1-(5-Benzyl-3-methyl-4-oxo-4,5-dihydro-isothiazolo[5,4-d]pyrimidin-6-yl)-2-methyl-propyl]-4-bromo-N-(3-dimethylamino-propyl)-benzamide Example E-2 | Chiralpak AD | 85% hexanes 15% isopropanol 0.1% diethylamine | 7.6 min | Method 39 |
| 40a | (+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-methyl-benzamide Example E-1 | Chiralpak AD | 90% hexanes 10% isopropanol 0.1% diethylamine | 7.7 min | Method 39a |
| 40b | (+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-3-fluoro-4-methyl-benzamide Example E-3 | Chiralpak AD | 90% hexanes 10% isopropanol 0.1% diethylamine | 7.5 min | Method 39b |

Method 41

3-Methyl-5-(3-methyl-butyryl)-isoxazole-4-carboxylic acid amide

A mixture of 5-amino-3-methyl-isoxazole-4-carboxylic acid amide (10 g, 70 mmol) in 25 ml of isovaleric anhydride was stirred at 110-145° C. for 1 h. The brown solution was diluted with hexane (500 ml) and cooled down. The precipitated gum was separated from the mixture and washed with hexane, dried in vacuo. 3-Methyl-5-(3-methyl-butyryl)-isoxazole-4-carboxylic acid amide was obtained as a yellow gum. Further used without purification in method 42.

Method 42

6-Isobutyl-3-methyl-5H-isoxazolo[5,4-d]pyramidin-4-one

A suspension of 3-methyl-5-(3-methyl-butyryl)-isoxazole-4-carboxylic acid amide (method 41) (split into 40 vials) in 3.5 ml of 2N NaOH aq was subjected to microwave irradiation at 140° C. for 20 min. The resulting solution was cooled with an ice bath, and the pH was adjusted to 1~3 with concentrated HCl. The solid was filtered, washed with water, dried over vacuum at 40° C. overnight. 6-Isobutyl-3-methyl-5H-isoxazolo[5,4-d]pyramidin-4-one (8 g) was obtained white solid. 55% yield for two steps. m/z: 208 (MH$^+$), $^1$H NMR (DMSO-d$_6$): 0.76 (d, 6H), 1.95 (m, 1H), 2.25 (s, 3H), 2.32 (d, 2H), 12.55 (s, 1H).

Method 43

5-Benzyl-6-isobutyl-3-methyl-5H-isoxazolo[5,4-d]pyramidin-4-one

A suspension of 6-isobutyl-3-methyl-5H-isoxazolo[5,4-d]pyramidin-4-one (method 42) (5 g, 24.4 mmol), benzylbromide (4.17 g, 24.4 mmol), potassium carbonate (6.7 g, 48.8 mmol) in 20 ml DMF was stirred at room temperature for 2 days. The mixture was diluted with water, extracted with EtOAc (100 ml×3), the combined organic phases were dried, concentrated, purified by flash column chromatography (elute: hexane-EtOAc=7:1). 5-benzyl-6-isobutyl-3-methyl-5H-isoxazolo[5,4-d]pyramidin-4-one was obtained as white solid (3 g, 10.1 mmol) (41%). m/z: 298 (MH$^+$), $^1$H NMR (DMSO-d$_6$): 0.90 (d, 6H), 2.30 (m, 1H), 2.55 (s, 3H), 2.75 (d, 2H), 5.42 (s, 2H), 7.22-7.43 (m, 5H).

Methods 43a-b

The following compounds were synthesized according to Method 43:

| Method # | Compound Name | m/z |
|---|---|---|
| 43a | 5-(4-Fluoro-benzyl)-6-isobutyl-3-methyl-5H-isoxazolo[5,4-d]pyrimidin-4-one | 316 (MH$^+$) |
| 43b | 5-(3-Fluoro-benzyl)-6-isobutyl-3-methyl-5H-isoxazolo[5,4-d]pyrimidin-4-one | 316 (MH$^+$) |

Method 44

5-Benzyl-6-(1-bromo-2-methyl-propyl)-3-methyl-5H-isoxazolo[5,4-d]pyramidin-4-one A solution of 5-benzyl-6-isobutyl-3-methyl-5H-isoxazolo[5,4-d]pyramidin-4-one (method 43) (130 mg, 0.44 mmol) and sodium acetate (90 mg, 1.09 mmol, 2.5 eq) in glacial acetic acid (2 ml) was treated with a preformed bromine solution (0.7 ml bromine in 10 ml of glacial acetic acid) (1.54 ml, 2 mmol). The mixture was stirred at 110-120° C. for 1 day. Excess bromine (1.54 ml, 2 mmol) was added to the mixture every 4 hours for two times at 110-120° C. Water was added to the mixture to which was subsequently added potassium carbonate and extracted with DCM (20 ml×3), the combined organic phases were washed with water and dried, then concentrated to give the crude product which was purified by ISCO (elute: hexane-EtOAc). 100 mg (60%) of 5-benzyl-6-(1-bromo-2-methyl-propyl)-3-methyl-5H-isoxazolo[5,4-d]pyramidin-4-one was obtained as a yellow gum. m/z: 376, 378 (MH$^+$), $^1$H NMR (DMSO-d$_6$): 0.55 (d, 3H), 1.02 (d, 3H), 2.48 (m, 4H), 4.75 (d, 1H), 5.60 (d, 1H), 5.70 (d, 1H), 7.16-7.30 (m, 5H).

Methods 44a-b

The following compounds were synthesized according to Method 44:

| Method # | Compound Name | m/z | SM |
|---|---|---|---|
| 44a | 6-(1-Bromo-2-methyl-propyl)-5-(4-fluoro-benzyl)-3-methyl-5H-isoxazolo[5,4-d]pyrimidin-4-one | 394, 396 (MH$^+$) | Method 43a |
| 44b | 6-(1-Bromo-2-methyl-propyl)-5-(3-fluoro-benzyl)-3-methyl-5H-isoxazolo[5,4-d]pyrimidin-4-one | 394, 396 (MH$^+$) | Method 43b |

Method 45

6-(1-Azido-2-methyl-propyl)-5-benzyl-3-methyl-5H-isoxazolo[5,4-d]pyramidin-4-one A suspension of 5-benzyl-6-(1-bromo-2-methyl-propyl)-3-methyl-5H-isoxazolo[5,4-d]pyramidin-4-one (method 44) (100 mg, 0.266 mmol) and sodium azide (34.5 mg, 0.53 mmol) in DMF (2 ml) was stirred at 60° C. for 1 h. Water (5 ml) was added to the mixture and then extracted with EtOAc (3×20 ml). The combined organic phases were washed with brine (10 ml), dried, concentrated to obtain 6-(1-azido-2-methyl-propyl)-5-benzyl-3-methyl-5H-isoxazolo[5,4-d]pyrimidin-4-one which was purified by ISCO (Hexane-EtOAc). 50 mg (56%) of a colorless oil was obtained. m/z: 339 (MH$^+$), $^1$H NMR (DMSO-d$_6$): 0.60 (d, 3H), 0.95 (d, 3H), 2.25 (m, 1H), 2.45 (s, 3H), 4.19 (d, 1H), 5.30 (d, 1H), 5.42 (d, 1H), 7.12-7.30 (m, 5H).

Methods 45a-b

The following compounds were synthesized according to Method 45:

| Method # | Compound Name | m/z | SM |
|---|---|---|---|
| 45a | 6-(1-Azido-2-methyl-propyl)-5-(4-fluoro-benzyl)-3-methyl-5H-isoxazolo[5,4-d]pyrimidin-4-one | 357 (MH$^+$) | Method 44a |
| 45b | 6-(1-Azido-2-methyl-propyl)-5-(3-fluoro-benzyl)-3-methyl-5H-isoxazolo[5,4-d]pyrimidin-4-one | 357 (MH$^+$) | Method 44b |

Method 46

6-(1-Amino-2-methyl-propyl)-5-benzyl-3-methyl-5H-isoxazolo[5,4-d]pyrimidin-4-one A mixture of 6-(1-azido-2-methyl-propyl)-5-benzyl-3-methyl-5H-isoxazolo[5,4-d]pyrimidin-4-one (method 45) (40 mg, 1.118 mmol), triphenylphosphine (62 mg, 0.237 mmol) and water (4 µl) in THF was stirred at 60° C. for 5 hours. Excess amount of water (30 µl) was added to the mixture and stirred at 60° C. for another 10 hours. The volatile solvent was distilled out, the crude product was purified by ISCO (EtOAc: hexane=60%. 25 mg (68%) of 6-(1-amino-2-methyl-propyl)-5-benzyl-3-methyl-5H-isoxazolo[5,4-d]pyrimidin-4-one was obtained as colorless oil. m/z: 313 (MH$^+$), $^1$H NMR (DMSO-d$_6$): 0.55 (d, 3H), 0.95 (d, 3H), 2.02 (m, 1H), 2.15 (br, 2H), 2.55 (s, 3H), 3.59 (d, 1H), 5.38 (d, 1H), 5.65 (d, 1H), 7.25-7.42

Methods 46a-b

The following compounds were synthesized according to Method 46:

| Method # | Compound Name | m/z | SM |
|---|---|---|---|
| 46a | 6-(1-Amino-2-methyl-propyl)-5-(4-fluoro-benzyl)-3-methyl-5H-isoxazolo[5,4-d]pyrimidin-4-one | 331 (MH$^+$) | Method 45a |
| 46b | 6-(1-Amino-2-methyl-propyl)-5-(3-fluoro-benzyl)-3-methyl-5H-isoxazolo[5,4-d]pyrimidin-4-one | 331 (MH$^+$) | Method 45b |

Method 47

{3-[1-(5-Benzyl-3-methyl-4-oxo-4,5-dihydro-isoxazolo[5,4-d]pyrimidin-6-yl)-2-methyl-propylamino]-propyl}-carbamic acid tert-butyl ester A mixture of 6-(1-amino-2-methyl-propyl)-5-benzyl-3-methyl-5H-isoxazolo[5,4-d]pyrimidin-4-one (method 46) (20 mg, 0.064 mmol) and (3-oxo-propyl)-carbamic acid tert-butyl ester (11 mg, 0.064 mmol) in DCM (5 ml) with dried 4 ÅMS was stirred for 1 h at room temperature. Then sodium triacetoxyborohydride (2eq) and 1 drop of acetic acid were added to the mixture. The mixture was stirred at room temperature for 1 day. The mixture was filtered through a 2μ cartridge, the filtrate was concentrated, the crude mixture was purified by ISCO (elute: EtOAc-hexane=30%~60%) to give 18 mg (60%) of {3-[1-(5-benzyl-3-methyl-4H-oxo-4,5-dihydro-isoxazolo[5,4-d]pyrimidin-6-yl)-2-methyl-propylamino]-propyl}-carbamic acid tert-butyl ester as a white solid. m/z: 470 (MH$^+$), $^1$H NMR (DMSO-d$_6$): 0.65 (d, 3H), 0.80 (d, 3H), 1.10 (m, 2H), 1.25 (s, 9H), 1.32 (d, 1H), 1.70-1.90 (m, 2H), 2.18 (m, 1H), 2.49 (s, 3H), 2.70 (m, 2H), 3.48 (d, 1H), 5.15 (d, 1H), 5.51 (d, 1H), 6.55 (br, 1H), 7.12-7.32 (m, 5H).

Methods 47a-b

The following compounds were synthesized according to Method 47:

| Method # | Compound Name | m/z | SM |
|---|---|---|---|
| 47a | (3-{1-[5-(4-Fluoro-benzyl)-3-methyl-4-oxo-4,5-dihydro-isoxazolo[5,4-d]pyrimidin-6-yl]-2-methyl-propylamino}-propyl)-carbamic acid tert-butyl ester | 488 (MH$^+$) | Method 46a |
| 47b | (3-{1-[5-(3-Fluoro-benzyl)-3-methyl-4-oxo-4,5-dihydro-isoxazolo[5,4-d]pyrimidin-6-yl]-2-methyl-propylamino}-propyl)-carbamic acid tert-butyl ester | 488 (MH$^+$) | Method 46b |

Method 48

{3-[[1-(5-Benzyl-3-methyl-4-oxo-4,5-dihydro-isoxazolo[5,4-d]pyrimidin-6-yl)-2-methyl-propyl]-(4-methyl-benzoyl)-amino]-propyl}-carbamic acid tert-butyl ester A solution of {3-[1-(5-benzyl-3-methyl-4-oxo-4,5-dihydro-isoxazolo[5,4-d]pyrimidin-6-yl)-2-methyl-propylamino]-propyl}-carbamic acid tert-butyl ester (method 47) (100 mg, 0.213 mmol) in DCM (4 ml) was added p-toluoyl chloride (66 mg, 0.426 mmol) followed by triethylamine (65 mg, 0.639 mmol). The mixture was stirred at 30-40° C. for 2 days. The mixture was then diluted with DCM, washed with saturated sodium bicarbonate aq. The organic phase was dried, filtered, and concentrated. The crude oil was purified by ISCO (solvent: EtOAc-hexane) to give {3-[[1-(5-benzyl-3-methyl-4-oxo-4,5-dihydro-isoxazolo[5,4-d]pyrimidin-6-yl)-2-methyl-propyl]-(4-methyl-benzoyl)-amino]-propyl}-carbamic acid tert-butyl ester as white solid (115 mg, 0.196 mmol). m/z: 588 (MH$^+$).

Methods 48a-b

The following compounds were synthesized according to Method 48:

| Method # | Compound Name | m/z | SM | Acylating agent |
|---|---|---|---|---|
| 48a | {3-[{1-[5-(4-Fluoro-benzyl)-3-methyl-4-oxo-4,5-dihydro-isoxazolo[5,4-d]pyrimidin-6-yl]-2-methyl-propyl}-(4-methyl-benzoyl)-amino]-propyl}-carbamic acid tert-butyl ester | 606 (MH$^+$) | Method 47a | 4-methyl-benzoyl chloride |
| 48b | {3-[{1-[5-(3-Fluoro-benzyl)-3-methyl-4-oxo-4,5-dihydro-isoxazolo[5,4-d]pyrimidin-6-yl]-2-methyl-propyl}-(4-methyl-benzoyl)-amino]-propyl}-carbamic acid tert-butyl ester | 606 (MH$^+$) | Method 47b | 4-methyl-benzoyl chloride |

Method 49

Chiral Purification of (+) {3-[{1-[5-(3-Fluoro-benzyl)-3-methyl-4-oxo-4,5-dihydro-isoxazolo[5,4-d]pyrimidin-6-yl]-2-methyl-propyl}-(4-methyl-benzoyl)-amino]-propyl}-carbamic acid tert-butyl ester The following compound was chirally purified in same manner as (+) (3-[[1-(5-benzyl-3-methyl-4-oxo-4,5-dihydro-isothiazolo[5,4-d]pyrimidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 49 | (+) {3-[{1-[5-(3-Fluoro-benzyl)-3-methyl-4-oxo-4,5-dihydro-isoxazolo[5,4-d]pyrimidin-6-yl]-2-methyl-propyl}-(4-methyl-benzoyl)-amino]-propyl}-carbamic acid tert-butyl ester | Chiralpak AD | 80% hexane 20% isopropanol 0.1% diethylamine | 7.4 min | Method 48b |

Method 50

N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide hydrogen chloride A solution of {3-[[1-(5-benzyl-3-methyl-4-oxo-4,5-dihydro-isoxazolo[5,4-d]pyrimidin-6-yl)-2-methyl-propyl]-(4-methyl-benzoyl)-amino]-propyl}-carbamic acid tert-butyl ester (method 48) (0.058 g, 0.1 mmol) in 3 ml of 4 M HCl in dioxane was stirred at room temperature for 2 hr. The solvent was distilled off by vacuo, the residue was dried at 40~50° C. for overnight under vacuum. N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide was obtained as the HCl salt. Yield was 0.046 g (88%). m/z 488 (MH$^+$), $^1$H NMR (500 MHz, 100° C., DMSO-d$_6$): 0.48 (d, 3H), 0.94 (d, 3H), 1.30 (m, 1H), 1.60 (m, 1H), 2.35 (m, 2H), 2.38 (s, 3H), 2.58 (s, 3H), 2.70 (m, 1H), 3.37 (m, 2H), 5.11 (d, 1H), 5.64 (d, 1H), 5.90 (d, 1H), 7.23-7.39 (m, 9H), 7.63 (br, 3H).

Methods 50a-b

The following compounds were synthesized according to Method 50:

| Method # | Compound Name | m/z | SM |
|---|---|---|---|
| 50a | N-(3-Amino-propyl)-N-{1-[5-(4-fluoro-benzyl)-3-methyl-4-oxo-4,5-dihydro-isoxazolo[5,4-d]pyrimidin-6-yl]-2-methyl-propyl}-4-methyl-benzamide hydrogen chloride | 506 (MH$^+$) | Method 48a |
| 50b | (+) N-(3-Amino-propyl)-N-{1-[5-(3-fluoro-benzyl)-3-methyl-4-oxo-4,5-dihydro-isoxazolo[5,4-d]pyrimidin-6-yl]-2-methyl-propyl}-4-methyl-benzamide hydrogen chloride Example F-3 | 506 (MH$^+$) | Method 49 |

Methods 51 and 51a

The following compounds were chirally purified in same manner as (+) (3-[[1-(5-benzyl-3-methyl-4-oxo-4,5-dihydro-isothiazolo[5,4-d]pyrimidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 51 | (+) N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide Example F-1 | Chiralpak AD | 60% hexanes 40% isopropanol 0.1% diethylamine | 7.9 min | Method 50 |
| 51a | (+) N-(3-Amino-propyl)-N-{1-[5-(4-fluoro-benzyl)-3-methyl-4-oxo-4,5-dihydro-isoxazolo[5,4-d]pyrimidin-6-yl]-2-methyl-propyl}-4-methyl-benzamide Example F-2 | Chiralpak AD | 60% hexanes 40% isopropanol 0.1% diethylamine | 7.5 min | Method 50a |

Method 52

3-Amino-2-thioformyl-but-2-enoic acid ethyl ester

To an ice cold solution of phosphoryl chloride (20 mL, 220 mmol), anhydrous DMF (60 mL) was added dropwise and the resulting solution was added dropwise during 30 min to a stirred solution of the ethyl crotonate (25.83 g, 200 mmol) in anhydrous THF (400 mL) with the temperature maintained at 0° C. The resulting mixture was allowed to warm to room temperature and stirred overnight and then for 4 h at 30° C.; it was then allowed to stand overnight in a refrigerator. Addition of ether (200 mL) resulted in a yellow oil from which the ether layer was decanted. The resulting oil was washed several times with ether until the ether layer became clear. The oily product was dissolved in DCM (800 mL) and was vigorously shaken with aqueous sodium hydrogen sulfide (2M; 500 mL). The organic layer was separated and the aqueous layer washed with DCM (100 mL). The combined organic layers were washed with water (600 mL), brine (400 mL), dried ($Na_2SO_4$) and concentrated to get orange crystals. The thus obtained product was triturated with DCM/hexanes to get pure product as orange crystals (25.6 g, 74%). $^1$H NMR (300 MHz) δ: 1.33 (t, 3H), 2.57 (s, 3H), 4.23 (q, 2H), 6.83 (bs, 1H), 10.97 (s, 1H), 13.93 (s, 1H).

Method 53

3-Methyl-isothiazole-4-carboxylic acid ethyl ester

To a solution of 3-amino-2-thioformyl-but-2-enoic acid ethyl ester (method 52) (25.6 g, 147 mmol) in ethanol (300 mL), was added m-chloroperbenzoic acid (33.3 g, 77%, 149 mmol) in ethanol (200 mL) dropwise with stirring at room temperature. After the completion of the addition the reaction mixture was heated at 75° C. for 2 h after which the MS showed the complete disappearance of the starting material. The reaction mixture was diluted with ether (500 mL) and the ethereal solution was washed with 0.1 M NaOH solution (3×500 mL) and once with water (400 mL) dried ($Na_2SO_4$) and concentrated to get the pure product as light brown oil. Yield 23.5 g (93%). $^1$NMR (300 MHz) δ: 1.40 (t, 3H), 2.73 (s, 3H), 5.07 (t, 1H), 4.36 (q, 2H), 9.24 (s, 1H).

Method 54

3-Methyl-isothiazole-4-carboxylic acid

To a solution of 3-methyl-isothiazole-4-carboxylic acid ethyl ester (method 53) (23.3 g, 136 mmol) in THF (200 mL) aqueous NaOH (6.5 g, 162 mmol, in 100 ml of water) was added and the mixture was stirred at room temperature for 16 h. The TLC of the reaction mixture showed the complete disappearance of the starting material. The reaction mixture was cooled in an ice bath and acidified to pH 5 using 6M HCl and the resultant mixture was extracted with ether (3×100 mL). The ether layers were combined, washed with water (100 mL), brine (100 mL), dried ($Na2SO_4$) and concentrated to about 10 mL. Addition of hexanes to the above mixture resulted in the precipitation of the product which was filtered off, washed with hexanes and dried to provide the pure product as a tan powder. Yield 15.3 g (79%). $^1$H NMR (300 MHz) δ 2.39 (s, 3H), 8.98 (s, 1H).

Method 55

(3-Methyl-isothiazol-4-yl)-carbamic acid tert-butyl ester

To a solution of 3-methyl-isothiazole-4-carboxylic acid (method 54) (14.8 g, 103 mmol) in anhydrous t-BuOH (100 mL) triethyl amine (10.5 g, 104 mmol) was added followed by the dropwise addition of diphenylphosphoryl azide (28.6 g, 104 mmol) and the resulting mixture was heated at reflux overnight after which the TLC showed the complete disappearance of the starting material. The reaction mixture was cooled to room temperature and poured into ice cold water (500 mL). The aqueous layer was extracted with ether (3×100 mL) and the combined organic layers were washed with satd, $NaHCO_3$ (100 mL), brine (100 mL) and dried ($Na_2SO_4$). Concentration of the ether solution provided the crude product which was purified by column chromatography to get the pure product as light brown crystals. Yield 21.4 g (97%). $^1$H NMR (300 MHz) δ 1.53 (s, 9H), 2.40 (s, 3H), 6.50 (s, 1H), 8.66 (s, 1H).

Method 56

4-tert-Butoxycarbonylamino-3-methyl-isothiazole-5-carboxylic acid

To a solution of (3-methyl-isothiazol-4-yl)-carbamic acid tert-butyl ester (method 55) (21.4 g, 100 mmol) in anhydrous THF (200 mL) at -78° C., LDA (139 mL, 1.8 M solution, 250 mmol) was added dropwise over a period of 1 h. The reaction mixture was stirred at that temperature for a further 3 h after which powdered dry ice was added and the reaction slowly allowed to warm to room temperature overnight. The reaction mixture was quenched by adding saturated $NH_4Cl$ solution and extracted with ether (3×100 mL) and the combined ether layers were back extracted with satd. $NaHCO_3$ (3×100 mL). The aqueous layers were combined and acidified to pH 5 using 6M HCl and extracted with ether (4×100 mL). The combined ether layers were dried ($Na_2CO_3$) and concentrated to give the pure acid as an off white powder. Yield 11 g (39%). $^1$H NMR (300 MHz) δ 1.47 (s, 9H), 2.44 (s, 3H), 8.53 (bs, 1H), 9.68 (bs, 1H).

Method 57

4-Amino-3-methyl-isothiazole-5-carboxylic acid 4-tert-Butoxycarbonylamino-3-methyl-isothiazole-5-carboxylic acid (method 56) (11 g, 45 mmol) was dissolved in 50 mL of 4M solution of HCl in 1,4-dioxane (200 mmol) and the resulting solution was stirred at room temperature overnight. The TLC showed the complete disappearance of the starting acid. The reaction was concentrated and the residue was triturated with ether and the precipitated hydrochloride salt was filtered off and washed with ether and dried to provide the product as a light brown powder. Yield 8.2 g (100%). $^1$H NMR (300 MHz, DMSO-$d_6$) δ 2.30 (s, 3H), 8.85 (bs, 3H).

Method 58

3-Methyl-5-propyl-isothiazolo[4.5-d][1,3]oxazin-7-one

To a solution of 4-amino-3-methyl-isothiazole-5-carboxylic acid (method 57) (2.91 g, 15 mmol) in pyridine (20 mL) at 0° C., was added dropwise a solution of butyryl chloride (3.18 g, 30 mmol) in chloroform (30 mL). The reaction mixture was allowed to warm to room temperature and stirred overnight. Chloroform (200 mL) was added to the reaction mixture followed by 2M HCl (200 mL) and the mixture was stirred. The chloroform layer was further washed with 2M HCl (100 mL), water (100 mL), brine (100 mL) and concentrated. Column purification of the thus obtained crude product provided the pure product as light brown solid. Yield 2 g (64%). $^1$H NMR (300 MHz) δ 1.03 (t, 3H), 1.80-1.92 (m, 2H), 2.65 (s, 3H), 2.76 (t, 2H).

Method 59

6-Benzyl-3-methyl-5-propyl-6H-isothiazolo[4,5-d]pyrimidin-7-one

3-Methyl-5-propyl-isothiazolo[4,5-d][1,3]oxazin-7-one (method 58) (200 mg, 1.02 mmol) was taken in a 10 mL microwavable pyrex tube and benzyl amine (1 g, 9.34 mmol) was added to it. The resulting mixture was heated in a microwave synthesizer (CEM's Discoverer) at 200° C. for 20 min. The MS of the reaction mixture showed the complete disappearance of the starting material and the presence of the product peak at 286 ($MH^+$). The reaction mixture was diluted with 1N HCl (10 mL) and extracted with EtOAc (2×30 mL). The combined EtOAc layers were washed with water, brine, dried and concentrated. The thus obtained crude product was purified by column chromatography to isolate the pure product as a white solid. Yield 208 mg (71%). $^1$H NMR (300 MHz) δ 0.98 (t, 3H), 1.76-1.88 (m, 2H), 2.68 (s, 3H), 2.74 (t, 2H), 5.42 (s, 2H), 7.10-7.19 (m, 2H), 7.28-7.39 (m, 3H).

Method 60

6-Benzyl-5-(1-bromo-propyl)-3-methyl-6H-isothiazolo[4,5-d]pyrimidin-7-one

To a solution of 6-benzyl-3-methyl-5-propyl-6H-isothiazolo[4,5-d]pyrimidin-7-one (method 59) (208 mg, 0.69 mmol) and sodium acetate (0.5 g, 5 mmol) in acetic acid (10 mL) at 100° C., a solution of the bromine (0.232 g, 1.46 mmol) in acetic acid (20 mL) was added dropwise [The next drop of Bromine was added only after the previous drop had reacted completely by monitoring the decolorization] over a period of 30 min. The reaction mixture was cooled after the addition and the TLC (eluent 10% EtOAc in hexanes) and MS showed the complete disappearance of the SM and only the product. The reaction mixture was poured into ice water and extracted with EtOAc (3×30 mL) and the organic layers were combined and washed with 2% sodium thiosulfate solution (30 mL), water (50 mL), brine (50 mL) and dried ($Na_2SO_4$). Concentration of the organic layer provided the product and it was pure enough to be used in the next step. Yield 260 mg (99%). $^1$H NMR (300 MHz) δ 0.77 (t, 3H), 2.20-2.54 (m, 2H), 2.70 (s, 3H), 4.67 (t, 1H), 4.95 (d, 1H), 6.25 (d, 1H) 7.10-7.19 (m, 2H), 7.30-7.39 (m, 3H).

Method 61

N-(3-Amino-propyl)-N-[1-(6-benzyl-3-methyl-7-oxo-6,7-dihydro-isothiazolo[4,5-d]pyrimidin-5-yl)-propyl]-4-methyl-benzamide hydrogen chloride To a solution of 6-benzyl-5-(1-bromo-propyl)-3-methyl-6H-isothiazolo[4,5-d]pyrimidin-7-one (method 60) (260 mg, 0.70 mmol) in anhydrous DMF (10 mL), ethyl diisopropylamine (387 mg, 3 mmol) and N-(3-aminopropyl)carbamic acid tert-butyl ester (174 mg, 1 mmol) were added at room temperature and the mixture was stirred at room temperature for 1 h after which the MS analysis showed the complete disappearance of the starting bromide and only the product peak at 472 ($MH^+$) was observed. The reaction mixture was diluted with water (100 mL) and extracted with EtOAc (3×60 mL). The combined organic extracts were dried and concentrated to get the crude amine which was dissolved in chloroform (40 mL) and diisopropylethylamine (387 mg, 3 mmol) was added and the mixture was heated to 60° C. To the stirred hot solution p-toluoyl chloride (154 mg, 1 mmol) in chloroform (20 mL) was added dropwise and the mixture was refluxed for 12 h after which the MS showed the complete disappearance of the amine and only the product peak at 590 ($MH^+$). The reaction mixture was concentrated and the crude product was purified by column chromatography to isolate the pure acylated product (80 mg, 20% overall from bromide) which was treated with 4M HCl in 1,4-dioxane (10 mL) for 30 min. The dioxane was evaporated in a rotary evaporator and the residue was dissolved in water and freeze dried to get the pure product as a white fluffy solid. Yield 60 mg (16% overall from bromide). m/z 490 ($MH^+$); $^1$H NMR (300 MHz, DMSO-d₆, 96° C.) δ 0.65 (t, 3H), 1.36-1.50 (m, 1H), 1.60-1.72 (m, !H), 1.88-1.99 (m, 1H), 2.14-2.26 (m, 1H), 2.35 (s, 3H), 2.47 (t, 2H), 2.68 (s, 3H), 3.32-3.44 (m, 2H), 4.90 (d, 1H), 5.50 (bs, 1H), 5.76 (d, 1H), 6.96-7.34 (m, 9H), 7.68 (bs, 3H).

Method 62

Chiral purification of (+) N-(3-Amino-propyl)-N-[1-(6-benzyl-3-methyl-7-oxo-6,7-dihydro-isothiazolo[4,5-d]pyrimidin-5-yl)-propyl]-4-methyl-benzamide The following compound was chirally purified in same manner as (+) (3-[[1-(5-benzyl-3-methyl-4-oxo-4,5-dihydro-isothiazolo[5,4-d]pyrimidin-6-yl)-propyl]-(4-methyl-benzoyl)-amino]-propyl)-carbamic acid tert-butyl ester (method 12). Chiral purification generally resulted in 99% purity of the (+) enantiomer.

| Method # | Compound Name | Column Type | Solvent composition | (+) Enantiomer retention time | SM |
|---|---|---|---|---|---|
| 62 | (+) N-(3-Amino-propyl)-N-[1-(6-benzyl-3-methyl-7-oxo-6,7-dihydro-isothiazolo[4,5-d]pyrimidin-5-yl)-propyl]-4-methyl-benzamide Example G-1 | Chiralpak AD | 70% hexane 30% isopropanol 0.1% diethylamine | 11.7 min | Method 61 |

Alternative Procedures to Prepare Certain Starting Materials

Method 1

2-(1-Ethoxy-ethylidene)-malononitrile (alternative procedure)

Triethyl orthoacetate (1.6 L, 9 mol), malononitrile (500 g, 7.57 mol) and glacial acetic acid (25 ml) were placed in a 5 l RB flask equipped with a stirrer, thermometer and a Vigreux column (20×1 in.) on top of which a distillation condenser was placed. The reaction mixture was heated and ethyl alcohol began to distil when the temperature of the reaction mixture was about 85-90° C. After about 3 h., the temperature of the reaction mixture reached 140° C. Then the reaction was concentrated in a rotary evaporator to remove the low-boiling materials and the residue was stirred with isopropyl alcohol (1 l) and cooled in an ice bath. The crystallized product was filtered off washed with isopropyl alcohol (200 ml), hexanes (600 ml) and dried at 50° C. in a vacuum oven overnight to yield 2-(1-ethoxy-ethylidene)-malononitrile (974 g, 94%) as a golden yellow solid [mp 92.° C. (lit.90-92° C., MCCall. M. A. *J. Org. Chem.* 1962, 27, 2433-2439.)].

Method 2

(2E)-2-Cyano-3-ethoxybut-2-enethioamide (alternative procedure)

2-(1-Ethoxy-ethylidene)-malononitrile (method 1) (300 g, 2.2 mol) was dissolved in anhydrous benzene (3.1 l, slight warming required) and 20 ml of triethylamine was added. The mixture was mechanically stirred and hydrogen sulfide was bubbled into this solution for 2 h and a solid formed. Then N₂ was bubbled through the reaction mixture for 40 min. The precipitated solid was filtered off, washed with cold benzene (200 ml) and dried in a vacuum oven overnight to isolate (2E)-2-cyano-3-ethoxybut-2-enethioamide (332 g, 88%) as light brown crystals.

Method 3

(2E)-3-Amino-2-cyanobut-2-enethioamide (alternative procedure)

(2E)-2-Cyano-3-ethoxybut-2-enethioamide (method 2) (150 g, 0.88 mol) was dissolved in 7M solution of ammonia in methanol (2.9 L) and stirred at r.t. overnight. The reaction mixture was concentrated and the residue was crystallized from hot water (1. L) to provide (2E)-3-amino-2-cyanobut-2-enethioamide (111.6 g, 89%) as brown crystals. ¹H NMR (300 MHz, DMSO-d6) δ 2.22 (s, 3H), 7.73 (bs, 1H), 8.53 (bs, 1H), 9.01 (bs, 1H), 11.60 (bs, 1H).

Method 4

5-Amino-3-methylisothiazole-4-carbonitrile (alternative procedure)

To a stirred solution of (2E)-3-amino-2-cyanobut-2-enethioamide (method 3) (111 g, 0.78 mol) in methanol (2 L) was added dropwise 200 ml of 35% hydrogen peroxide over a period of 30 min. After the completion of the addition the mixture was stirred at 60° C. for 3 h after which the TLC showed the completion of the reaction. The reaction mixture was evaporated to 300 ml in a rotary evaporator and cooled in an ice-bath. The crystallized product was filtered off and washed with isopropyl alcohol (100 ml) and dried in vacuum at 50° C. overnight to provide 5-amino-3-methylisothiazole-4-carbonitrile (105.63 g, 96%) as a light yellow crystalline solid. ¹H NMR (300 MHz, DMSO-d₆) δ 2.24 (s, 3H), 8.00 (bs, 2H).

Method 24

N-(4-Cyano-3-methyl-isothiazol-5-yl)-3-methyl-butyramide (alternative procedure)

To a solution of 5-amino-3-methylisothiazole-4-carbonitrile (method 4) (105.6 g, 0.76 mol) in pyridine (250 ml) at 0° C., isovaleryl chloride (100 g, 0.83 mol) in chloroform (300 ml) was added dropwise. After the completion of the addition the reaction mixture was allowed to warm to r.t. and stirred overnight. The TLC and the MS showed the complete disappearance of the starting material and the reaction mixture was diluted with CHCl₃ (600 ml), washed with water (200 ml), 2N HCl (600 ml), satd. NaHCO₃ (200 ml), brine (200 ml) and dried over Na₂SO₄Concentration of the CHCl₃ layer provided the crude product which was triturated from DCM/hexanes (⅒) and filtered off to isolate N-(4-cyano-3-methylisothiazol-5-yl)-3-methyl-butyramide (149.7 g, 88%) as an off-white crystalline solid. $^1$H NMR (300 MHz) δ 1.04 (d, 6H), 2.18-2.32 (m, 1H), 2.46 (d, 2H), 2.53 (s, 3H), 9.87 (bs, 1H).

Method 25

3-Methyl-5-(3-methyl-butlrylamino)-isothiazole-4-carboxylic acid amide (alternative procedure)

To a solution of N-(4-cyano-3-methyl-isothiazol-5-yl)-3-methyl-butyramide (method 24) (72 g, 322 mmol) in 30% aqueous NH$_4$OH (2.1 L), was added dropwise 1.3 L of hydrogen peroxide at 40° C. After 20 min the temperature of the reaction mixture rose to 60° C. The addition was completed in 1.5 h. After an additional 2 h the MS showed the completion of the reaction. The reaction mixture was cooled in ice and con HCl was slowly added with cooling till the pH of the reaction mixture turns 7.6. The precipitated product was filtered and dried in vacuum oven to get the pore amide (36 g, 46%). The filtrate was saturated with NaCl and extracted with super solvent (34:66, t-butanol: 1,2-dichloroethane) and the combined organic extracts were washed with water (500 ml), brine (600 ml) and dried (Na$_2$SO$_4$) and concentrated. The residue on trituration with EtOAc/hexanes (¼) provided an additional 9.8 g of pure product. Total yield of 45.8 g (58%) 3-methyl-5-(3-methyl-butyrylamino)-isothiazole-4-carboxylic acid amide. $^1$H NMR (300 MHz) δ 1.03 (d, 6H), 2.24 (m, 1H), 2.43 (d, 2H), 2.69 (s, 3H), 5.98 (bs, 2H), 11.77 (bs, 1H).

Method 26

6-Isobutyl-3-methyl-5H-isothiazolo[5,4-d]pyrimidin-4-one (alternative procedure)

The 3-methyl-5-(3-methyl-butyrylamino)-isothiazole-4-carboxylic acid amide (method 25) (45.8 g, 190 mmol) was suspended in 700 ml of 30% NH$_3$ and then was heated to 140° C. for 5 h in a pressure reactor. The mixture was poured into a 4 L beaker and cooled in an ice bath. To the cold solution con HCl (560 ml) was added dropwise to pH 7.5 and a white precipitate was formed. The precipitated product was filtered off, washed with water (100 ml) and dried under vacuum overnight. 6-Isobutyl-3-methyl-5H-isothiazolo[5,4-d]pyrimidin-4-one (11 g, 26%) was isolated as an off-white powder. $^1$H NMR (300 MHz) δ 1.05 (d, 6H), 2.32 (m, 1H), 2.69 (d, 2H), 2.82 (s, 3H).

Method 27

5-Benzyl-6-isobutyl-3-methyl-5H-isothiazolo[5,4-d]pyrimidin-4-one (alternative procedure)

To a solution of the 6-isobutyl-3-methyl-5H-isothiazolo[5,4-d]pyrimidin-4-one (method 26) (11 g, 49 mmol) in 60 ml of anhydrous DMF at 0° C., was added 13.8 g (100 mmol) of anhydrous K$_2$CO$_3$ followed by benzyl bromide (9.3 g, 54 mmol) and the mixture was stirred at 0-20° C. overnight. The TLC of the reaction mixture showed the complete disappearance of the SM. The reaction mixture was poured into ice-cold water and extracted with EtOAc (3×100 ml). The combined extracts were washed with water (100 ml), brine (100 ml), dried (Na$_2$SO$_4$) and concentrated. The TLC and the $^1$H NMR showed the presence of two products N alkylated as well as O-alkylated products in a ratio of 75:25. The products were separated by column (silica gel) chromatography using 10% EtOAc in hexanes. The major N-alkylated product 5-benzyl-6-isobutyl-3-methyl-5H-isothiazolo[5,4-d]pyrimidin-4-one was isolated as white crystalline solid (10.8 g, 70%). $^1$H NMR (300 MHz) δ 0.94 (d, 6H), 2.23-2.37 (m, 1H), 2.64 (d, 2H), 2.82 (s, 3H), 5.38 (s, 2H), 7.10-7.38 (m, 5H).

Method 28

5-Benzyl-6-(1-bromo-2-methyl-propyl)-3-methyl-5H-isothiazolo[5,4-d]pyrimidin-4-one (alternative procedure)

To a solution of 5-benzyl-6-isobutyl-3-methyl-5H-isothiazolo[5,4-d]pyrimidin-4-one (method 27) (5.81 g, 18.5 mmol) and sodium acetate (10 g) in acetic acid (100 ml) at 100° C., a solution of the bromine (6 g, 38 mmol) in acetic acid (60 ml) was added dropwise over a period of 20 minutes. The reaction mixture was stirred at that temperature for 30 min and cooled and the TLC (eluent 10% EtOAc in hexanes) and MS showed the complete disappearance of the SM and only the product. The reaction mixture was poured into ice water and extracted with EtOAc (3×60 ml) and the organic layers were combined and washed with 2% sodium thiosulfate solution (60 ml), water (100 ml), brine (100 ml) and dried over Na$_2$SO$_4$. Concentration of the organic layer provided 5-benzyl-6-(1-bromo-2-methyl-propyl)-3-methyl-5H-isothiazolo[5,4-d]pyrimidin-4-one (7.27 g, 99%) as white crystalline solid. $^1$H NMR (300 MHz) δ 0.54 (d, 3H), 1.11 (d, 3H), 2.62-2.76 (m, 1H), 2.83 (s, 3H), 4.42 (d, 1H), 4.80 (d, 1H), 6.22 (d, 1H), 7.12-7.42 (m, 5H).

Method 29

6-(1-Azido-2-methyl-propyl)-5-benzyl-3-methyl-5H-isothiazolo[5,4-d]pyrimidin-4-one (alternative procedure)

To a solution of 5-benzyl-6-(1-bromo-2-methyl-propyl)-3-methyl-5H-isothiazolo[5,4-d]pyrimidin-4-one (method 28) (7.27 g, 18.5 mmol) in anhydrous DMF (60 ml), sodium azide (2.33 g, 37 mmol) was added and the mixture was stirred at room temperature for 2 hour. The TLC of the RM showed the complete disappearance of the starting bromide. The reaction mixture was poured into ice water (300 ml) and extracted with EtOAc (3×100 ml). The organic layer was washed with water (100 ml), brine (100 ml) and dried (Na$_2$SO$_4$). Concentration of the organic layer provided the crude product which was purified by column (silica gel) chromatography using 30% EtOAc in hexanes as eluent to isolate 6-(1-azido-2-methyl-propyl)-5-benzyl-3-methyl-5H-isothiazolo[5,4-d]pyrimidin-4-one (6.16 g, 94%) as a low melting solid. $^1$H NMR (300 MHz) δ 0.57 (d, 3H), 1.07 (d, 3H), 2.50-2.74 (m, 1H), 2.98 (s, 3H), 3.71 (d, 1H), 5.05 (d, 1H), 5.78 (d, 1H), 7.12-7.40 (m, 5H).

Method 30

6-(1-Amino-2-methyl-propyl)-5-benzyl-3-methyl-5H-isothiazolo[5 4-d]pyrimidin-4-one (alternative procedure)

To a solution of 6-(1-azido-2-methyl-propyl)-5-benzyl-3-methyl-5H-isothiazolo[5,4-d]pyrimidin-4-one (method 29) (6.8 g, 19.2 mmol) in methanol (400 ml) was added 5% Pd/C (1 g, 20% by wt.) and the resulting mixture was stirred at r.t. in an atmosphere of H$_2$ and the progress of the reaction was monitored by MS. After the disappearance of the starting material the reaction mixture was filtered through celite and washed with EtOAc. Concentration of the filtrate provided 6-(1-amino-2-methyl-propyl)-5-benzyl-3-methyl-5H-isothiazolo[5,4-d]pyrimidin-4-one (5.42 g, 86%).

Method 31

{3-[1-(5-Benzyl-3-methyl-4-oxo-4,5-dihydro-isothiazolo[5,4-d]pyrimidin-6-yl)-2-methyl-propylaminol]-propyl}-carbamic acid tert-butyl ester (alternative procedure)

To a solution of 6-(1-amino-2-methyl-propyl)-5-benzyl-3-methyl-5H-isothiazolo[5,4-d]pyrimidin-4-one (method 30) (5.4 g, 16.5 mmol) in DCM (100 ml), 4 Å molecular sieves (50 g) was added followed by N-boc protected 3-aminopropanal (2.84 g, 16.5 mmol)) and the reaction mixture was stirred at r.t. overnight and the progress of the reaction was monitored by MS. After the complete disappearance of the starting amine, a catalytic amount of acetic acid was added to the reaction followed by sodium triacetoxyborohydride (3.49 g, 16.5 mmol) and the reaction mixture was stirred at r.t. for 4 h. After the completion of the reaction (MS), the reaction mixture was filtered and the residue was washed with DCM and the filtrate was washed with water (100 mL), brine (100 mL) and concentrated to give {3-[1-(5-Benzyl-3-methyl-4-oxo-4,5-dihydro-isothiazolo[5,4-d]pyrimidin-6-yl)-2-methyl-propylamino]-propyl}-carbamic acid tert-butyl ester (8.3 g, theoretical yield=7.9 g) which was used as such for the next reaction.

Method 33

{3-[[1-(5-Benzyl-3-methyl-4-oxo-4,5-dihydro-isothiazolo[5,4-d]pyrimidin-6-yl)-2-methyl-propyl]-(4-methyl-benzoyl)-amino]-propyl}-carbamic acid tert-butyl ester (alternative procedure)

To a solution of {3-[1-(5-Benzyl-3-methyl-4-oxo-4,5-dihydro-isothiazolo[5,4-d]pyrimidin-6-yl)-2-methyl-propylamino]-propyl}-carbamic acid tert-butyl ester obtained from method 31 alternative procedure above in chloroform (300 ml), diisopropylethylamine (6 g, 46.5 mmol) was added and the reaction mixture was heated to 60° C. To the hot solution a solution of the p-toluoyl chloride (3.78 g, 24.4 mmol) in chloroform (150 ml) was added dropwise and the resulting solution was refluxed overnight. The TLC showed the disappearance of most of the SM. The reaction mixture was washed with water (2×100 ml), satd, NaHCO$_3$ (200 ml) brine (100 ml) and dried (Na$_2$SO$_4$). Concentration of the organic layer provided the crude product which was purified by column (silica gel) chromatography using 10-30% EtOAc in hexanes as eluent. Yield=6.14 g (62%) of {3-[[1-(5-benzyl-3-methyl-4-oxo-4,5-dihydro-isothiazolo[5,4-d]pyrimidin-6-yl)-2-methyl-propyl]-(4-methyl-benzoyl)-amino]-propyl}-carbamic acid tert-butyl ester. White foam, mp. 70-71° C. m/z 604 (MH$^+$), $^1$H NMR (DMSO-d$_6$, 300 MHz, 95° C.) δ: 0.48 (d, 3H), 0.90 (d, 3H), 1.26 m, 1H), 1.28 (s, 9H), 2.33 (s, 3H), 2.47 (d, 2H), 2.72-2.64 (m, 1H), 2.72 (s, 3H), 3.24 (t, 2H), 5.08 (d, 1H), 5.60 (d, 1H), 5.90 (d, 1H), 7.20-7.40 (m, 9H).

Method 63

5-Amino-3-methylisothiazole-4-carboxamide

To a chilled solution of sulfuric acid (7.2 volumes, 12.9 equivs) was charged 5-amino-3-methylisothiazole-4-carbonitrile (method 4) (1.0 equiv). The temperature was maintained below 55° C. The reaction mixture was heated to 70° C. and held for 1 hour until TLC showed disappearance of starting material. The mixture was cooled to 60-65° C. before the ammonia (21 volumes) was charged to pH 10. The mixture was cooled to 20° C., aged overnight and filtered. The resulting solid was washed with dilute ammonia (3.6 volumes) and dried at 40° C. to give a pale brown solid (typical yield 80%).$^1$H NMR (300 MHz, DMSO-d$_6$) δ 2.46(s, 3H), 6.28 (s, 1H).

Method 26

6-Isobutyl-3-methyl-5H-isothiazolo[5,4-d]pyrimidin-4-one (alternative procedure)

To a 2 L flask equipped with Dean Stark was charged 5-amino-3-methylisothiazole-4-carboxamide (method 63) (1 equiv), p-toluene sulphonic acid (0.049 equiv), DMF (9.75 volumes). The reaction was stirred until a solution was obtained and isovaleraldehyde (1.10 equiv) and toluene (4.9 volumes) were added. The resulting mixture was heated to 130° C. and held at reflux for 1 hour removing water via a Dean Stark apparatus. Once the reaction was complete toluene was removed under vacuum distillation. Sodium bisulfite (2.50 equiv) was charged and the mixture was held at 115° C. for 7 hours, then cooled to room temperature overnight. The solid was removed by filtration through harborlite and washed with DMF (1 volume). Analysis showed conversion to product and the reaction was heated to 50° C., water (15 volumes) was added and the resulting precipitate was cooled to room temperature and held for 1 h. The product was isolated by filtration and washed with water (2×0.5 volumes), dried to give a pale brown solid (typical yield 89%).

Method 31

{3-[1-(5-Benzyl-3-methyl-4-oxo-4,5-dihydro-isothiazolo[5,4-d]pyrimidin-6-yl)-2-methyl-propylamino]-propyl}-carbamic acid tert-butyl ester (alternative procedure)

To (3,3-diethoxypropyl)amine (1.00 equiv) in THF (2 volumes) was charged di-t-butyldicarbonate (1.05 equiv) in THF (3 volumes). The reaction was heated to 45° C. and held for ½ h. Analysis showed the disappearance of starting material, and the resulting solution was heated to 65° C. p-Toluene sulphonic acid (0.1 equiv) and water (5 volumes) were charged over 10 mins, heating continued at 65° C. and held for ½ hour. Analysis showed disappearance of tert-butyl (3,3-diethoxypropyl)carbamate. Toluene (15 volumes) charged, layers separated and washed with water (5 volumes). A fraction of the solution obtained (0.95 equivs) was charged to a solution containing 6-(1-amino-2-methyl-propyl)-5-benzyl-3-methyl-5H-isothiazolo[5,4-d]pyrimidin-4-one (method 30) (1 equiv), toluene (5 volumes) and molecular sieves (1 weight equivalent). The reaction mixture was stirred overnight at room temperature until the reaction was complete. THF (2.5 volumes) were charged followed by sodium acetoxyborohydride (2.0 equiv) and the resulting mixture held overnight until reaction was complete. Aqueous acetic acid (20% v/v, 2.5 volumes) were charged over 10 minutes, stirred at room temperature for 10 minutes, filtered and washed with water (2.5 volumes). The layers were separated and the organic layer was concentrated under vacuo at 50° C. Further toluene was charged (2.5 volumes) and the solvent removed. The product was obtained as an orange oil (typical yield 92%). m/z 486 (MH$^+$).

Example A
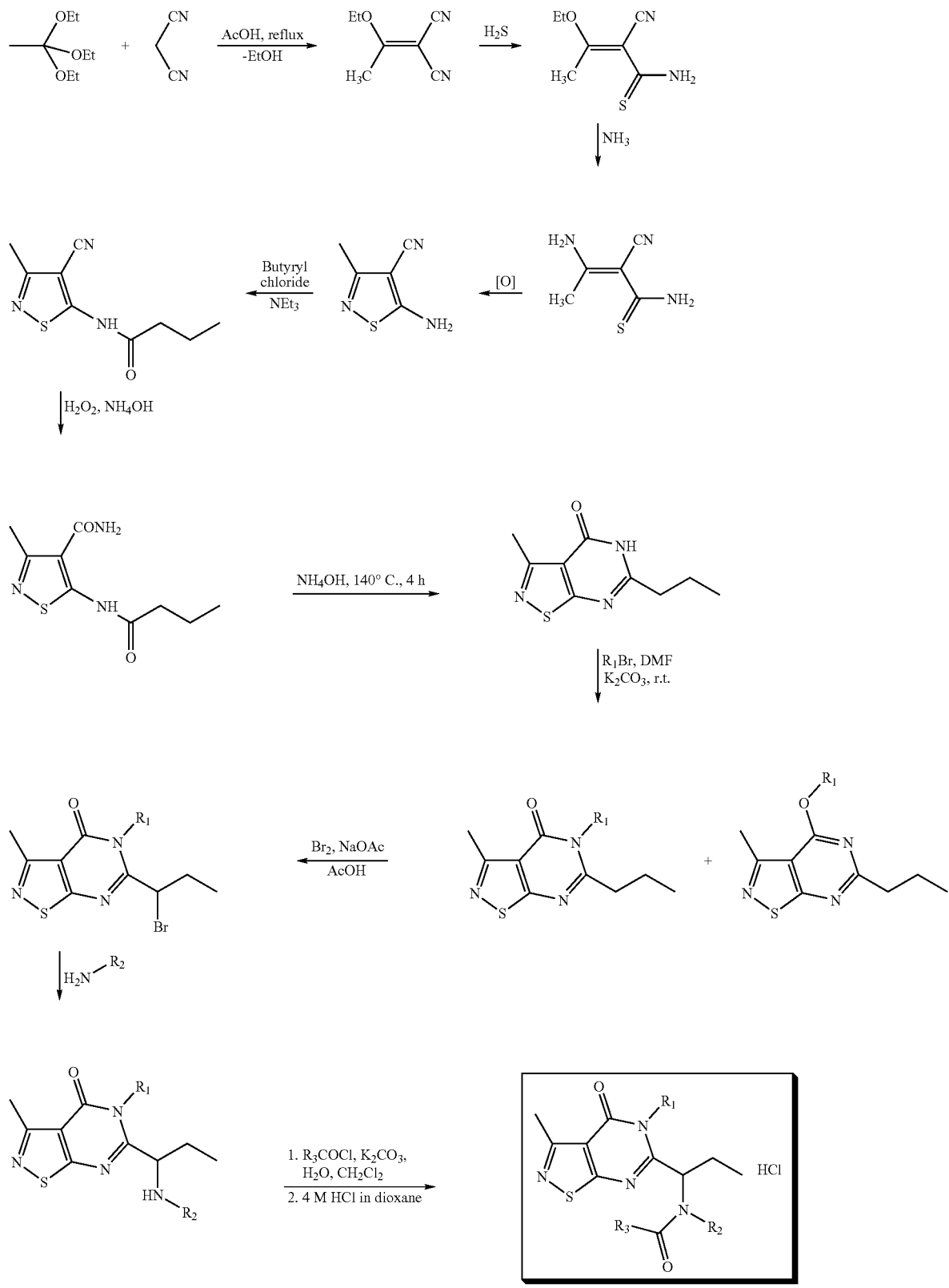

Examples A

The following compounds were synthesized according to synthetic scheme A above:

| Ex. | Compound | ¹H NMR | m/z | SM |
|---|---|---|---|---|
| A1 | (+) N-(3-Amino-propyl)-N-[1-(5-benzyl-3-methyl-4-oxo-4,5-dihydro-isothiazolo[5,4-d]pyrimidin-6-yl)-propyl]-4-methyl-benzamide hydrogen chloride | (DMSO-$d_6$, 500MHz, 96° C.) δ: 0.63(t, 3H), 1.40-1.74(m, 2H), 1.75-1.96(m, 1H), 2.05-2.20(m, 1H), 2.39(s, 3H), 2.46(t, 2H), 2.72(s, 3H), 3.36(t, 2H), 4.83(d, 1H), 5.50(bs, 1H), 5.77(d, 1H), 6.95-7.37(m, 9H), 7.79(bs, 3H) | m/z 490 (MH$^+$) | Method 13 |
| A2 | (+) N-(3-Amino-propyl)-N-{1-[5-(4-fluoro-benzyl)-3-methyl-4-oxo-4,5-dihydro-isothiazolo[5,4-d]pyrimidin-6-yl]-propyl}-4-methyl-benzamide hydrogen chloride | (DMSO-$d_6$, 500MHz, 96° C.) δ: 0.66(t, 3H), 1.38-1.74(m, 2H), 1.82-1.98(m, 1H), 2.02-2.20(m, 1H), 2.34(s, 3H), 2.42(t, 2H), 2.72(s, 3H), 3.36(t, 2H), 4.85(d, 1H), 5.49(bs, 1H), 5.70(d, 1H), 7.05-7.27(m, 8H), 7.76(bs, 3H) | m/z 508 (MH$^+$) | Method 13a |
| A3 | (+) N-(3-Amino-propyl)-N-{1-[5-(3-fluoro-benzyl)-3-methyl-4-oxo-4,5-dihydro-isothiazolo[5,4-d]pyrimidin-6-yl]-propyl}-4-methyl-benzamide hydrogen chloride | (500MHz, DMSO-$d_6$, 100° C.) δ ppm: 0.70(t, 3H), 1.40-1.54(m, 1H), 1.62-1.76(m, 1H), 1.85-2.01(m, 1H), 2.14-2.27(m, 1H), 2.38(s, 3H), 2.44-2.49(m, 2H), 2.76(s, 3H), 3.35-3.46(m, 2H), 4.87(br s, 1H), 5.48(br s, 1H), 5.75(d, 1H), 6.84-6.96(m, 2H), 7.06-7.15(m, 1H), 7.20-7.31(m, 4H), 7.33-7.41(m, 1H), 7.52(br s, 3H) | m/z 508 (MH$^+$) | Method 13b |
| A4 | (+) N-(3-Amino-propyl)-N-[1-(5-benzyl-3-methyl-4-oxo-4,5-dihydro-isothiazolo[5,4-d]pyrimidin-6-yl)-propyl]-4-bromo-benzamide hydrogen chloride | (DMSO-$d_6$, 500MHz, 96° C.) δ: 0.68(t, 3H), 1.50-1.72(m, 2H), 1.91-1.96(m, 1H), 2.13-2.17(m, 1H), 2.47(t, 2H), 2.77(s, 3H), 3.38(t, 2H), 4.95(d, 1H), 5.57(bs, 1H), 5.80(d, 1H), 7.13(m, 2H), 7.28-7.36(m, 5H), 7.64(d, 2H), 7.80(br, 1H) | m/z 554, 556 (MH$^+$) | Method 13g |
| A5 | (+) N-(3-Amino-propyl)-N-[1-(5-benzyl-3-methyl-4-oxo-4,5-dihydro-isothiazolo[5,4-d]pyrimidin-6-yl)-propyl]-4-chloro-benzamide hydrogen chloride | (DMSO-$d_6$, 500MHz, 96° C.) δ: 0.69(t, 3H), 1.42-1.83(m, 2H), 1.89-2.01(m, 1H), 2.10-2.20(m, 1H), 2.46(hidden by DMSO, 2H), 2.77(s, 3H), 3.39(bm, 2H), 4.94(d, 1H), 5.58(bs, 1H), 5.81(d, 1H), 7.12-7.56(m, 9H) | m/z 510 (MH$^+$) | Method 13c |
| A6 | (+) N-(3-Amino-propyl)-N-[1-(5-benzyl-3-methyl-4-oxo-4,5-dihydro-isothiazolo[5,4-d]pyrimidin-6-yl)-propyl]-3-fluoro-4-methyl-benzamide hydrogen chloride | (DMSO-$d_6$, 500MHz, 96° C.) δ: 0.67(t, 3H), 1.45(m, 1H), 1.70(m, 1H), 1.92(m, 1H), 2.16(m, 1H), 2.31(s, 3H), 2.46(2H, hidden by DMSO), 2.76(s, 3H), 3.39(t, 2H), 4.93(d, 1H), 5.54(bs, 1H), 5.81(d, 1H), 7.09-7.52(m, 8H), 7.74(br, 3H) | m/z 508 (MH$^+$) | Method 13d |
| A7 | (+) N-(3-Amino-propyl)-N-[1-(5-benzyl-3-methyl-4-oxo-4,5-dihydro-isothiazolo[5,4-d]pyrimidin-6-yl)-propyl]-2,3-dichloro-benzamide hydrogen chloride | (DMSO-$d_6$, 500MHz, 96° C.) δ: 0.70(t, 3H), 1.50-1.70(m, 2H), 1.94(m, 1H), 2.20(m, 1H), 2.46(m, 2H), 2.78(s, 3H), 3.30(m, 2H), 5.10(d, 1H), 5.82(bs, 1H), 5.93(d, 1H), 7.29-7.72(m, 8H), 7.72(br, 3H) | m/z 544, 545, 546 (MH$^+$) | Method 13e |
| A8 | (+) Benzo[b]thiophene-2-carboxylic acid (3-amino-propyl)-[1-(5-benzyl-3-methyl-4-oxo-4,5-dihydro-isothiazolo[5,4-d]pyrimidin-6-yl)-propyl]amide hydrogen chloride | (DMSO-$d_6$, 500MHz, 96° C.) δ: 0.71(t, 3H), 1.46-1.61(m, 1H), 1.88-1.92(m, 1H), 1.93-1.97(m, 1H), 2.21-2.26(m, 1H), 2.62(t, 2H), 2.76(s, 3H), 3.65(t, 2H), 4.96(d, 1H), 5.66(bs, 1H), 5.78(d, 1H), 7.05(bm, 2H), 7.25(bm, 3H), 7.30-7.50(m, 2H), 7.60(s, 1H), 7.85-7.99(m, 2H) | m/z 532 (MH$^+$) | Method 13f |
| A9 | (+) N-(2-Amino-ethyl)-N-[1-(5-benzyl-3-methyl-4-oxo-4,5-dihydro-isothiazolo[5,4-d]pyrimidin-6-yl)-propyl]-4-methyl-benzamide hydrogen chloride | (DMSO-$d_6$, 500MHz, 96° C.) δ: 0.60(t, 3H), 1.85-2.05(m, 2H), 2.45(s, 3H), 2.76(s, 3H), 2.90(m, 2H), 3.80(m, 2H), 4.70(d, 1H), 5.35(bs, 1H), 5.80(d, 1H), 6.88-7.35(m, 9H), 7.75-7.85(br, 3H) | m/z 476 (MH$^+$) | Method 13h |

| Ex. | Compound | ¹H NMR | m/z | SM |
|---|---|---|---|---|
| A10 | (+) N-[1-(5-Benzyl-3-methyl-4-oxo-4,5-dihydro-isothiazolo[5,4-d]pyrimidin-6-yl)-propyl]-N-(3-dimethylamino-propyl)-4-methyl-benzamide | (DMSO-$d_6$, 90° C.) δ: 0.66(t, 3H), 0.90-1.10(m, 1H), 1.30-1.49(m, 1H), 1.81(m, 8H), 1.85-1.95(m, 1H), 2.05-2.15(m, 1H), 2.35(s, 3H), 2.75(s, 3H), 3.41(t, 2H), 4.96(d, 1H), 5.71(bs, 1H), 5.92(d, 1H), 7.10-7.44(m, 9H) | m/z 518 (MH⁺) | Method 12i |
Example B
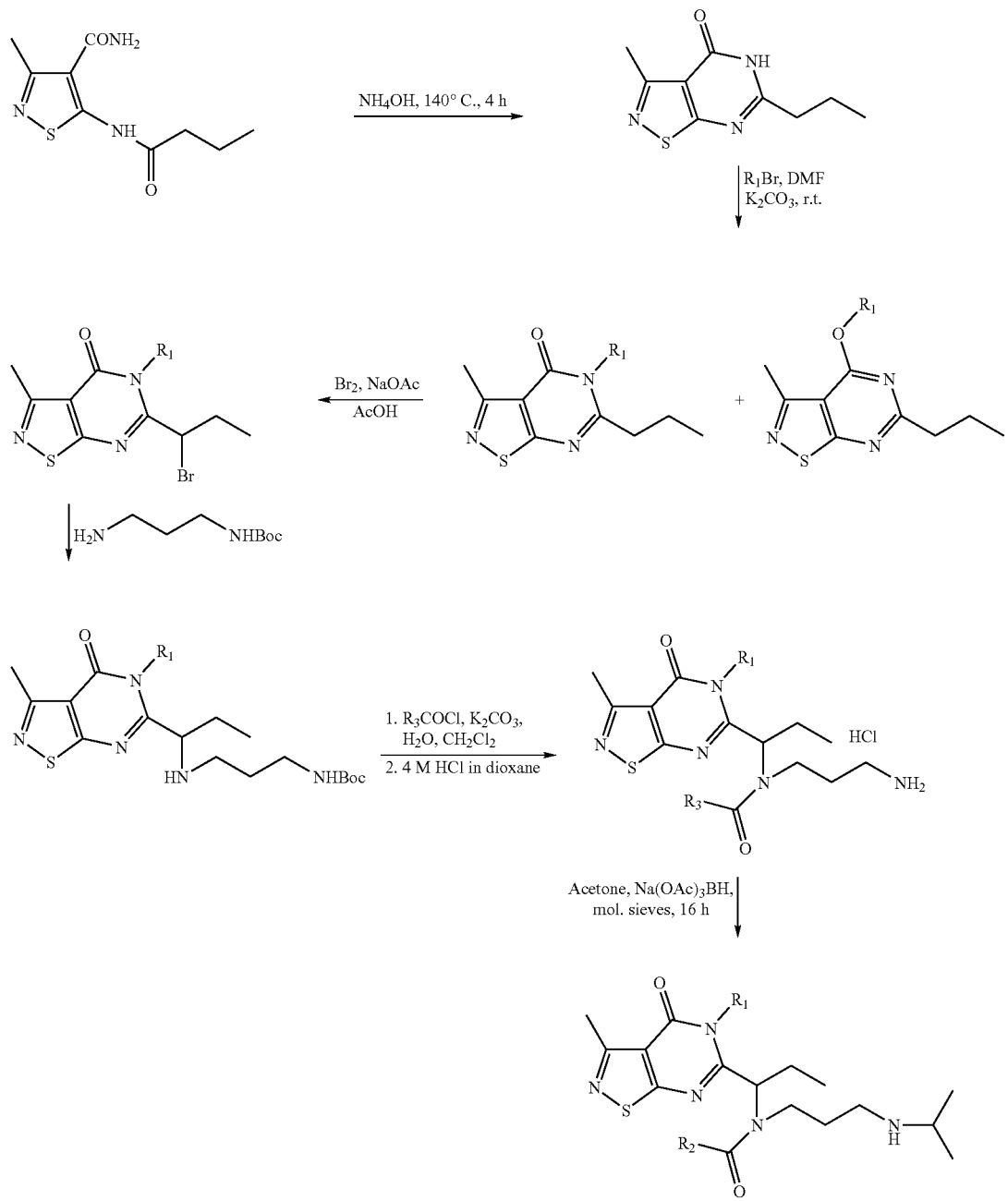

Example B
The following compounds were synthesized according to synthetic scheme B above:
| Ex. | Compound | $^1$H NMR | m/z | SM |
|---|---|---|---|---|
| B1 | (+) N-[1-(5-Benzyl-3-methyl-4-oxo-4,5-dihydro-isothiazolo[5,4-d]pyrimidin-6-yl)-propyl]-N-(3-isopropylamino-propyl)-4-methyl-benzamide | (DMSO-$d_6$, 90° C.) δ: 0.65(t, 3H), 0.75-0.85(d, 6H), 1.01-1.11(m, 1H), 1.35-1.50(m, 1H), 1.80-1.98(m, 1H), 2.00-2.19(m, 3H), 2.35(s, 3H), 2.80(s, 3H), 3.00-3.05(b, 2H), 3.40(m, 2H), 4.90(d, 1H), 5.70(bs, 1H), 5.80(d, 1H), 7.00-7.40(m, 9H) | m/z 532 (MH$^+$) | Method 15 |
Example C
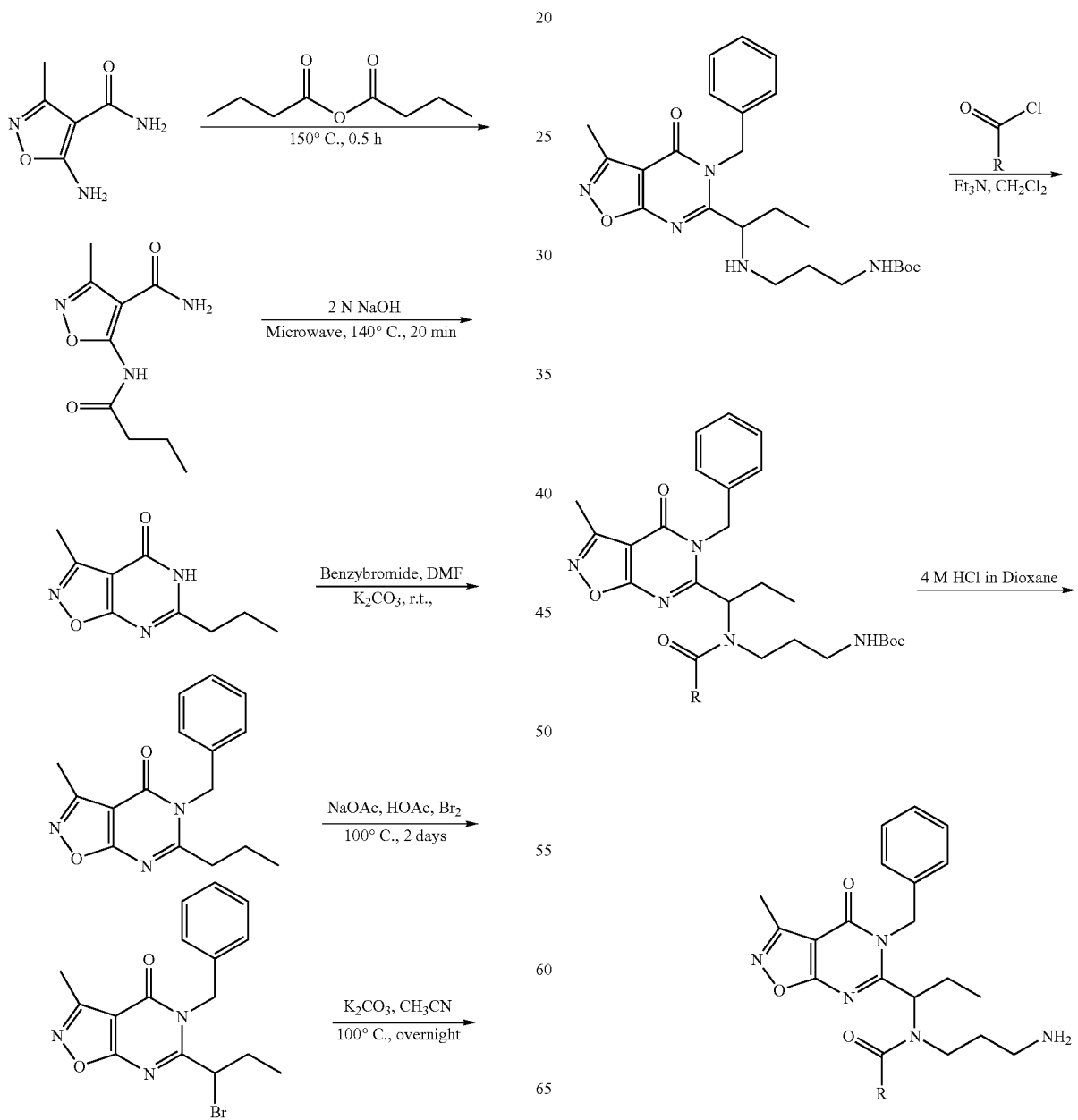

Example C
The following compounds were synthesized according to synthetic scheme C above:
| Ex. | Compound | $^1$H NMR | m/z | SM |
| --- | --- | --- | --- | --- |
| C1 | (+) N-(3-Amino-propyl)-N-[1-(5-benzyl-3-methyl-4-oxo-4,5-dihydro-isoxazolo[5,4-d]pyrimidin-6-yl)-propyl]-4-methyl-benzamide hydrogen chloride | (500MHz, 100° C., DMSO-$d_6$) δ: 0.68(t, 3H), 1.52(m, 1H), 1.72(m, 1H), 1.92(m, 1H), 2.10(m, 1H), 2.39(s, 3H), 2.51(m, 2H), 2.57(s, 3H), 3.41(m, 2H), 4.85(br, 1H), 5.50(br, 1H), 5.77(d, 1H), 7.07(br, 2H), 7.24-7.35(m, 7H), 7.73(br, 3H) | m/z 474 (MH$^+$) | Method 23 |
Example D
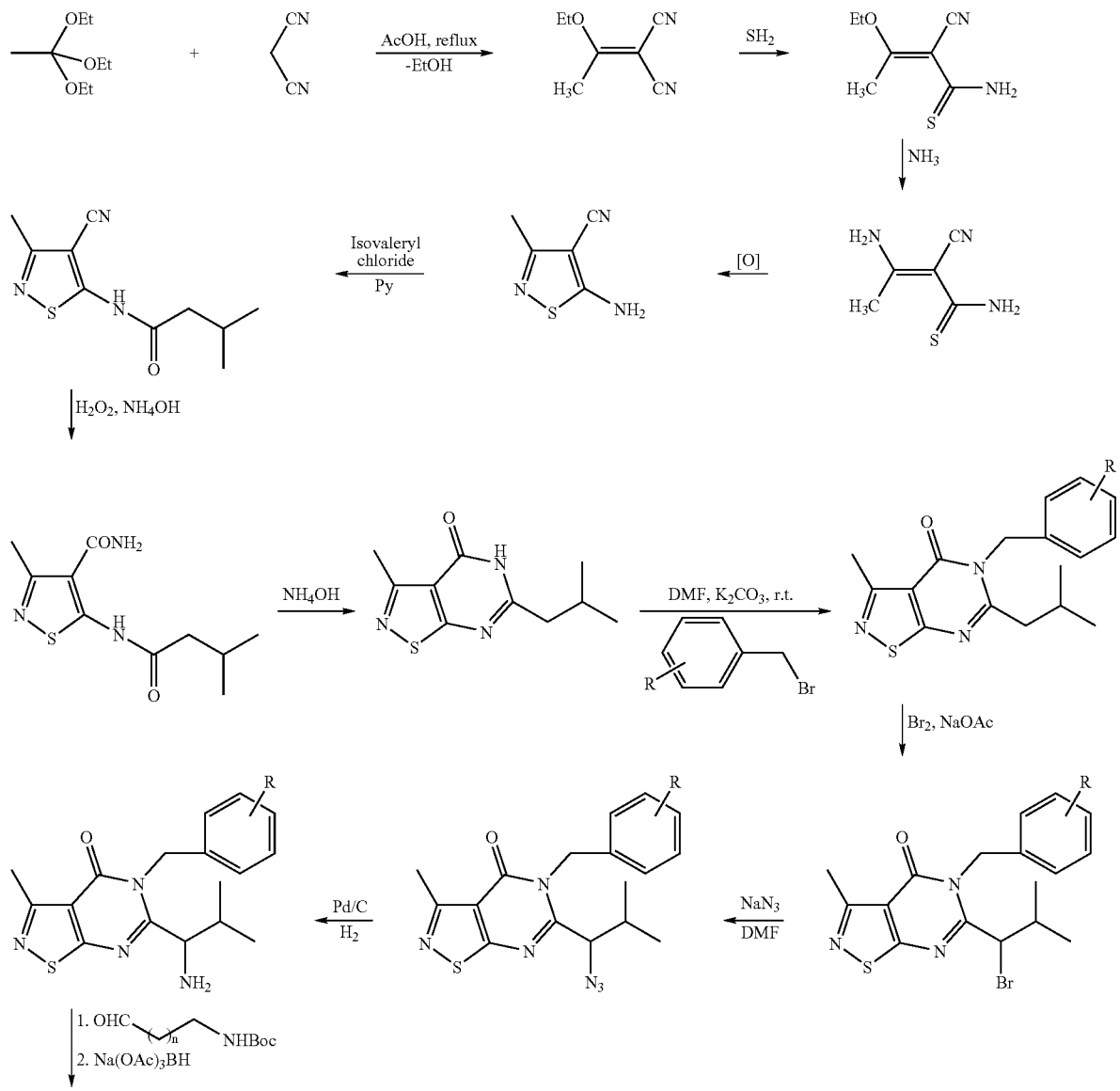

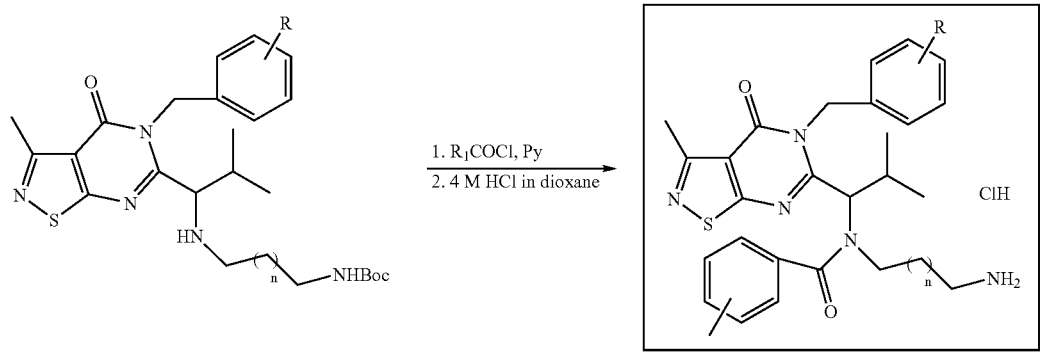

Examples D

The following compounds were synthesized according to synthetic scheme D above:

| Ex. | Compound | $^1$H NMR | m/z | SM |
|---|---|---|---|---|
| D1 | (+) N-(3-Amino-propyl)-N-{1-[5-(4-fluoro-benzyl)-3-methyl-4-oxo-4,5-dihydro-isothiazolo[5,4-d]pyrimidin-6-yl]-2-methyl-propyl}-4-methyl-benzamide hydrogen chloride | (90° C., DMSO-$d_6$) δ: 0.47(d, 3H), 0.92(d, 3H), 1.10-1.28(m, 1H), 1.44-1.56(m, 1H), 2.27(t, 2H), 2.36(s, 3H), 2.66-2.72(m, 1H), 2.75(s, 3H), 3.35(t, 2H), 5.04(d, 1H), 5.57(d, 1H), 5.86(d, 1H), 7.12-7.43(m, 8H), 7.71-7.81(m, 3H) | m/z 522 (MH$^+$) | Method 35a |
| D2 | (+) N-(3-Amino-propyl)-N-[1-(5-benzyl-3-methyl-4-oxo-4,5-dihydro-isothiazolo[5,4-d]pyrimidin-6-yl)-2-methyl-propyl]-4-methyl-benzamide | (500MHz, 96° C., DMSO-$d_6$) δ: 0.45(d, 3H), 0.90(d, 3H), 1.12-1.30(m, 1H), 1.46-1.63(m, 1H), 2.25(t, 2H), 2.36(s, 3H), 2.64-2.7(m, 1H), 2.68(s, 3H), 3.34(t, 2H), 5.06(d, 1H), 5.59(d, 1H), 5.90(d, 1H), 7.20-7.40(m, 9H), 7.71(bs, 3H) | m/z 504 (MH$^+$) | Method 36 |
| D3 | (+) N-(3-Amino-propyl)-N-{1-[5-(3-fluoro-benzyl)-3-methyl-4-oxo-4,5-dihydro-isothiazolo[5,4-d]pyrimidin-6-yl]-2-methyl-propyl}-4-methyl-benzamide | (500MHz, DMSO-$d_6$, 90° C.) δ: 0.52(d, 3H), 0.94(d, 3H), 1.15-1.25(m, 1H), 1.26-1.33(m, 1H), 1.45-1.58(m, 1H), 2.32(m, 2H), 2.38(s, 3H), 2.78(s, 3H), 3.32-3.40(m, 2H), 5.11(bd, 1H), 5.56(bd, 1H), 5.90-5.93(d, 1H), 7.11-7.38(m, 8H), 7.58(b, 2H) | m/z 522 (MH$^+$) | Method 35b |
| D4 | (+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-bromo-benzamide hydrogen chloride | (500MHz, DMSO-$d_6$, 96° C.) δ: 0.44(d, 3H), 0.90(d, 3H), 1.09-1.12(m, 1H), 2.55-2.75(m, 2H), 2.79(s, 3H), 3.62-3.75(m, 2H), 5.05(m, 1H), 5.60(d, 1H), 5.93(d, 1H), 7.21-7.40(m, 9H), 7.61(m, 4H) | m/z 554, 556 (MH$^+$) | Method 35d |
| D5 | (+) N-(2-Amino-ethyl)-N-[1-(5-benzyl-3-methyl-4-oxo-4,5-dihydro-isothiazolo[5,4-d]pyrimidin-6-yl)-2-methyl-propyl]-4-methyl-benzamide hydrogen chloride | (DMSO-$d_6$, 500MHz, 90° C.) δ: 0.39(d, 3H), 0.93(d, 3H), 2.40(bm, 4H), 2.55-2.70(m, 2H), 2.79(s, 3H), 3.68-3.75(m, 2H), 5.00(b, 1H), 5.55(b, 1H), 5.91-5.95(d, 1H), 7.15-7.43(m, 9H), 7.60-7.71(bs, 2H). | m/z 490 (MH$^+$) | Method 35c |
| D6 | (+) N-(2-Amino-ethyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide hydrogen chloride | (500MHz, DMSO-$d_6$, 90° C.) δ: 0.39(d, 3H), 0.93(d, 3H), 2.20-2.39(m, 4H), 2.60-2.70(m, 2H), 2.79(s, 3H), 3.63-3.74(m, 2H), 5.00(m, 1H), 5.55(b, 1H), 5.91-5.95(d, 1H), 7.15-7.48(m, 8H), 7.68(bs, 2H) | m/z 508 (MH$^+$) | Method 35e |
| D7 | (+) N-(3-Amino-propyl)-N-[1-(5-benzyl-3-methyl-4-oxo-4,5-dihydro-isothiazolo[5,4-d]pyrimidin-6-yl)-2-methyl-propyl]-3-fluoro-4-methyl-benzamide hydrogen chloride | (500MHz, DMSO-$d_6$, 90° C.) δ: 0.48(d, 3H), 0.93(d, 3H), 1.18(m, 1H), 1.53(m, 1H), 2.32-2.51(s, m, 5H), 2.82(s, 4H), 3.35-3.43(m, 2H), 5.10(m, 1H), 5.62(m, 1H), 5.94(d, 1H), 7.11-7.38(m, 8H), 7.51(b, 2H) | m/z 522 (MH$^+$) | Method 35f |

-continued
| Ex. | Compound | ¹H NMR | m/z | SM |
|---|---|---|---|---|
| D8 | (+) N-(3-Amino-propyl)-N-[1-(5-benzyl-3-methyl-4-oxo-4,5-dihydro-isothiazolo[5,4-d]pyrimidin-6-yl)-2-methyl-propyl]-4-bromo-benzamide hydrogen chloride | (DMSO-$d_6$, 90° C.) δ: 0.48(d, 3H), 0.93(m, 3H), 1.10-1.20(m, 1H), 1.45-1.60(m, 1H), 2.28-2.41(t, 2H), 2.63-2.79(m, s, 4H), 3.35-3.43(m, 2H), 5.08(m, 1H), 5.62(m, 1H), 5.96(d, 1H), 7.30-7.50(m, 7H), 7.52-7.80(br, m, 4H) | m/z 568, 570 (MH⁺) | Method 35g |
Example E
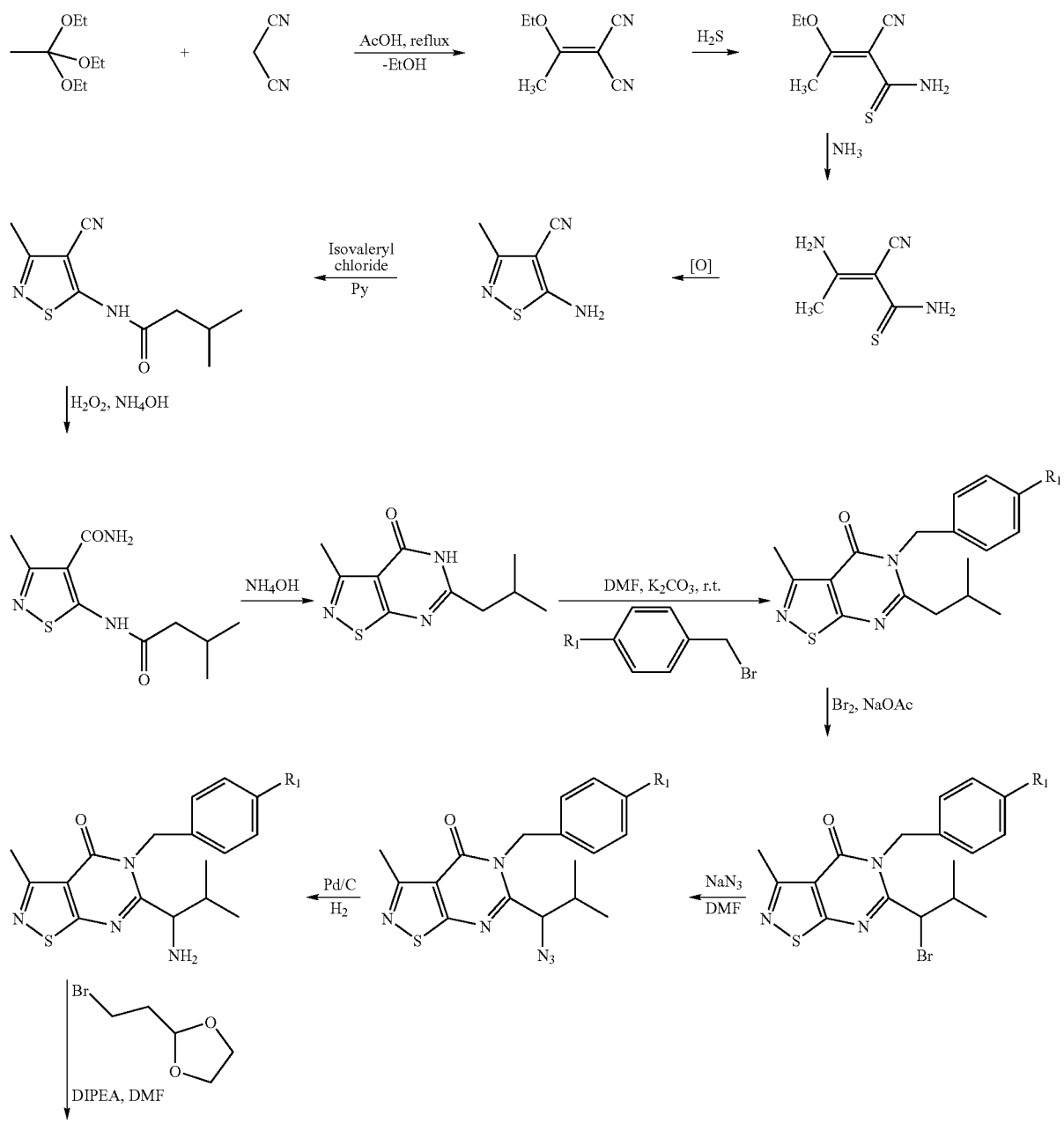

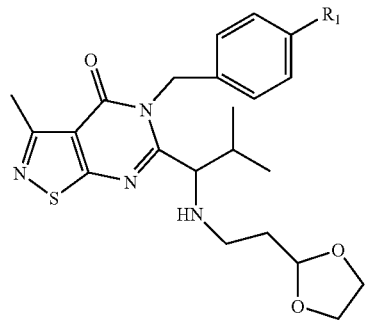
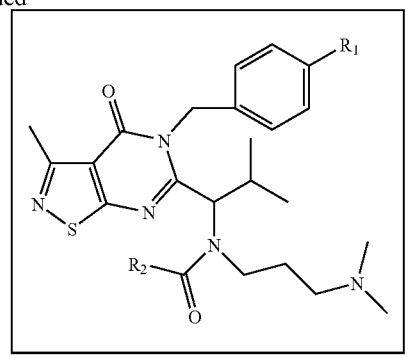

Examples E

The following compounds were synthesized according to synthetic scheme E above:

| Ex. | Compound | $^1$H NMR | m/z | SM |
|---|---|---|---|---|
| E1 | (+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-methyl-benzamide | (DMSO-d$_6$, 90° C.) δ: 0.36(d, 3H), 0.73(m, 1H), 0.96(d, 3H), 1.26-1.27(m, 1H), 1.65-1.87(br m, s, 8H), 2.37(s, 3H), 2.72(m, 1H), 2.87(s, 3H), 3.35-3.41(m, 2H), 5.22-5.27(d, 1H), 5.73-5.76(d, 1H), 6.12-6.17(d, 1H), 7.22-7.41(m, 9H) | m/z 532 (MH$^+$) | Method 40a |
| E2 | (+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-4-bromo-benzamide | (DMSO-d$_6$, 90° C.) δ: 0.36(d, 3H), 0.73(m, 1H), 0.95(d, 3H), 1.20-1.23(m, 1H), 1.64-1.82(br m, s, 8H), 2.69(m, 1H), 2.87(s, 3H), 3.35-3.37(m, 2H), 5.17-5.22(d, 1H), 5.71-5.75(d, 1H), 6.12-6.17(d, 1H), 7.21-7.57(m, 9H) | m/z 596, 598 (MH$^+$) | Method 40 |
| E3 | (+) N-[1-(5-Benzyl-3-methyl-4-oxo-4,5-dihydro-isothiazolo[5,4-d]pyrimidin-6-yl)-2-methyl-propyl]-N-(3-dimethylamino-propyl)-3-fluoro-4-methyl-benzamide | (DMSO-d$_6$, 90° C.) δ: 0.36(d, 3H), 0.73(m, 1H), 0.94(d, 3H), 1.20-1.23(m, 1H), 1.65-1.83(br m, s, 8H), 2.30(s, 3H), 2.69(m, 1H), 2.87(s, 3H), 3.35-3.41(t, 2H), 5.17-5.23(d, 1H), 5.71-5.74(d, 1H), 6.11-6.16(d, 1H), 6.99-7.39(m, 8H) | m/z 540 (MH$^+$) | Method 40b |

Example F

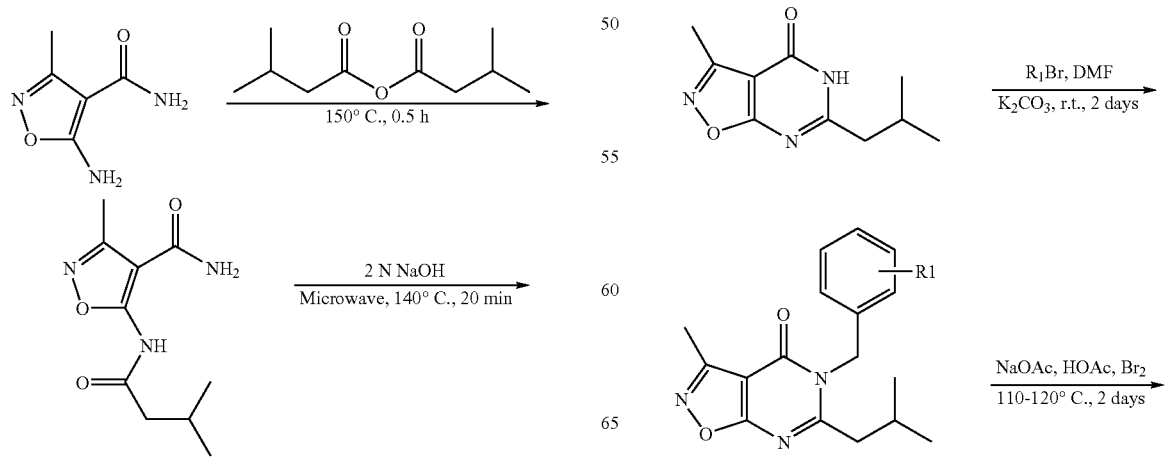

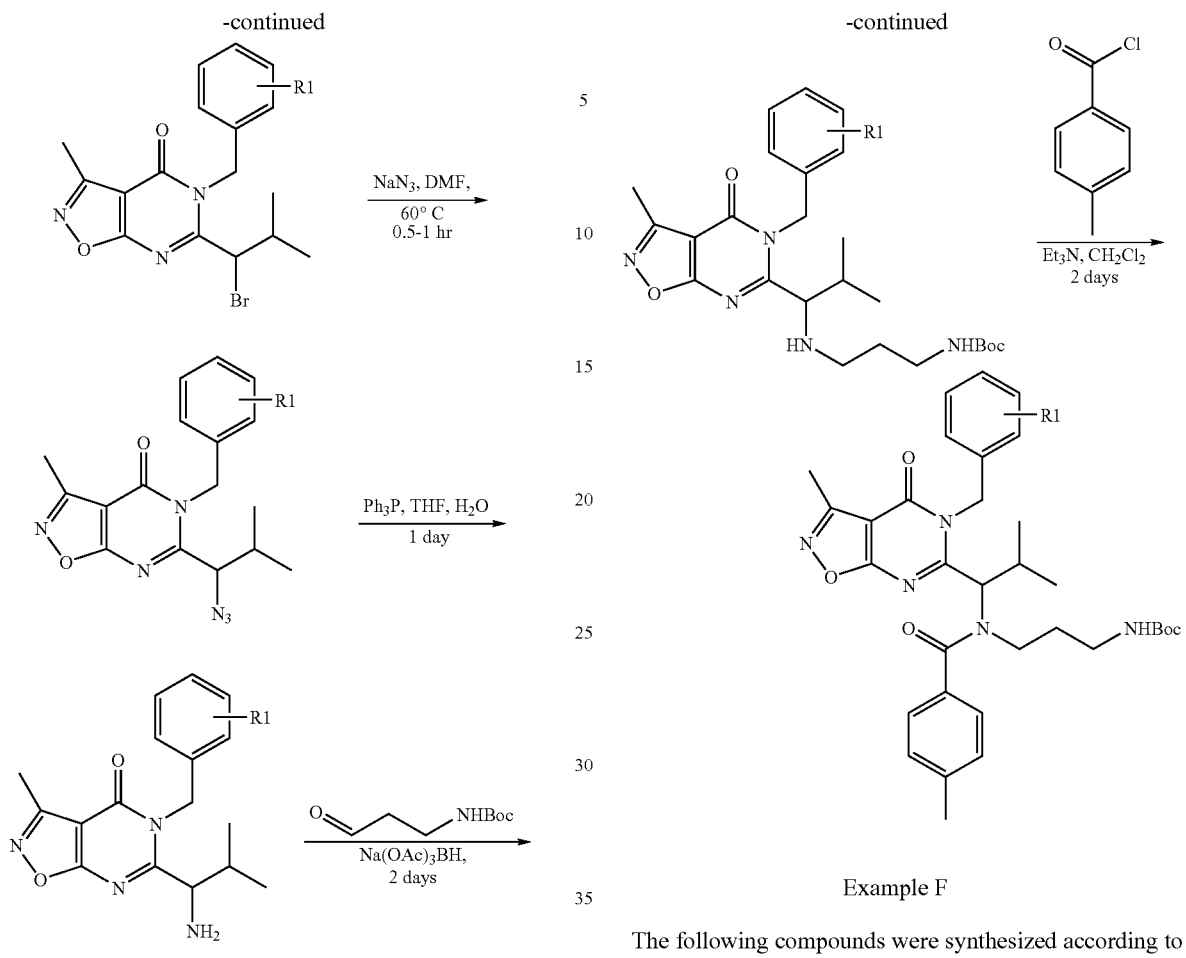

Example F

The following compounds were synthesized according to synthetic scheme F above:

| Ex. | Compound | $^1$H NMR | m/z | SM |
|---|---|---|---|---|
| F1 | (+) N-(3-Amino-propyl)-N-[1-(5-benzyl-3-methyl-4-oxo-4,5-dihydro-isoxazolo[5,4-d]pyrimidin-6-yl)-2-methyl-propyl]-4-methyl-benzamide | (500MHz, 100° C., DMSO-d$_6$): δ: 0.48(d, 3H), 0.94(d, 3H), 1.20-1.45(m, m, 2H), 2.15(m, 2H), 2.38(s, 3H), 2.58 (s, 3H), 2.70(m, 1H), 3.37(m, 2H), 5.11(d, 1H), 5.64(d, 1H), 5.90(d, 1H), 7.23-7.39(m, 9H) | m/z 488 (MH$^+$) | Method 51 |
| F2 | (+) N-(3-Amino-propyl)-N-{1-[5-(4-fluoro-benzyl)-3-methyl-4-oxo-4,5-dihydro-isoxazolo[5,4-d]pyrimidin-6-yl]-2-methyl-propyl}-4-methyl-benzamide | (500MHz, 100° C., DMSO-d$_6$) δ: 0.50(d, 3H), 0.95-1.10(d, m, 4H), 1.55(m, 1H), 2.32(m, 2H), 2.40(s, 3H), 2.60(s, 3H), 2.75(m, 1H), 3.40(m, 2H), 5.10(d, 1H), 5.60(d, 1H), 5.88(d, 1H), 7.17-7.34(m, 8H) | m/z 506 (MH$^+$) | Method 51a |
| F3 | (+) N-(3-Amino-propyl)-N-{1-[5-(3-fluoro-benzyl)-3-methyl-4-oxo-4,5-dihydro-isoxazolo[5,4-d]pyrimidin-6-yl]-2-methyl-propyl}-4-methyl-benzamide hydrogen chloride | (90° C., DMSO-d$_6$) δ: 0.44(d, 3H), 0.96(d, 3H), 1.15-1.35(m, 1H), 1.50-1.71(m, 1H), 2.36(m, s, 4H), 2.60(s, 3H), 2.60-2.80(m, 2H), 3.43-3.54(m, 2H), 5.10(m, 1H), 5.62(d, 1H), 5.82(d, 1H), 7.12-7.37(m, 8H), 7.60(br, 3H) | m/z 506 (MH$^+$) | Method 50b |

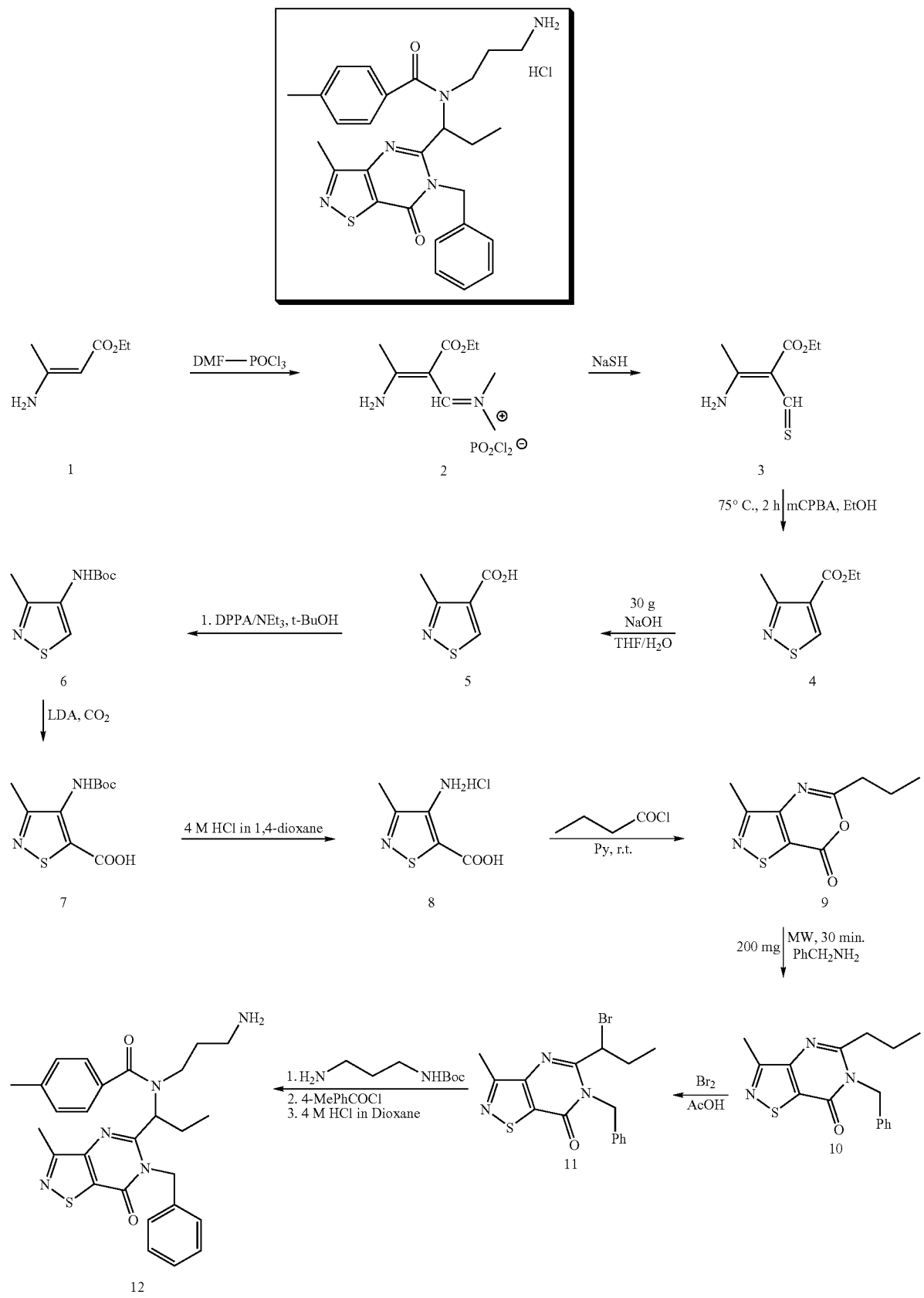

Example G

The following compounds were synthesized according to synthetic scheme G above:

| Ex. | Compound | $^1$H NMR | m/z | SM |
|---|---|---|---|---|
| G1 | (+) N-(3-Amino-propyl)-N-[1-(6-benzyl-3-methyl-7-oxo-6,7-dihydro-isothiazolo[4,5-d]pyrimidin-5-yl)-propyl]-4-methyl-benzamide | (DMSO-$d_6$, 90° C.) δ 0.65(t, 3H), 1.36-1.50(m, 1H), 1.60-1.72(m, 1H), 1.88-1.99(m, 1H), 2.14-2.26(m, 1H), 2.35(s, 3H), 2.47(t, 2H), 2.68(s, 3H), 3.32-3.44(m, 2H), 4.90(d, 1H), 5.50(b, 1H), 5.76(d, 1H), 6.96-7.34(m, 9H), 7.68(bs, 3H). | m/z 490 (MH$^+$) | Method 62 |

Chiral Rotations of the Examples

Rotations were measured on a Perkin Elmer Model 341 polarimeter. The compounds were dissolved to a concentration of 1 mg/ml in methanol and the measurements were made at 20.0° C., at 589 nM. 1 ml of solution was used.

| Example | Rotation |
|---|---|
| A1 | + |
| C1 | + |
| D2 | + |
| A8 | + |
| D5 | + |
| A5 | + |
| A4 | + |
| D4 | + |
| D6 | + |
| A6 | + |
| A7 | + |
| F2 | + |
| F1 | + |
| A3 | + |
| A10 | + |
| A2 | + |
| A9 | + |
| D7 | + |
| D8 | + |
| D3 | + |
| D1 | + |
| B1 | + |
| E2 | + |
| E1 | + |
| E3 | + |
| G1 | + |
| F3 | + |

Utility

Compounds of formula (I) have been shown to inhibit the microtubule motor protein HsEg5 in vitro. Inhibitors of Eg5 have been shown to inhibit the formation of a mitotic spindle and therefore for cell division. Inhibitors of Eg5 have been shown to block cells in the metaphase of mitosis leading to apoptosis of effected cells, and to therefore have anti-proliferative effects. It is believed that Eg5 inhibitors act as modulators of cell division and are expected to be active against neoplastic disease such as carcinomas of the brain, breast, ovary, lung, colon, prostate or other tissues, as well as multiple myeloma leukemias, for example myeloid leukemia, acute lymphoblastic leukemia, chronic myeloid leukemia, chronic lymphocytic leukemia, and lymphomas for example Hodgkins disease and non-Hodgkins lymphoma, tumors of the central and peripheral nervous system, and other tumor types such as melanoma, fibrosarcoma, Ewing's sarcoma and osteosarcoma. Therefore it is believed that the compounds of formula (I) may be used for the treatment of neoplastic disease. Hence the compounds of formula (I) and their salts and their in vivo hydrolysable esters are expected to be active against carcinomas of the brain, breast, ovary, lung, colon, prostate or other tissues, as well as leukemias and lymphomas, tumors of the central and peripheral nervous system, and other tumor types such as melanoma, fibrosarcoma and osteosarcoma. The compounds of formula (I) and their salts and their in vivo hydrolysable esters are expected to be active against neoplastic disease such as carcinomas of the brain, breast, ovary, lung, colon, prostate or other tissues, as well as multiple myeloma leukemias, for example myeloid leukemia, acute lymphoblastic leukemia, chronic myeloid leukemia, chronic lymphocytic leukemia, and lymphomas for example Hodgkins disease and non-Hodgkins lymphoma, tumors of the central and peripheral nervous system, and other tumor types such as melanoma, fibrosarcoma, Ewing's sarcoma and osteosarcoma. It is expected that the compounds of formula (I) would most likely be used in combination with a broad range of agents but could also be used as a single agent.

Generally, the compounds of formula (I) have been identified in the Malachite Green Assay described herein as having an $IC_{50}$ value of 100 micromolar or less. For example compound A7 ((+) N-(3-Amino-propyl)-N-[1-(5-benzyl-3-methyl-4-oxo-4,5-dihydro-isothiazolo[5,4-d]pyrimidin-6-yl)-propyl]-2,3-dichloro-benzamide hydrogen chloride) has an $IC_{50}$ value of 136 nM.

Compounds provided by this invention should also be useful as standards and reagents in determining the ability of a potential pharmaceutical to inhibit Eg5. These would be provided in commercial kits comprising a compound of this invention.

Malachite Green Assay

Enzymatic activity of the Eg5 motor and effects of inhibitors was measured using a malachite green assay, which measures phosphate liberated from ATP, and has been used previously to measure the activity of kinesin motors (Hackney and Jiang, 2001). Enzyme was recombinant HsEg5 motor domain (amino acids 1-369-8His) and was added at a final concentration of 6 nM to 100 μl reactions. Buffer consisted of 25 mM PIPES/KOH, pH 6.8, 2 mM $MgCl_2$, 1 mM EGTA, 1 mM dtt, 0.01% Triton X-100 and 5 μM paclitaxel. Malachite green/ammonium molybdate reagent was prepared as follows: for 800 ml final volume, 0.27 g of Malachite Green (J. T. Baker) was dissolved in 600 ml of $H_2O$ in a polypropylene bottle. 8.4 g ammonium molybdate (Sigma) was dissolved in 200 ml 4N HCl. The solutions were mixed for 20 min and filtered through 0.02 μm filter directly into a polypropylene container. 5 μl of compound diluted in 12% DMSO was added to the wells of 96 well plates. 80 μl of enzyme diluted in buffer solution above was added per well and incubated with compound for 20 min. After this pre-incubation, substrate solution containing 2 mM ATP (final concentration: 300 μM) and 6,053 μM polymerized tubulin (final concentration: 908 nM) in 15 μl of buffer were then added to each well to start reaction. Reaction was mixed and incubated for an additional 20 min at room temperature. The reactions were then quenched by the addition of 150 μl malachite green/ammonium molybdate reagent, and absorbance read at 650 nanometers exactly 5 min after quench using a Spectramax Plus plate reader (Molecular Devices). Data was graphed and IC$_{50}$s calculated using ExCel Fit (Microsoft).

The invention claimed is:

1. (R) N-(3-aminopropyl)-N-[1-(5-benzyl-3-methyl-4-oxo-4,5-dihydroisothiazolo[5,4-d]pyrimidin-6-yl)-2-methylpropyl]-4-methylbenzamide, or a pharmaceutically acceptable salt thereof, which is substantially free of (S) N-(3-aminopropyl)-N-[1-(5-benzyl-3-methyl-4-oxo-4,5-dihydroisothiazolo[5,4-d]pyrimidin-6-yl)-2-methylpropyl]-4-methylbenzamide.

2. (R) N-(3-aminopropyl)-N-[1-(5-benzyl-3-methyl-4-oxo-4,5-dihydroisothiazolo[5,4-d]pyrimidin-6-yl)-2-methylpropyl]-4-methylbenzamide, or a pharmaceutically acceptable salt thereof, according to claim 1, wherein (S) N-(3-aminopropyl)-N-[1-(5-benzyl-3-methyl-4-oxo-4,5-dihydroisothiazolo[5,4-d]pyrimidin-6-yl )-2-methylpropyl]-4-methylbenzamide is present in an amount of no more than 2% w/w.

3. (R) N-(3-aminopropyl)-N-[1-(5-benzyl-3-methyl-4-oxo-4,5-dihydroisothiazolo[5,4-d]pyrimidin-6-yl)-2-methylpropyl]-4-methylbenzamide, or a pharmaceutically acceptable salt thereof, according to claim 1, wherein (S) N-(3-aminopropyl)-N-[1-(5-benzyl-3-methyl-4-oxo-4,5-dihydroisothiazolo[5,4-d]pyrimidin-6-yl )-2-methylpropyl]-4-methylbenzamide is present in an amount of no more than 1% w/w.

4. A pharmaceutical composition comprising (R) N-(3-aminopropyl)-N-[1-(5-benzyl-3-methyl-4-oxo-4,5-dihydroisothiazolo[5,4-d]pyrimidin-6-yl)-2-methylpropyl]-4-methylbenzamide, or a pharmaceutically acceptable salt thereof, which is substantially free of (S) N-(3-aminopropyl)-N-[1-(5-benzyl-3-methyl-4-oxo-4,5-dihydroisothiazolo[5,4-d]pyrimidin-6-yl)-2-methylpropyl]-4-methylbenzamide and at least one pharmaceutically acceptable carrier, diluent or excipient.

* * * * *